US008735092B2

United States Patent
Hatanaka et al.

(10) Patent No.: US 8,735,092 B2
(45) Date of Patent: May 27, 2014

(54) GLUCOSE-INDUCED INACTIVATION/DEGRADATION-RESISTANT TRANSPORTER GENE AND USE THEREOF

(75) Inventors: Haruyo Hatanaka, Osaka (JP); Fumihiko Omura, Osaka (JP)

(73) Assignee: Suntory Holdings Limited, Osaka (JP)

( * ) Notice: Subject to any disclaimer, the term of this patent is extended or adjusted under 35 U.S.C. 154(b) by 0 days.

(21) Appl. No.: 12/442,143

(22) PCT Filed: Sep. 9, 2008

(86) PCT No.: PCT/JP2008/066237
§ 371 (c)(1),
(2), (4) Date: Nov. 5, 2010

(87) PCT Pub. No.: WO2010/029609
PCT Pub. Date: Mar. 18, 2010

(65) Prior Publication Data
US 2011/0104331 A1 May 5, 2011

(51) Int. Cl.
*A61K 38/00* (2006.01)
*C12G 1/022* (2006.01)
*C12C 12/00* (2006.01)
*C07K 14/395* (2006.01)

(52) U.S. Cl.
CPC ............ *C07K 14/395* (2013.01); *C12G 1/0203* (2013.01); *C12C 12/006* (2013.01); *C12C 12/004* (2013.01); *C12G 2200/11* (2013.01)
USPC ............ 435/69.1; 435/6; 435/7.1; 435/320.1; 435/23.1; 536/23.1

(58) Field of Classification Search
None
See application file for complete search history.

(56) References Cited

U.S. PATENT DOCUMENTS 7,314,974 B2 *  1/2008  Cao et al. ................ 800/289
2008/0229451 A1 *  9/2008  Cao et al. ................ 800/281

FOREIGN PATENT DOCUMENTS

WO     2007/026049 A2   3/2007

OTHER PUBLICATIONS

Brondijk et al. "Catabolite Inactivation of Wild-type and Mutant Maltose Transport Proteins in *Saccharomyces cerevisiae*" (1998) *J. Biol. Chem.* 273(25):15352-15357.
Kenji et al. Japan Society for Bioscience, Biotechnology, and Agrochemistry 2001 Nendo Taikai Koen Yoshishu (2001) p. 341 (3Y1p6).
Kodama et al. *Journal of Bioscience and Bioengineering* (2004) 82(5) p. 219.
Kodama et al. "Improvement of Maltose Fermentation Efficiency: Constitutive Expression of *MAL* Genes in Brewing Yeasts" (1995) *J. Am. Soc. Brew. Chem.* (1995) 53(1):24-29.
Yao et al. "Primary Structure of the Maltose-Permease-Encoding Gene of *Saccharomyces carlsbergensis*" (1989) *Gene* 79:189-197.
Han et al. "Characterization of the *AGT1* Encoding a General α-Glucoside Transporter from *Saccharomyces*" (1995) *Mol. Microbiol.* 17(6):1093-1107.
Day et al. "Characterization of the Putative Maltose Transporters Encoded by YDL247w and YJR160c" (2002) *Yeast* 19:1015-1027.
Dietvorst et al. "Maltotriose Utilization in Lager Yeast Strains: *MTT1* Encodes a Maltotriose Transporter" (2005) *Yeast* 22(10):775-788.
Gadura et al. "Sequences in the N-terminal Cytoplasmic Domain of *Saccharomyces cerevisiae* Maltose Permease are Required for Vacuolar Degradation but not Glucose-Induced Internalization" (2006) *Curr. Genet.* 50(2):101-114.
Medintz et al. "A PEST-like Sequence in the N-Terminal Cytoplasmic Domain of *Saccharomyces* Maltose Permease is Required for Glucose-Induced Proteolysis and Rapid Inactivation of Transport Activity" (2000) *Biochemistry* 39(15):4518-4526.
U.S. Appl. No. 12/442,121 to Hatanaka et al., entitled "Glucose-Induced Inactivation/Degradation-Resistant Transporter Gene and Use Thereof" which application is the National Stage of PCT/JP2008/066241, filed Sep. 9, 2008.
U.S. Appl. No. 12/442,131 to Hatanaka et al., entitled "Hybrid Alpha-Glucoside Transporter" which application is the National Stage of PCT/JP2008/066239, filed Sep. 9, 2008.
Hatanaka et al., "Gly-46 and His-50 of Yeast Maltose Transporter Mal21p Are Essential for Its Resistance Against Glucose-Induced Degradation" *Journal of Biological Chemistry*, vol. 284, No. 23, pp. 15448-15457, 2009.
Cheng et al., "The Maltose Permease Encoded by the *MAL61* Gene of *Saccharomyces cerevisiae* Exhibits Both Sequence and Structural Homology to Other Sugar Transporters" *Genetics*, vol. 123, No. 3, pp. 477-484, 1989.
Extended European Search Report for European App. No. EP 08831280.6, dated Jan. 11, 2011.
Chinese Office Action issued with respect to patent family member Chinese Application No. 200880000636.9, dated Jul. 1, 2011.

* cited by examiner

*Primary Examiner* — Hope Robinson
(74) *Attorney, Agent, or Firm* — Greenblum & Bernstein, P.L.C.

(57) ABSTRACT

The present invention relates to a glucose-induced inactivation- or degradation-resistant transporter gene and use thereof, and more particularly, to a brewing yeast having excellent assimilation of oligosaccharides (e.g., maltose or maltotriose), an alcoholic beverage prepared using the yeast, and a method of producing the alcoholic beverage. More specifically, the present invention relates to a glucose-induced inactivation- or degradation-resistant transporter including, for example, Mal21p, mutant Mal31p, mutant Mal61p, mutant Mtt1p or mutant Agt1p, a gene encoding the transporter, and a method of producing an alcoholic beverage using the same.

12 Claims, 15 Drawing Sheets

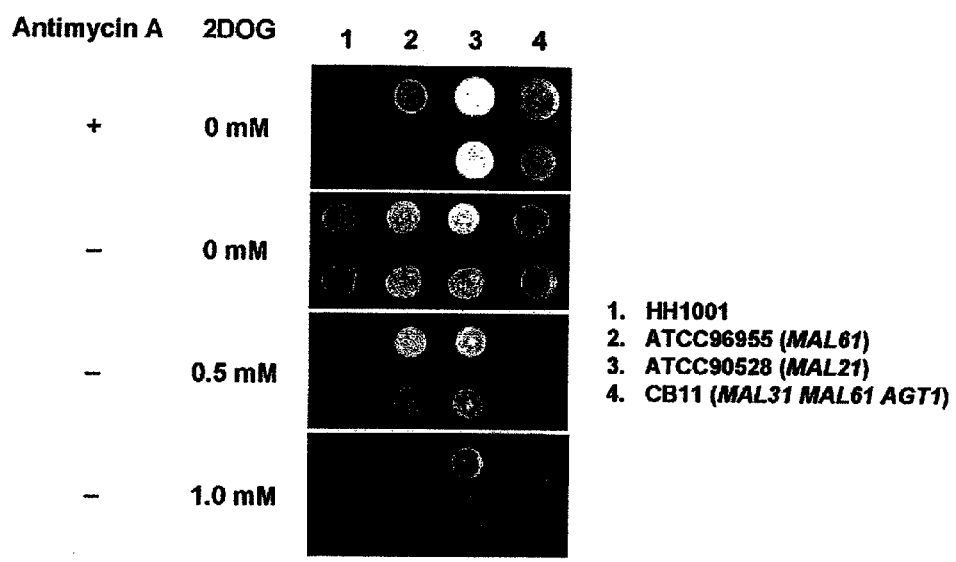
FIG. 1: Differences in growth among laboratory yeasts in the presence of 2-deoxyglucose

```
   1 ATGAAGGGAT TATCCTCATT AATAAACAGA AAAAAAGACA GGAACGACTC
  51 ACACTTAGAT GAGATCGAGA ATGGCGTGAA CGCTACCGAA TTCAACTCGA
 101 TAGAGATGGA GGAGCAAGGT AAGAAAAGTG ATTTTGGTCT TTCCCATCAT
 151 GAGTACGGTC CAGGTTCACT AATACCAAAC GATAATAATG AAGAAGTCCC
 201 CGACCTTCTC GATGAAGCTA TGCAGGACGC CAAAGAGGCA GATGAAAGTG
 251 AGAGGGGAAT GCCACTCATG ACAGCTTTGA AGACATATCC AAAAGCTGCT
 301 GCTTGGTCAC TATTAGTTTC CACAACATTG ATTCAAGAGG GTTATGACAC
 351 AGCCATTCTA GGAGCTTTCT ATGCCCTGCC TGTTTTTCAA AAAAAATATG
 401 GTTCTTTGAA TAGCAATACA GGAGATTATG AAATTTCAGT TTCTTGGCAA
 451 ATCGGTCTAT GTCTATGCTA CATGGCAGGT GAAATTGTGG GGCTACAGCT
 501 AACGGGGCCC TCCGTGGATC TTGTTGGAAA TCGTTACACA TTGATCATGG
 551 CGTTGTTCTT TTTAGCGGCT TTCATTTTCA TTCTGTATTT TTGCAAGAGT
 601 TTGGGTATGA TTGCCGTGGG ACAGGCATTG TGTGGTATGC CATGGGGTTG
 651 TTTCCAATGT TTGACCGTTT CTTATGCTTC TGAAATTTGT CCTTTGGCCC
 701 TAAGATACTA TTTGACGACT TATTCTAATT TATGTTGGAC GTTCGGTCAA
 751 CTTTTCGCTG CTGGTATTAT GAAAAATTCC CAGAACAAAT ATGCCAACTC
 801 AGAACTAGGA TATAAGCTAC CTTTTGCTTT GCAGTGGATC TGGCCCCTTC
 851 CTTTGGCGGT AGGTATTTTT TTTGCACCAG AGTCTCCATG GTGGCTGGTT
 901 AAAAAAGGAA GGATTGATCA AGCGAGGAGA TCACTTGAAA GAACATTAAG
 951 TGGTAAAGGA CCCGAGAAAG AATTACTAGT GACTATGGAA CTCGATAAAA
1001 TCAAAACTAC TATAGAAAAG GAGCAGAAAA TGTCTGATGA AGGAACTTAC
1051 TGGGATTGTG TGAAAGATGG TATTAACAGG AGAAGAACGA GAATAGCTTG
1101 TTTATGTTGG ATCGGTCAAT GCTCCTGTGG TGCATCATTA ATTGGTTATT
1151 CAACTTACTT TTATGAAAAA GCTGGTGTTA GCACTGATAC GGCTTTTACT
1201 TTCAGTATTA TCCAATATTG TCTTGGTATT GCTGCAACGT TTGTATCCTG
1251 GTGGGCTTCA AAATATTGTG GCAGATTTGA CCTTTATGCT TTTGGGCTGG
1301 CTTTTCAGGC TATTATGTTC TTCATTATCG GTGGTTTAGG ATGTTCAGAC
1351 ACTCATGGCG CTAAAATGGG TAGTGGTGCT CTTCTAATGG TTGTCGCGTT
1401 CTTTTACAAC CTCGGTATTG CACCTGTTGT TTTTTGCTTA GTGTCTGAAA
1451 TGCCGTCTTC AAGGCTAAGA ACCAAAACAA TTATTTTGGC TCGTAATGCT
1501 TACAATGTGA TCCAAGTTGT AGTTACAGTT TTGATTATGT ACCAATTGAA
1551 CTCAGAGAAA TGGAATTGGG GTGCTAAATC AGGCTTTTTC TGGGGAGGAT
1601 TTTGTCTGGC CACTTTAGCT TGGGCTGTTG TCGATTTACC AGAAACCGCT
1651 GGCAGGACTT TTATTGAGAT AAATGAATTG TTTAGACTTG GTGTTCCAGC
1701 AAGAAAGTTC AAGTCGACTA AAGTCGACCC TTTTGCAGCT GCCAAAGCAG
1751 CAGCTGCAGA AATTAATGTT AAAGATCCGA AGGAAGATTT GGAAACTTCT
1801 GTGGTAGATG AAGGGCGAAA CACCTCATCT GTTGTGAACA AATGA
```

FIG. 2: MAL21 DNA sequence

MKGLSSLINRKKDRNDSHLDEIENGVNATEFNSIEMEEQGKKSDFGLSHH 50

EYGPGSLIPNDNNEEVPDLLDEAMQDAKEADESERGMPLMTALKTYPKAA 100

AWSLLVSTTLIQEGYDTAILGAFYALPVFQKKYGSLNSNTGDYEISVSWQ 150

IGLCLCYMAGEIVGLQLTGPSVDLVGNRYTLIMALFFLAAFIFILYFCKS 200

LGMIAVGQALCGMPWGCFQCLTVSYASEICPLALRYYLTTYSNLCWTFGQ 250

LFAAGIMKNSQNKYANSELGYKLPFALQWIWPLPLAVGIFFAPESPWWLV 300

KKGRIDQARRSLERTLSGKGPEKELLVTMELDKIKTTIEKEQKMSDEGTY 350

WDCVKDGINRRRTRIACLCWIGQCSCGASLIGYSTYFYEKAGVSTDTAFT 400

FSIIQYCLGIAATFVSWWASKYCGRFDLYAFGLAFQAIMFFIIGGLGCSD 450

THGAKMGSGALLMVVAFFYNLGIAPVVFCLVSEMPSSRLRTKTIILARNA 500

YNVIQVVVTVLIMYQLNSEKWNWGAKSGFFWGGFCLATLAWAVVDLPETA 550

GRTFIEINELFRLGVPARKFKSTKVDPFAAAKAAAAEINVKDPKEDLETS 600

VVDEGRNTSSVVNK*

FIG. 3: Mal21p amino acid sequence

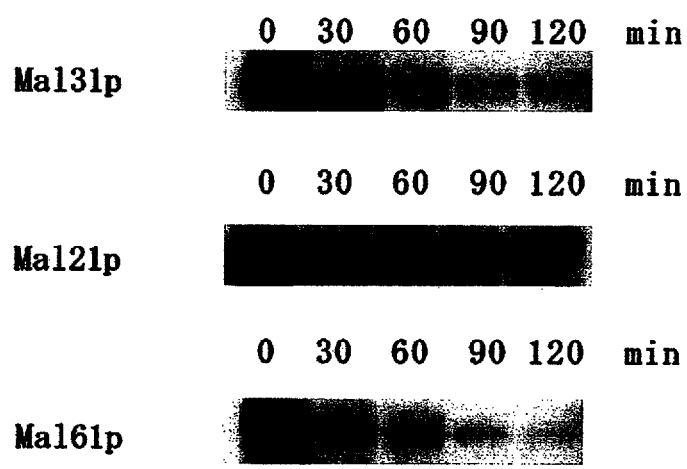
FIG. 4: Degradation rates of Mal21p, Mal31p and Mal61p in the presence of glucose

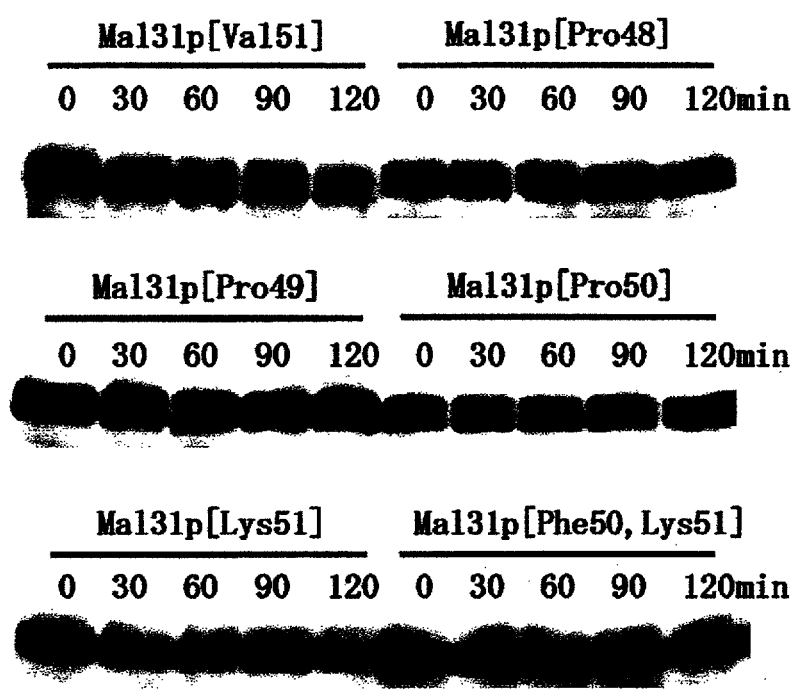
FIG. 5: Degradation rate of mutant Mal31p in the presence of glucose

```
MAL21p   (1)    MKGLSSLINRK-----KDRNDSHLDEIENGVNATEFNSIEMEEQGK-KSDFGLSHHEYGPGSLIPNDNNEEVPDLLDEA--MQDAKEADESERGMPLMTAL
MAL31p   (1)    MKGLSSLINRK-----KDRNDSHLDEIENGVNATEFNSIEMEEQGK-KSDFDLSHLEYGPGSLIPNDNNEEVPDLLDEA--MQDAKEADESERGMPLMTAL
MAL61p   (1)    MKGLSSLINRK-----KDRNDSHLDEIENGVNATEFNSIEMEEQGK-KSDFDLSHLEYGPGSLIPNDNNEEVPDLLDEA--MQDAKEADESERGMPLMTAL
MTT1p    (1)    MKGLSSLINRK-----KDRNDSHLDEIENGVNATEFNSIEMEEQGK-KSDFDLSHHEYGPGSLTPNDNNEEVPDLLDEA--MQDAKEADESERGMPLMTAL
AGT1p    (1)    MKNIISLVSKKKAASKNEDKNISESSRDIVNQQEVTNTEDFEEGKKDSAFELDHLEFTTNSAQLGDSDEDNENVINEMNATDDANEANSEEKSMTLKQAL

MAL21p  (94)    KTYPKAAAWSLLVSTTLIQEGYDTAILGAFYAL PVTQKKYGSLNSNTGDYEISVSWQIGLCICLYMAGEIVGLQLTGPSVDLVGNRYTLIMALFFLAAFIF
MAL31p  (94)    KTYPKAAAWSLLVSTTLIQEGYDTAILGAFYAL PVTQKKYGSLNSNTGDYEISVSWQIGLCICLYMAGEIVGLQMTGPSVDLYMGNRYTLIMALFFLAAFIF
MAL61p  (94)    KTYPKAAAWSLLVSTTLIQEGYDTAILGAFYAL PVTQKKYGSLNSNTGDYEISVSWQIGLCICLYMAGEIVGLQVTGPSVDLYMGNRYTLIMALFFLAAFIF
MTT1p   (94)    KTYPKAAAWSLLVSTTLIQEGYDTAILGSFYAL PVTQKKYGSLNSNTGDYEISASWQIGLSLCVTAGEIVGLQMTGPFVDYMGNRYTLILALILLAAFTF
AGT1p  (101)    LKYPKAALWSILVSTTLVMEGYDTALLSALYAL PVFQRKFGTLNG-EGSYEITSQWQIGLNMCVLCGEMIGLQITTYMVEFMGNRYTMTTALGLLTAYIF

MAL21p (194)    ILYFCKSLGMIAVGQALCGMPWGCFQCLTVSYASEICPLALRYYLITYSNLCWTFGQLFAAGIMKNSQNKYANSELGYKLPFALQWIWPLPLAVGIFFAP
MAL31p (194)    ILYFCKSLGMIAVGQALCGMPWGCFQCLTVSYASEICPLALRYYLITYSNLCWAFGQLFAAGIMKNSQNKYANSELGYKLPFALQWIWPLPLAVGIFFAP
MAL61p (194)    ILYFCKSLGMIAVGQALCGMPWGCFQCLTVSYASEICPLALRYYLITYSNLCWTFGQLFAAGIMKNSQNKYANSELGYKLPFALQWIWPLPLAVGIFLAP
MTT1p  (194)    ILYFCKGLGMIAVGQVLCGMPWGCFQCFQCLITVSYASEICPMALRYLRYLTTYSNLCWTFGQLFAAGIMKNSQNKYPNSELGYKLPFALQWIWPLPLAIGIFFAP
AGT1p  (200)    ILYYCKSLAMIAVGQILSAIFWGCFQSLAVTYASEVCPLALRYYMTSYSNICWLFGQIFASGIMKNSQENLGNSDLGYKLPFALQWIWPLPLMIGIFFAP

MAL21p (294)    ESPWWLVKKGRIDQARRSLERTLSGKGPEKELLVTMELDKIKTTIEKEQKMSD-EGTYWDCVKDGINRRRTRIACLCWIGQCSCGASLIGYSTYFYEKAG
MAL31p (294)    ESPWWLVKKGRIDQARRSLERTLSGKGPEKELLVSMELDKIKTTIEKEQKMSD-EGTYWDCVKDGINRRRTRIACLCWIGQCSCGASLIGYSTYFYEKAG
MAL61p (294)    ESPWWLVKKGRIDQARRSLERILSGKGPEKELLVSMELDKIKTTIEKEQKMSD-EGTYWDCVKDGINRRRTRIACLCWIGQCSCGASLIGYSTYFYEKAG
MTT1p  (294)    ESPWWLVKKGRIDQARRSLERTLSGKGPEKELLVSMELDKIKVTIEKEKKLSDSEGSYWDCLKDSVNRRRTRIACLCWVGQTTCGTSLIGNSTYFYEKAG
AGT1p  (300)    ESPWWLVRKDRVAEARKSLSRILSRILSGKGAEKDIQVDLITLKQIELTIEKERLLASKSGSFFNCFKG--VNGRRTRLACLTWVAQNSSGAVLLGYSTYFFERAG
```

FIG. 6

```
MAL21p (393) VSTDTAFTFSIIQYCLGIAATFVSWWASKYCGRFDLYAFGLAFQAIMFFIIGGLGCSDTHGAKMGSGALLMVVAFFYNLGIAPVVFCLVSEMPSSRLRTK
MAL31p (393) VSTDTAFTFSIIQYCLGIAATFISWWASKYCGRFDLYAFGLAFQAIMFFIIGGLGCSDTHGAKMGSGALLMVVAFFYNLGIAPVVFCLVSEIPSSRLRTK
MAL61p (393) VSTDTAFTFSIIQYCLGIAATFVSWWASKYCGRFDLYAFGLAFQAIMFFIIGGLGCSDTHGAKMGSGALLMVVAFFYNLGIAPVVFCLVSEMPSSRLRTK
MTT1p  (394) VGTDTAFTFSIIQYCLGIAATFLSWWASKYFGRFDLYAFGLAIQTVSLFIIGGLGCSDSHGAEMGSGSLLMVLSFFYNLGIAPVVFCLVSEIPSSRLRTK
AGT1p  (399) MATDKAFTFSLIQYCLGLAGTLCSWVISGRVGRWTILTYGLAFQMVCLFIIGGMGFGSGSSASNGAGGLLLALSFFYNAGIGAVVYCIVAEIPSAELRTK

MAL21p (493) TIILARNAYNVIQVVVTVLIMYQINSEKWNWGAKSGFFWGGFCLATLAWAVVDLPETAGRTFIEINELFRLGVPARKFKSTKVDPFAAAKAAAAEINVKD
MAL31p (493) TIILARNAYNVIQVVVTVLIMYQINSEKWNWGAKSGFFWGGFCLATLAWAVVDLPETAGRTFIEINELFRLGVPARKFKSTKVDPFAAAKAAAAEINVKD
MAL61p (493) TIILARNAYNVIQVVVTVLIMYQINSEKWNWGAKSGFFWGGFCLATLAWAVVDLPETAGRTFIEINELFRLGVPARKFKSTKVDPFAAAKAAAAEINVKD
MTT1p  (494) SIILARNAYNMASIVTTVLIMYQINSEKWNWGAKSGFFWGGLCFATIVWAVIDLPETAGRTFIEINELFRLGVPARKFKSTKVDFFAAAKAAAAEINVKD
AGT1p  (499) TIVLARICYNLMAVINAILTPYMLNVSDWNWGAKTGLYWGGFTAVTLAWVIIDLPETTGRTFSEINELFNQGVPARKFASTVDPFGKGK---TQHDSLAD

MAL21p (593) PKEDLETSVVDEGRNTSSVVNK-
MAL31p (593) PKEDLETSVVDEGRNTSSVVNK-
MAL61p (593) PKEDLETSVVDEGRSTPSVVNK-
MTT1p  (594) PKEDLETSVVDEGRSTPSVVNK-
AGT1p  (597) ESISQSSSIKQRELNAADKC---
```

FIG.7

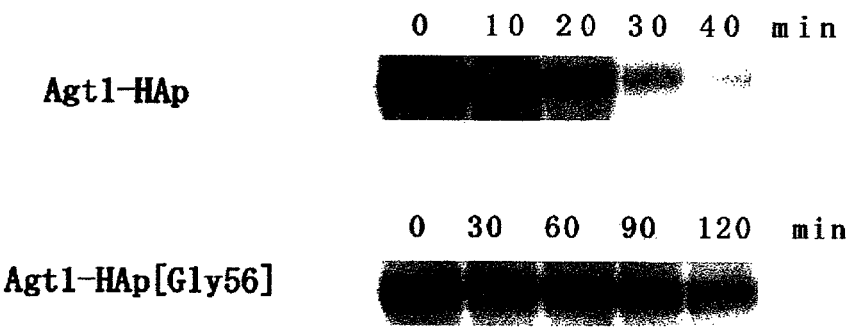
FIG. 8: Degradation rate of mutant Agt1p in the presence of glucose
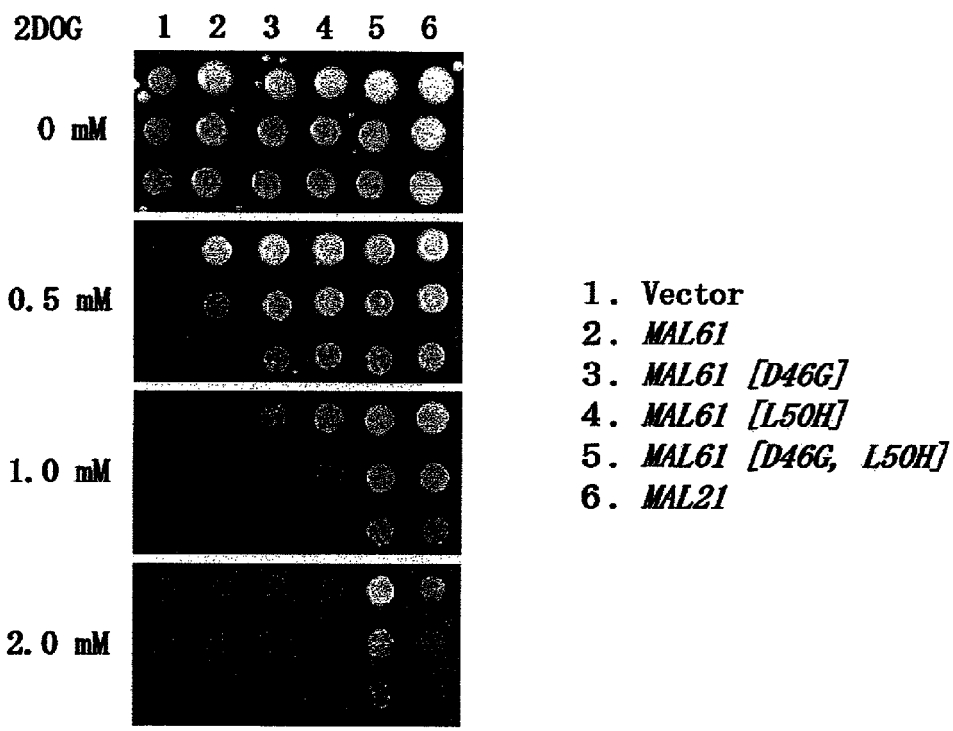
1. Vector
2. *MAL61*
3. *MAL61 [D46G]*
4. *MAL61 [L50H]*
5. *MAL61 [D46G, L50H]*
6. *MAL21*
FIG. 9: Differences in growth among strains bearing mutant MAL61 gene in the presence of 2-deoxyglucose - identification of amino acid residues greatly affecting the degradation rate

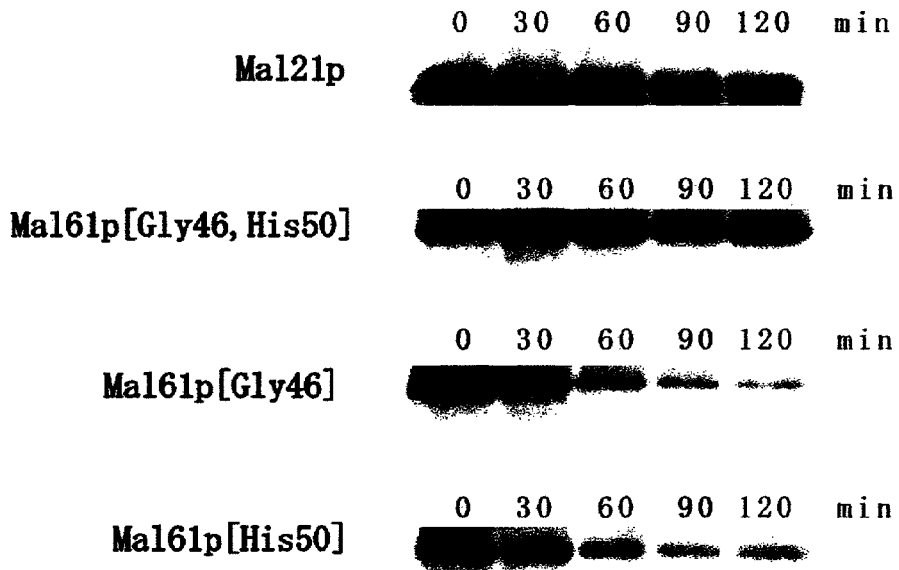
FIG. 10: Degradation rate of mutant Mal61p in the presence of glucose identification of amino acid residues greatly affecting the degradation rate
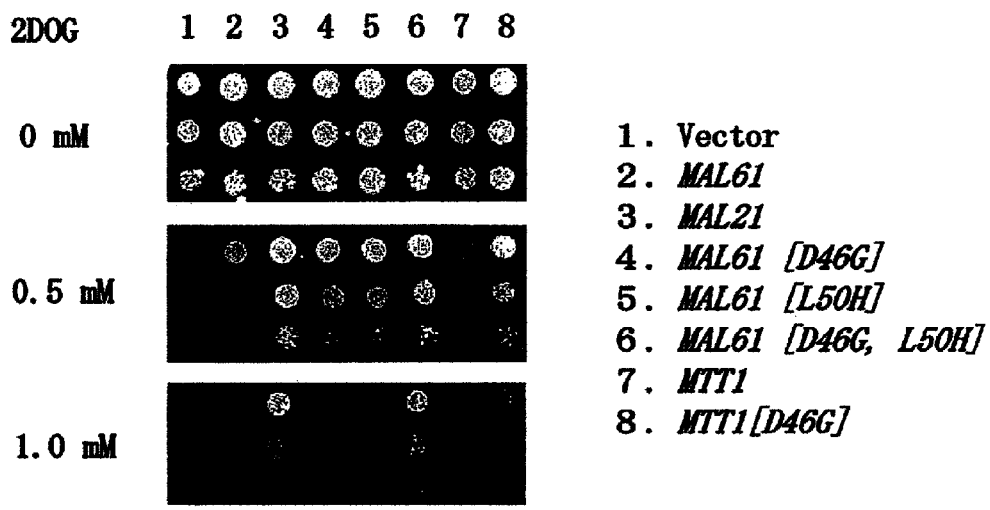
FIG. 11: Differences in growth among strains bearing native MTT1 and mutant MTT1 gene in the presence of 2-deoxyglucose

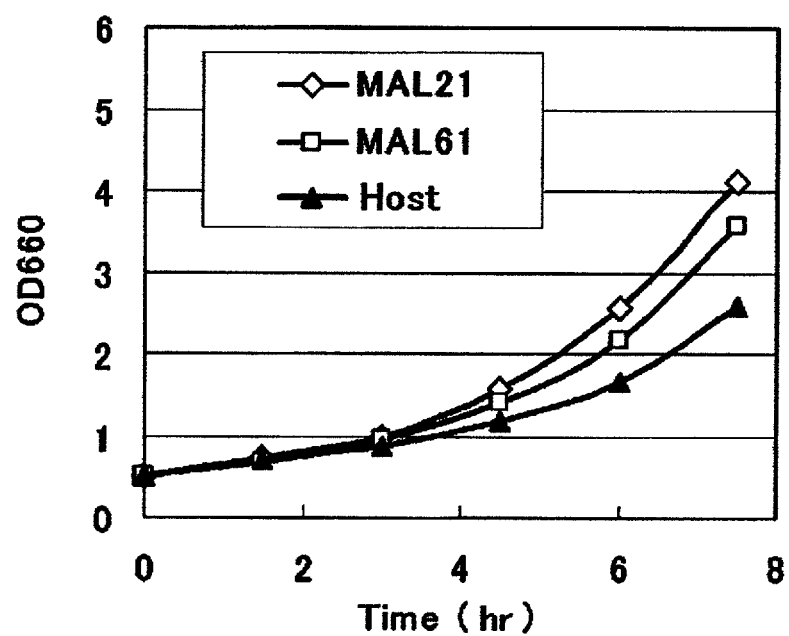
FIG. 12: Growth of MAL21 gene-highly expressed laboratory strains in maltose medium

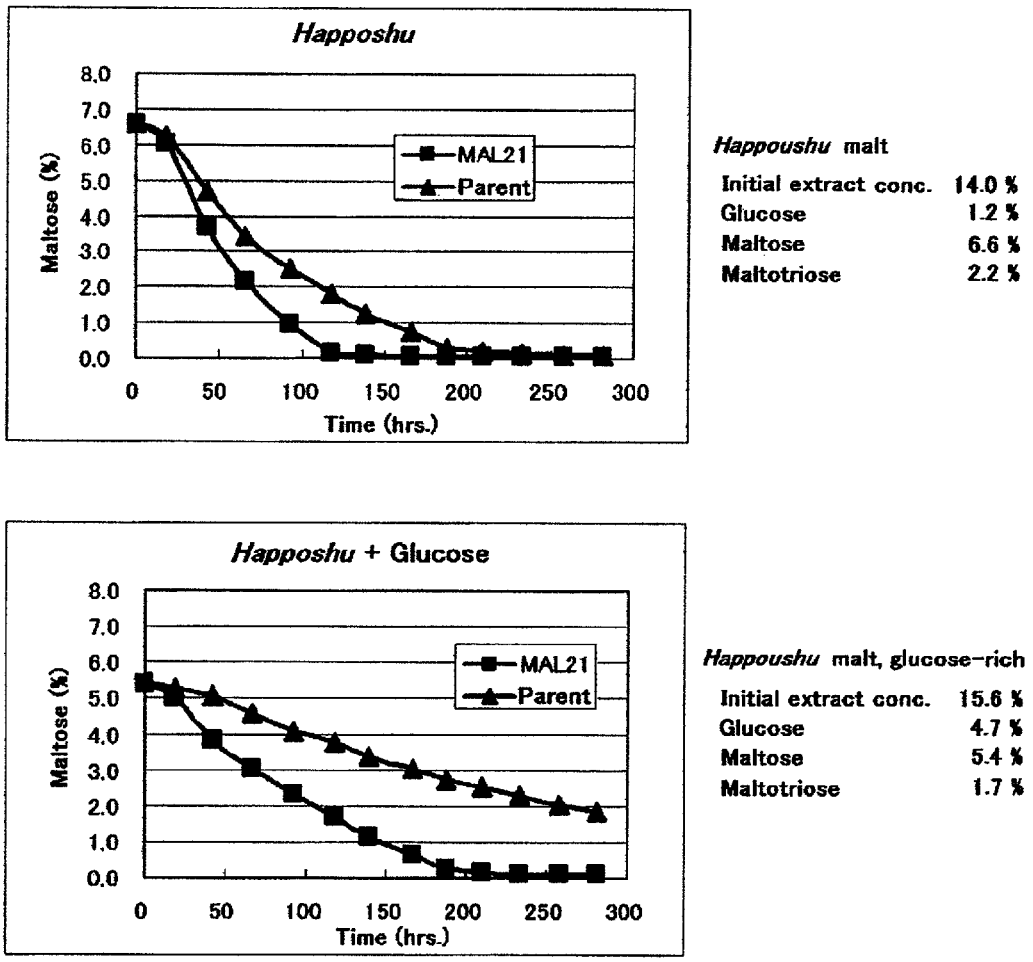
FIG. 13: Maltose fermentation rates of MAL21 gene-highly expressed bottom-fermenting beer yeast strains in *happoshu* (low-malt beer) or in *happoshu* (glucose-rich) wort

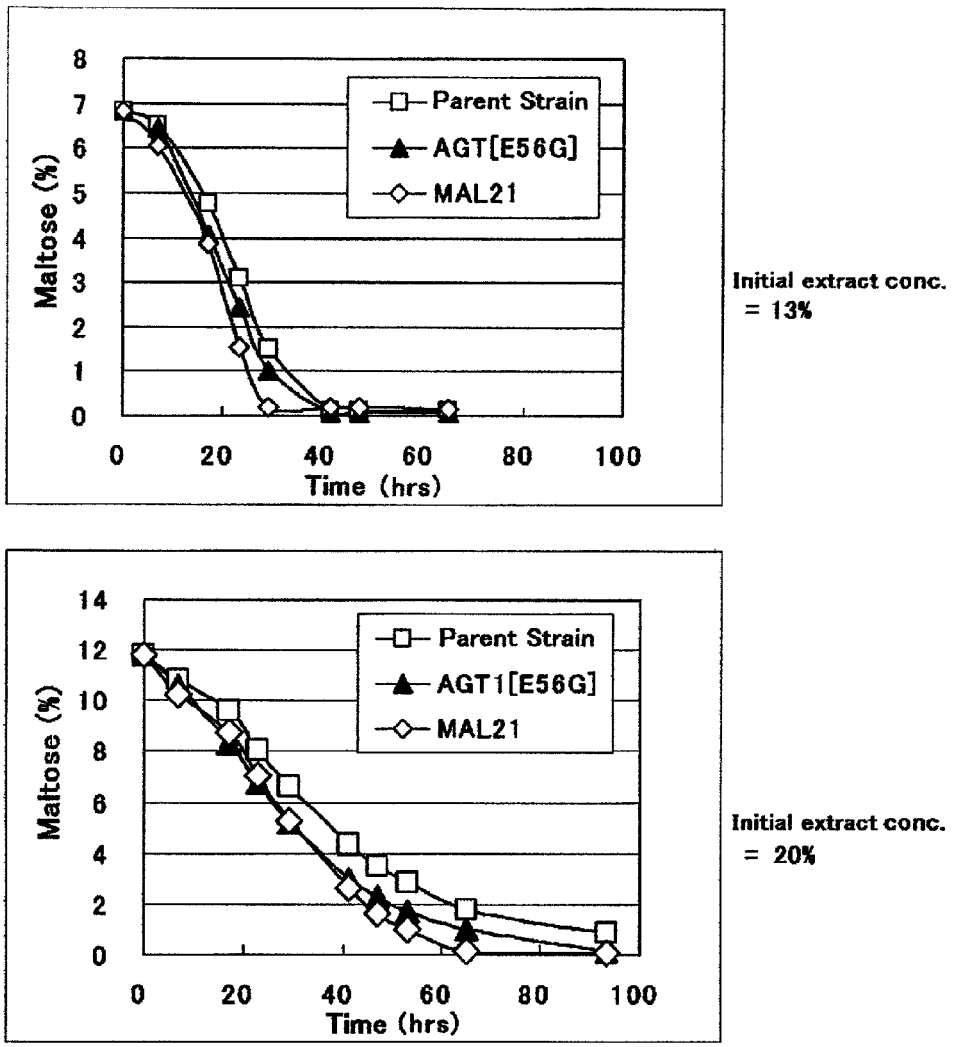
FIG. 14: Maltose fermentation rates in the wort of top-fermenting beer yeasts in which the transporter less susceptible to glucose-induced degradation is higly expressed.

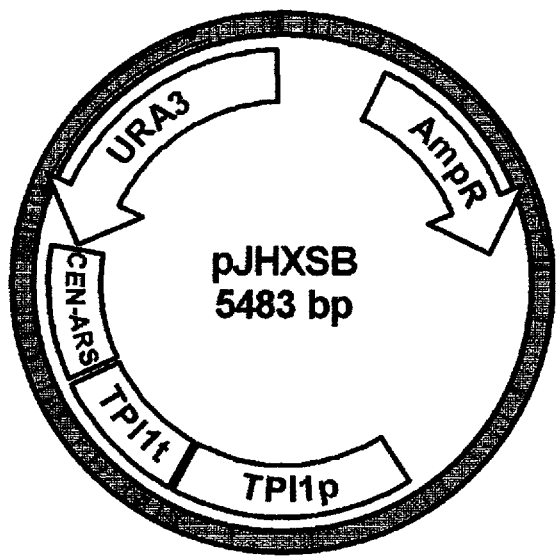
FIG. 15: Plasmid pJHXSB
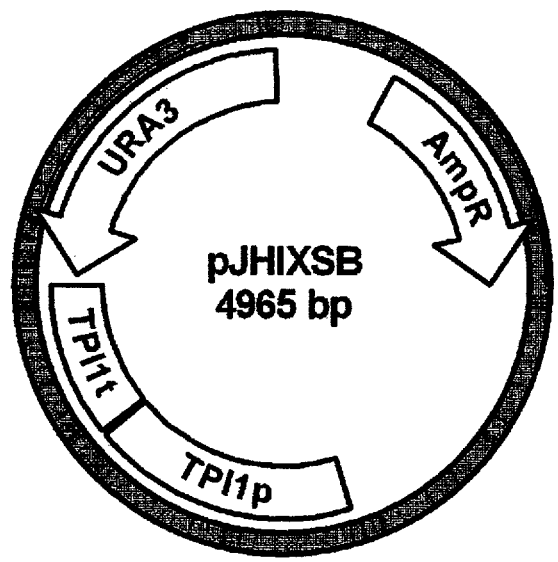
FIG. 16: Plasmid pJHIXSB

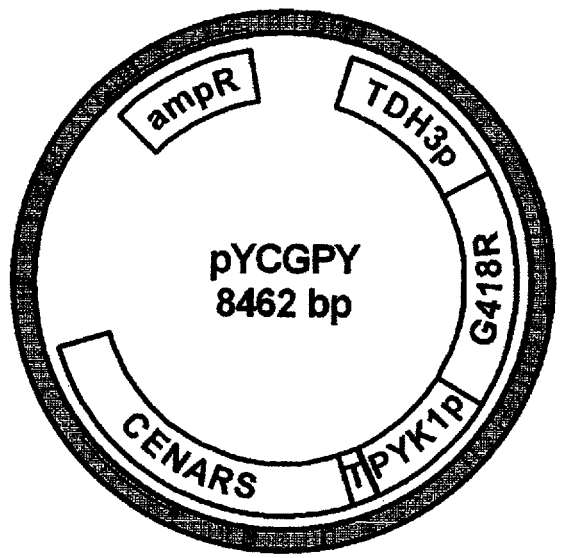
FIG. 17: Plasmid pYCGPY
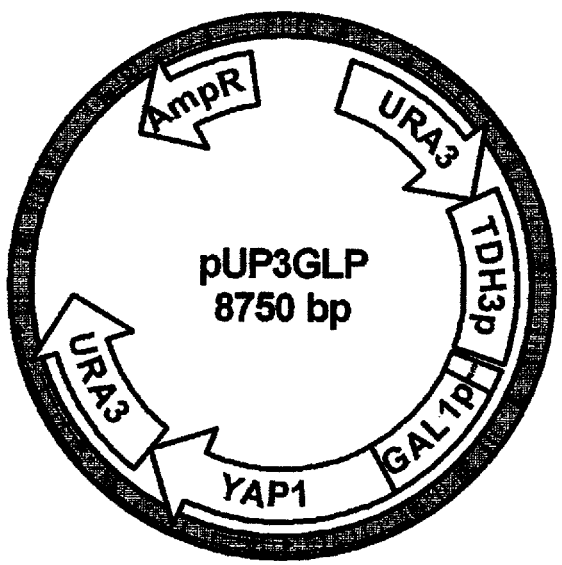
FIG. 18: Plasmid pUP3GLP

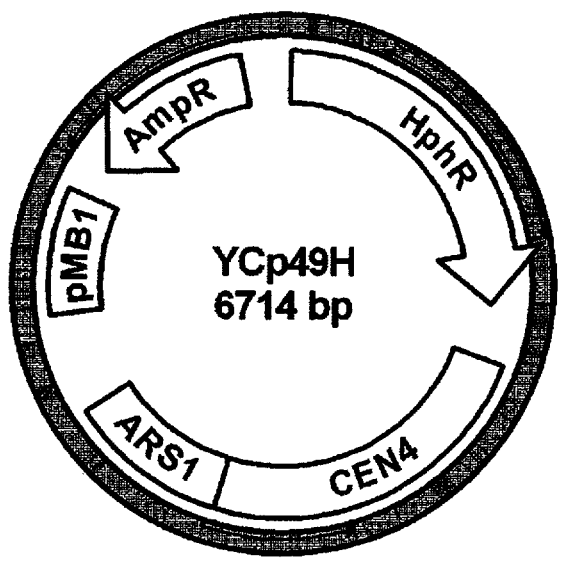
FIG. 19: Plasmid pYCp49H

SEQUENCE LISTING

```
<160> NUMBER OF SEQ ID NOS: 66

<210> SEQ ID NO 1
<211> LENGTH: 1842
<212> TYPE: DNA
<213> ORGANISM: Saccharomyces cerevisiae
<220> FEATURE:
<221> NAME/KEY: CDS
<222> LOCATION: (1)..(1842)
<223> OTHER INFORMATION: Mal21 Transporter Protein

<400> SEQUENCE: 1 atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
            20                  25                  30 tcg ata gag atg gag gag caa ggt aag aaa agt gat ttt ggt ctt tcc     144
Ser Ile Glu Met Glu Glu Gln Gly Lys Lys Ser Asp Phe Gly Leu Ser
        35                  40                  45 cat cat gag tac ggt cca ggt tca cta ata cca aac gat aat aat gaa     192
His His Glu Tyr Gly Pro Gly Ser Leu Ile Pro Asn Asp Asn Asn Glu
    50                  55                  60 gaa gtc ccc gac ctt ctc gat gaa gct atg cag gac gcc aaa gag gca     240
Glu Val Pro Asp Leu Leu Asp Glu Ala Met Gln Asp Ala Lys Glu Ala
65                  70                  75                  80 gat gaa agt gag agg gga atg cca ctc atg aca gct ttg aag aca tat     288
Asp Glu Ser Glu Arg Gly Met Pro Leu Met Thr Ala Leu Lys Thr Tyr
                85                  90                  95 cca aaa gct gct gct tgg tca cta tta gtt tcc aca aca ttg att caa     336
Pro Lys Ala Ala Ala Trp Ser Leu Leu Val Ser Thr Thr Leu Ile Gln
            100                 105                 110 gag ggt tat gac aca gcc att cta gga gct ttc tat gcc ctg cct gtt     384
Glu Gly Tyr Asp Thr Ala Ile Leu Gly Ala Phe Tyr Ala Leu Pro Val
        115                 120                 125 ttt caa aaa aaa tat ggt tct ttg aat agc aat aca gga gat tat gaa     432
Phe Gln Lys Lys Tyr Gly Ser Leu Asn Ser Asn Thr Gly Asp Tyr Glu
    130                 135                 140
```

```
att tca gtt tct tgg caa atc ggt cta tgt cta tgc tac atg gca ggt        480
Ile Ser Val Ser Trp Gln Ile Gly Leu Cys Leu Cys Tyr Met Ala Gly
145                 150                 155                 160 gaa att gtg ggg cta cag cta acg ggg ccc tcc gtg gat ctt gtt gga        528
Glu Ile Val Gly Leu Gln Leu Thr Gly Pro Ser Val Asp Leu Val Gly
                165                 170                 175 aat cgt tac aca ttg atc atg gcg ttg ttc ttt tta gcg gct ttc att        576
Asn Arg Tyr Thr Leu Ile Met Ala Leu Phe Phe Leu Ala Ala Phe Ile
            180                 185                 190 ttc att ctg tat ttt tgc aag agt ttg ggt atg att gcc gtg gga cag        624
Phe Ile Leu Tyr Phe Cys Lys Ser Leu Gly Met Ile Ala Val Gly Gln
        195                 200                 205 gca ttg tgt ggt atg cca tgg ggt tgt ttc caa tgt ttg acc gtt tct        672
Ala Leu Cys Gly Met Pro Trp Gly Cys Phe Gln Cys Leu Thr Val Ser
    210                 215                 220 tat gct tct gaa att tgt cct ttg gcc cta aga tac tat ttg acg act        720
Tyr Ala Ser Glu Ile Cys Pro Leu Ala Leu Arg Tyr Tyr Leu Thr Thr
225                 230                 235                 240 tat tct aat tta tgt tgg acg ttc ggt caa ctt ttc gct gct ggt att        768
Tyr Ser Asn Leu Cys Trp Thr Phe Gly Gln Leu Phe Ala Ala Gly Ile
                245                 250                 255 atg aaa aat tcc cag aac aaa tat gcc aac tca gaa cta gga tat aag        816
Met Lys Asn Ser Gln Asn Lys Tyr Ala Asn Ser Glu Leu Gly Tyr Lys
            260                 265                 270 cta cct ttt gct ttg cag tgg atc tgg ccc ctt cct ttg gcg gta ggt        864
Leu Pro Phe Ala Leu Gln Trp Ile Trp Pro Leu Pro Leu Ala Val Gly
        275                 280                 285 att ttt ttt gca cca gag tct cca tgg tgg ctg gtt aaa aaa gga agg        912
Ile Phe Phe Ala Pro Glu Ser Pro Trp Trp Leu Val Lys Lys Gly Arg
    290                 295                 300 att gat caa gcg agg aga tca ctt gaa aga aca tta agt ggt aaa gga        960
Ile Asp Gln Ala Arg Arg Ser Leu Glu Arg Thr Leu Ser Gly Lys Gly
305                 310                 315                 320 ccc gag aaa gaa tta cta gtg act atg gaa ctc gat aaa atc aaa act       1008
Pro Glu Lys Glu Leu Leu Val Thr Met Glu Leu Asp Lys Ile Lys Thr
                325                 330                 335 act ata gaa aag gag cag aaa atg tct gat gaa gga act tac tgg gat       1056
Thr Ile Glu Lys Glu Gln Lys Met Ser Asp Glu Gly Thr Tyr Trp Asp
            340                 345                 350 tgt gtg aaa gat ggt att aac agg aga aga acg aga ata gct tgt tta       1104
Cys Val Lys Asp Gly Ile Asn Arg Arg Arg Thr Arg Ile Ala Cys Leu
        355                 360                 365 tgt tgg atc ggt caa tgc tcc tgt ggt gca tca tta att ggt tat tca       1152
Cys Trp Ile Gly Gln Cys Ser Cys Gly Ala Ser Leu Ile Gly Tyr Ser
    370                 375                 380 act tac ttt tat gaa aaa gct ggt gtt agc act gat acg gct ttt act       1200
Thr Tyr Phe Tyr Glu Lys Ala Gly Val Ser Thr Asp Thr Ala Phe Thr
385                 390                 395                 400 ttc agt att atc caa tat tgt ctt ggt att gct gca acg ttt gta tcc       1248
Phe Ser Ile Ile Gln Tyr Cys Leu Gly Ile Ala Ala Thr Phe Val Ser
                405                 410                 415 tgg tgg gct tca aaa tat tgt ggc aga ttt gac ctt tat gct ttt ggg       1296
Trp Trp Ala Ser Lys Tyr Cys Gly Arg Phe Asp Leu Tyr Ala Phe Gly
            420                 425                 430 ctg gct ttt cag gct att atg ttc ttc att atc ggt ggt tta gga tgt       1344
Leu Ala Phe Gln Ala Ile Met Phe Phe Ile Ile Gly Gly Leu Gly Cys
        435                 440                 445 tca gac act cat ggc gct aaa atg ggt agt ggt gct ctt cta atg gtt       1392
Ser Asp Thr His Gly Ala Lys Met Gly Ser Gly Ala Leu Leu Met Val
    450                 455                 460
```

```
gtc gcg ttc ttt tac aac ctc ggt att gca cct gtt gtt ttt tgc tta     1440
Val Ala Phe Phe Tyr Asn Leu Gly Ile Ala Pro Val Val Phe Cys Leu
465                 470                 475                 480 gtg tct gaa atg ccg tct tca agg cta aga acc aaa aca att att ttg     1488
Val Ser Glu Met Pro Ser Ser Arg Leu Arg Thr Lys Thr Ile Ile Leu
                485                 490                 495 gct cgt aat gct tac aat gtg atc caa gtt gta gtt aca gtt ttg att     1536
Ala Arg Asn Ala Tyr Asn Val Ile Gln Val Val Val Thr Val Leu Ile
            500                 505                 510 atg tac caa ttg aac tca gag aaa tgg aat tgg ggt gct aaa tca ggc     1584
Met Tyr Gln Leu Asn Ser Glu Lys Trp Asn Trp Gly Ala Lys Ser Gly
        515                 520                 525 ttt ttc tgg gga gga ttt tgt ctg gcc act tta gct tgg gct gtt gtc     1632
Phe Phe Trp Gly Gly Phe Cys Leu Ala Thr Leu Ala Trp Ala Val Val
    530                 535                 540 gat tta cca gaa acc gct ggc agg act ttt att gag ata aat gaa ttg     1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac     1728
Phe Arg Leu Gly Val Pro Ala Arg Lys Phe Lys Ser Thr Lys Val Asp
                565                 570                 575 cct ttt gca gct gcc aaa gca gca gct gca gaa att aat gtt aaa gat     1776
Pro Phe Ala Ala Ala Lys Ala Ala Ala Glu Ile Asn Val Lys Asp
            580                 585                 590 ccg aag gaa gat ttg gaa act tct gtg gta gat gaa ggg cga aac acc     1824
Pro Lys Glu Asp Leu Glu Thr Ser Val Val Asp Glu Gly Arg Asn Thr
        595                 600                 605 tca tct gtt gtg aac aaa                                             1842
Ser Ser Val Val Asn Lys
    610
```

<210> SEQ ID NO 2
<211> LENGTH: 614
<212> TYPE: PRT
<213> ORGANISM: Saccharomyces cerevisiae

<400> SEQUENCE: 2

```
Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Gly Leu Ser
        35                  40                  45

His His Glu Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ala Phe Tyr Ala Leu Pro Val
        115                 120                 125

Phe Gln Lys Lys Tyr Gly Ser Leu Asn Ser Asn Thr Gly Asp Tyr Glu
    130                 135                 140

Ile Ser Val Ser Trp Gln Ile Gly Leu Cys Leu Cys Tyr Met Ala Gly
145                 150                 155                 160

Glu Ile Val Gly Leu Gln Leu Thr Gly Pro Ser Val Asp Leu Val Gly
```

-continued

```
                165                 170                 175
Asn Arg Tyr Thr Leu Ile Met Ala Leu Phe Phe Leu Ala Ala Phe Ile
                180                 185                 190
Phe Ile Leu Tyr Phe Cys Lys Ser Leu Gly Met Ile Ala Val Gly Gln
                195                 200                 205
Ala Leu Cys Gly Met Pro Trp Gly Cys Phe Gln Cys Leu Thr Val Ser
                210                 215                 220
Tyr Ala Ser Glu Ile Cys Pro Leu Ala Leu Arg Tyr Tyr Leu Thr Thr
225                 230                 235                 240
Tyr Ser Asn Leu Cys Trp Thr Phe Gly Gln Leu Phe Ala Ala Gly Ile
                245                 250                 255
Met Lys Asn Ser Gln Asn Lys Tyr Ala Asn Ser Glu Leu Gly Tyr Lys
                260                 265                 270
Leu Pro Phe Ala Leu Gln Trp Ile Trp Pro Leu Pro Leu Ala Val Gly
                275                 280                 285
Ile Phe Phe Ala Pro Glu Ser Pro Trp Trp Leu Val Lys Lys Gly Arg
                290                 295                 300
Ile Asp Gln Ala Arg Arg Ser Leu Glu Arg Thr Leu Ser Gly Lys Gly
305                 310                 315                 320
Pro Glu Lys Glu Leu Leu Val Thr Met Glu Leu Asp Lys Ile Lys Thr
                325                 330                 335
Thr Ile Glu Lys Glu Gln Lys Met Ser Asp Gly Thr Tyr Trp Asp
                340                 345                 350
Cys Val Lys Asp Gly Ile Asn Arg Arg Arg Thr Arg Ile Ala Cys Leu
                355                 360                 365
Cys Trp Ile Gly Gln Cys Ser Cys Gly Ala Ser Leu Ile Gly Tyr Ser
                370                 375                 380
Thr Tyr Phe Tyr Glu Lys Ala Gly Val Ser Thr Asp Thr Ala Phe Thr
385                 390                 395                 400
Phe Ser Ile Ile Gln Tyr Cys Leu Gly Ile Ala Ala Thr Phe Val Ser
                405                 410                 415
Trp Trp Ala Ser Lys Tyr Cys Gly Arg Phe Asp Leu Tyr Ala Phe Gly
                420                 425                 430
Leu Ala Phe Gln Ala Ile Met Phe Phe Ile Ile Gly Gly Leu Gly Cys
                435                 440                 445
Ser Asp Thr His Gly Ala Lys Met Gly Ser Gly Ala Leu Leu Met Val
                450                 455                 460
Val Ala Phe Phe Tyr Asn Leu Gly Ile Ala Pro Val Val Phe Cys Leu
465                 470                 475                 480
Val Ser Glu Met Pro Ser Ser Arg Leu Arg Thr Lys Thr Ile Ile Leu
                485                 490                 495
Ala Arg Asn Ala Tyr Asn Val Ile Gln Val Val Val Thr Val Leu Ile
                500                 505                 510
Met Tyr Gln Leu Asn Ser Glu Lys Trp Asn Trp Gly Ala Lys Ser Gly
                515                 520                 525
Phe Phe Trp Gly Gly Phe Cys Leu Ala Thr Leu Ala Trp Ala Val Val
                530                 535                 540
Asp Leu Pro Glu Thr Ala Gly Arg Thr Phe Ile Glu Ile Asn Glu Leu
545                 550                 555                 560
Phe Arg Leu Gly Val Pro Ala Arg Lys Phe Lys Ser Thr Lys Val Asp
                565                 570                 575
Pro Phe Ala Ala Lys Ala Ala Ala Glu Ile Asn Val Lys Asp
                580                 585                 590
```

```
Pro Lys Glu Asp Leu Glu Thr Ser Val Val Asp Glu Gly Arg Asn Thr
        595                 600                 605

Ser Ser Val Val Asn Lys
    610

<210> SEQ ID NO 3
<211> LENGTH: 1842
<212> TYPE: DNA
<213> ORGANISM: Saccharomyces cerevisiae
<220> FEATURE:
<221> NAME/KEY: CDS
<222> LOCATION: (1)..(1842)
<223> OTHER INFORMATION: Mal31 Transporter Protein

<400> SEQUENCE: 3 atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
            20                  25                  30 tcg ata gag atg gag gag caa ggt aag aaa agt gat ttt gat ctt tcc     144
Ser Ile Glu Met Glu Glu Gln Gly Lys Lys Ser Asp Phe Asp Leu Ser
        35                  40                  45 cat ctt gag tac ggt cca ggt tca cta ata cca aac gat aat aat gaa     192
His Leu Glu Tyr Gly Pro Gly Ser Leu Ile Pro Asn Asp Asn Asn Glu
    50                  55                  60 gaa gtc ccc gac ctt ctc gat gaa gct atg cag gac gcc aaa gag gca     240
Glu Val Pro Asp Leu Leu Asp Glu Ala Met Gln Asp Ala Lys Glu Ala
65                  70                  75                  80 gat gaa agt gag agg gga atg cca ctc atg aca gct ttg aag aca tat     288
Asp Glu Ser Glu Arg Gly Met Pro Leu Met Thr Ala Leu Lys Thr Tyr
                85                  90                  95 cca aaa gct gct gct tgg tca cta tta gtt tcc aca aca ttg att caa     336
Pro Lys Ala Ala Ala Trp Ser Leu Leu Val Ser Thr Thr Leu Ile Gln
            100                 105                 110 gag ggt tat gac aca gcc att cta gga gct ttc tat gcc ctg cct gtt     384
Glu Gly Tyr Asp Thr Ala Ile Leu Gly Ala Phe Tyr Ala Leu Pro Val
        115                 120                 125 ttt caa aaa aaa tat ggt tct ttg aat agc aat aca gga gat tat gaa     432
Phe Gln Lys Lys Tyr Gly Ser Leu Asn Ser Asn Thr Gly Asp Tyr Glu
    130                 135                 140 att tca gtt tcc tgg caa atc ggt cta tgt cta tgc tac atg gca ggt     480
Ile Ser Val Ser Trp Gln Ile Gly Leu Cys Leu Cys Tyr Met Ala Gly
145                 150                 155                 160 gag att gtc ggt ttg caa atg act ggg cct tct gta gat tac atg ggc     528
Glu Ile Val Gly Leu Gln Met Thr Gly Pro Ser Val Asp Tyr Met Gly
                165                 170                 175 aac cgt tac act ctg atc atg gcg ttg ttc ttt tta gcg gct ttc att     576
Asn Arg Tyr Thr Leu Ile Met Ala Leu Phe Phe Leu Ala Ala Phe Ile
            180                 185                 190 ttc att ctg tat ttt tgc aag agt ttg ggt atg att gcc gtg gga cag     624
Phe Ile Leu Tyr Phe Cys Lys Ser Leu Gly Met Ile Ala Val Gly Gln
        195                 200                 205 gca ttg tgt ggt atg cca tgg ggt tgt ttc caa tgt ttg acc gtt tct     672
Ala Leu Cys Gly Met Pro Trp Gly Cys Phe Gln Cys Leu Thr Val Ser
    210                 215                 220 tat gct tct gaa att tgt cct ttg gcc cta aga tac tat ttg acg act     720
Tyr Ala Ser Glu Ile Cys Pro Leu Ala Leu Arg Tyr Tyr Leu Thr Thr
225                 230                 235                 240 tat tct aat tta tgt tgg gcg ttc ggt caa ctt ttc gct gct ggt att     768
Tyr Ser Asn Leu Cys Trp Ala Phe Gly Gln Leu Phe Ala Ala Gly Ile
```

-continued

```
                     245                 250                 255
atg aaa aat tcc cag aac aaa tat gcc aac tca gaa cta gga tat aag    816
Met Lys Asn Ser Gln Asn Lys Tyr Ala Asn Ser Glu Leu Gly Tyr Lys
            260                 265                 270 cta cct ttt gct ttg cag tgg atc tgg ccc ctt cct ttg gcg gta ggt    864
Leu Pro Phe Ala Leu Gln Trp Ile Trp Pro Leu Pro Leu Ala Val Gly
        275                 280                 285 att ttt ttt gca cca gag tct cca tgg tgg ctg gtt aaa aaa gga agg    912
Ile Phe Phe Ala Pro Glu Ser Pro Trp Trp Leu Val Lys Lys Gly Arg
    290                 295                 300 att gat caa gcg agg aga tca ctt gaa aga aca tta agt ggt aaa gga    960
Ile Asp Gln Ala Arg Arg Ser Leu Glu Arg Thr Leu Ser Gly Lys Gly
305                 310                 315                 320 ccc gag aaa gaa tta cta gtg agt atg gaa ctc gat aaa atc aaa act   1008
Pro Glu Lys Glu Leu Leu Val Ser Met Glu Leu Asp Lys Ile Lys Thr
                325                 330                 335 act ata gaa aag gag cag aaa atg tct gat gaa gga act tac tgg gat   1056
Thr Ile Glu Lys Glu Gln Lys Met Ser Asp Glu Gly Thr Tyr Trp Asp
            340                 345                 350 tgt gtg aaa gat ggt att aac agg aga aga acg aga ata gct tgt tta   1104
Cys Val Lys Asp Gly Ile Asn Arg Arg Arg Thr Arg Ile Ala Cys Leu
        355                 360                 365 tgt tgg atc ggt caa tgc tcc tgt ggt gca tca tta att ggt tat tca   1152
Cys Trp Ile Gly Gln Cys Ser Cys Gly Ala Ser Leu Ile Gly Tyr Ser
    370                 375                 380 act tac ttt tat gaa aaa gct ggt gtt agc act gat acg gct ttt act   1200
Thr Tyr Phe Tyr Glu Lys Ala Gly Val Ser Thr Asp Thr Ala Phe Thr
385                 390                 395                 400 ttc agt att atc caa tat tgt ctt ggt att gct gca acg ttt ata tcc   1248
Phe Ser Ile Ile Gln Tyr Cys Leu Gly Ile Ala Ala Thr Phe Ile Ser
                405                 410                 415 tgg tgg gct tca aaa tat tgt ggc aga ttt gac ctt tat gct ttt ggg   1296
Trp Trp Ala Ser Lys Tyr Cys Gly Arg Phe Asp Leu Tyr Ala Phe Gly
            420                 425                 430 ctg gct ttt cag gct att atg ttc ttc att atc ggt ggt tta gga tgt   1344
Leu Ala Phe Gln Ala Ile Met Phe Phe Ile Ile Gly Gly Leu Gly Cys
        435                 440                 445 tca gac act cat ggc gct aaa atg ggt agt ggt gct ctt cta atg gtt   1392
Ser Asp Thr His Gly Ala Lys Met Gly Ser Gly Ala Leu Leu Met Val
    450                 455                 460 gtc gcg ttc ttt tac aac ctc ggt att gca cct gtt gtt ttt tgc tta   1440
Val Ala Phe Phe Tyr Asn Leu Gly Ile Ala Pro Val Val Phe Cys Leu
465                 470                 475                 480 gtg tct gaa ata ccg tct tca agg cta aga acc aaa aca att att ttg   1488
Val Ser Glu Ile Pro Ser Ser Arg Leu Arg Thr Lys Thr Ile Ile Leu
                485                 490                 495 gct cgt aat gct tac aat gtg atc caa gtt gta gtt aca gtt ttg atc   1536
Ala Arg Asn Ala Tyr Asn Val Ile Gln Val Val Val Thr Val Leu Ile
            500                 505                 510 atg tac caa ttg aac tca gag aaa tgg aat tgg ggt gct aaa tca ggc   1584
Met Tyr Gln Leu Asn Ser Glu Lys Trp Asn Trp Gly Ala Lys Ser Gly
        515                 520                 525 ttt ttc tgg gga gga ttt tgt ctg gcc act tta gct tgg gct gtt gtc   1632
Phe Phe Trp Gly Gly Phe Cys Leu Ala Thr Leu Ala Trp Ala Val Val
    530                 535                 540 gat tta cca gaa acc gct ggc agg act ttt att gag ata aat gaa ttg   1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac   1728
Phe Arg Leu Gly Val Pro Ala Arg Lys Phe Lys Ser Thr Lys Val Asp
```

```
                      565                 570                 575
cct ttt gca gct gcc aaa gca gca gct gca gaa att aat gtt aaa gat    1776
Pro Phe Ala Ala Ala Lys Ala Ala Ala Ala Glu Ile Asn Val Lys Asp
            580                 585                 590 ccg aag gaa gat ttg gaa act tct gtg gta gat gaa ggg cga aac acc    1824
Pro Lys Glu Asp Leu Glu Thr Ser Val Val Asp Glu Gly Arg Asn Thr
        595                 600                 605 tca tct gtt gtg aac aaa                                            1842
Ser Ser Val Val Asn Lys
        610

<210> SEQ ID NO 4
<211> LENGTH: 614
<212> TYPE: PRT
<213> ORGANISM: Saccharomyces cerevisiae

<400> SEQUENCE: 4

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Asp Leu Ser
        35                  40                  45

His Leu Glu Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ala Phe Tyr Ala Leu Pro Val
        115                 120                 125

Phe Gln Lys Lys Tyr Gly Ser Leu Asn Ser Asn Thr Gly Asp Tyr Glu
    130                 135                 140

Ile Ser Val Ser Trp Gln Ile Gly Leu Cys Leu Cys Tyr Met Ala Gly
145                 150                 155                 160

Glu Ile Val Gly Leu Gln Met Thr Gly Pro Ser Val Asp Tyr Met Gly
                165                 170                 175

Asn Arg Tyr Thr Leu Ile Met Ala Leu Phe Phe Leu Ala Ala Phe Ile
            180                 185                 190

Phe Ile Leu Tyr Phe Cys Lys Ser Leu Gly Met Ile Ala Val Gly Gln
        195                 200                 205

Ala Leu Cys Gly Met Pro Trp Gly Cys Phe Gln Cys Leu Thr Val Ser
    210                 215                 220

Tyr Ala Ser Glu Ile Cys Pro Leu Ala Leu Arg Tyr Tyr Leu Thr Thr
225                 230                 235                 240

Tyr Ser Asn Leu Cys Trp Ala Phe Gly Gln Leu Phe Ala Ala Gly Ile
                245                 250                 255

Met Lys Asn Ser Gln Asn Lys Tyr Ala Asn Ser Glu Leu Gly Tyr Lys
            260                 265                 270

Leu Pro Phe Ala Leu Gln Trp Ile Trp Pro Leu Pro Leu Ala Val Gly
        275                 280                 285

Ile Phe Phe Ala Pro Glu Ser Pro Trp Trp Leu Val Lys Lys Gly Arg
    290                 295                 300

Ile Asp Gln Ala Arg Arg Ser Leu Glu Arg Thr Leu Ser Gly Lys Gly
```

-continued

```
            305                 310                 315                 320
Pro Glu Lys Glu Leu Leu Val Ser Met Glu Leu Asp Lys Ile Lys Thr
                325                 330                 335

Thr Ile Glu Lys Glu Gln Lys Met Ser Asp Glu Gly Thr Tyr Trp Asp
                340                 345                 350

Cys Val Lys Asp Gly Ile Asn Arg Arg Thr Arg Ile Ala Cys Leu
            355                 360                 365

Cys Trp Ile Gly Gln Cys Ser Cys Gly Ala Ser Leu Ile Gly Tyr Ser
    370                 375                 380

Thr Tyr Phe Tyr Glu Lys Ala Gly Val Ser Thr Asp Thr Ala Phe Thr
385                 390                 395                 400

Phe Ser Ile Ile Gln Tyr Cys Leu Gly Ile Ala Ala Thr Phe Ile Ser
                405                 410                 415

Trp Trp Ala Ser Lys Tyr Cys Gly Arg Phe Asp Leu Tyr Ala Phe Gly
                420                 425                 430

Leu Ala Phe Gln Ala Ile Met Phe Phe Ile Ile Gly Gly Leu Gly Cys
            435                 440                 445

Ser Asp Thr His Gly Ala Lys Met Gly Ser Gly Ala Leu Leu Met Val
    450                 455                 460

Val Ala Phe Phe Tyr Asn Leu Gly Ile Ala Pro Val Val Phe Cys Leu
465                 470                 475                 480

Val Ser Glu Ile Pro Ser Ser Arg Leu Arg Thr Lys Thr Ile Ile Leu
                485                 490                 495

Ala Arg Asn Ala Tyr Asn Val Ile Gln Val Val Val Thr Val Leu Ile
            500                 505                 510

Met Tyr Gln Leu Asn Ser Glu Lys Trp Asn Trp Gly Ala Lys Ser Gly
    515                 520                 525

Phe Phe Trp Gly Gly Phe Cys Leu Ala Thr Leu Ala Trp Ala Val Val
530                 535                 540

Asp Leu Pro Glu Thr Ala Gly Arg Thr Phe Ile Glu Ile Asn Glu Leu
545                 550                 555                 560

Phe Arg Leu Gly Val Pro Ala Arg Lys Phe Lys Ser Thr Lys Val Asp
                565                 570                 575

Pro Phe Ala Ala Ala Lys Ala Ala Ala Glu Ile Asn Val Lys Asp
            580                 585                 590

Pro Lys Glu Asp Leu Glu Thr Ser Val Val Asp Glu Gly Arg Asn Thr
    595                 600                 605

Ser Ser Val Val Asn Lys
    610
```

<210> SEQ ID NO 5
<211> LENGTH: 1842
<212> TYPE: DNA
<213> ORGANISM: Saccharomyces cerevisiae
<220> FEATURE:
<221> NAME/KEY: CDS
<222> LOCATION: (1)..(1842)
<223> OTHER INFORMATION: Mal61 Transporter Protein

<400> SEQUENCE: 5

```
atg aag gga tta tcc tca tta ata aac aga aaa aaa gac agg aac gac    48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac    96
Ser His Leu Asp Glu Ile Glu Asn Gly Val Asn Ala Thr Glu Phe Asn
                20                  25                  30 tcg ata gag atg gag gag caa ggt aag aaa agt gat ttt gat ctt tcc   144
```

-continued

```
Ser Ile Glu Met Glu Glu Gln Gly Lys Lys Ser Asp Phe Asp Leu Ser
        35                  40                  45 cat ctt gag tac ggt cca ggt tca cta ata cca aac gat aat aat gaa      192
His Leu Glu Tyr Gly Pro Gly Ser Leu Ile Pro Asn Asp Asn Asn Glu
 50                  55                  60 gaa gtc ccc gac ctt ctc gat gaa gct atg cag gac gcc aaa gag gca      240
Glu Val Pro Asp Leu Leu Asp Glu Ala Met Gln Asp Ala Lys Glu Ala
 65                  70                  75                  80 gat gaa agt gag agg gga atg cca ctc atg aca gct ttg aag aca tat      288
Asp Glu Ser Glu Arg Gly Met Pro Leu Met Thr Ala Leu Lys Thr Tyr
                 85                  90                  95 cca aaa gct gct gct tgg tca cta tta gtt tcc aca aca ttg att caa      336
Pro Lys Ala Ala Ala Trp Ser Leu Leu Val Ser Thr Thr Leu Ile Gln
            100                 105                 110 gag ggt tat gac aca gcc att cta gga gct ttc tat gcc ctg cct gtt      384
Glu Gly Tyr Asp Thr Ala Ile Leu Gly Ala Phe Tyr Ala Leu Pro Val
        115                 120                 125 ttt caa aaa aaa tat ggt tct ttg aat agc aat aca gga gat tat gaa      432
Phe Gln Lys Lys Tyr Gly Ser Leu Asn Ser Asn Thr Gly Asp Tyr Glu
130                 135                 140 att tca gtt tcc tgg caa atc ggt cta tgt cta tgc tac atg gca ggt      480
Ile Ser Val Ser Trp Gln Ile Gly Leu Cys Leu Cys Tyr Met Ala Gly
145                 150                 155                 160 gag att gtc ggt ttg caa gtg act ggg cct tct gta gat tac atg ggc      528
Glu Ile Val Gly Leu Gln Val Thr Gly Pro Ser Val Asp Tyr Met Gly
                165                 170                 175 aac cgt tac act ctg atc atg gcg ttg ttt tta gcg gct ttc att         576
Asn Arg Tyr Thr Leu Ile Met Ala Leu Phe Phe Leu Ala Ala Phe Ile
            180                 185                 190 ttc att ctg tat ttt tgc aag agt ttg ggt atg att gcc gtg gga cag      624
Phe Ile Leu Tyr Phe Cys Lys Ser Leu Gly Met Ile Ala Val Gly Gln
        195                 200                 205 gca ttg tgt ggt atg cca tgg ggt tgt ttc caa tgt ttg acc gtt tct      672
Ala Leu Cys Gly Met Pro Trp Gly Cys Phe Gln Cys Leu Thr Val Ser
210                 215                 220 tat gct tct gaa att tgt cct ttg gcc cta aga tac tat ttg acg act      720
Tyr Ala Ser Glu Ile Cys Pro Leu Ala Leu Arg Tyr Tyr Leu Thr Thr
225                 230                 235                 240 tat tct aat tta tgt tgg acg ttc ggt caa ctt ttc gct gct ggt att      768
Tyr Ser Asn Leu Cys Trp Thr Phe Gly Gln Leu Phe Ala Ala Gly Ile
                245                 250                 255 atg aaa aat tcc cag aac aaa tat gcc aac tca gaa cta gga tat aag      816
Met Lys Asn Ser Gln Asn Lys Tyr Ala Asn Ser Glu Leu Gly Tyr Lys
            260                 265                 270 cta cct ttt gct ttg cag tgg atc tgg ccc ctt cct ttg gcg gta ggt      864
Leu Pro Phe Ala Leu Gln Trp Ile Trp Pro Leu Pro Leu Ala Val Gly
        275                 280                 285 att ttt ttg gca cca gag tct cca tgg tgg ctg gtt aaa aaa gga agg      912
Ile Phe Leu Ala Pro Glu Ser Pro Trp Trp Leu Val Lys Lys Gly Arg
        290                 295                 300 att gat cag gcg agg aga tca ctt gaa aga ata tta agt ggt aaa gga      960
Ile Asp Gln Ala Arg Arg Ser Leu Glu Arg Ile Leu Ser Gly Lys Gly
305                 310                 315                 320 ccc gag aaa gaa tta cta gtg agt atg gaa ctc gat aaa atc aaa act     1008
Pro Glu Lys Glu Leu Leu Val Ser Met Glu Leu Asp Lys Ile Lys Thr
                325                 330                 335 act ata gaa aag gag cag aaa atg tct gat gaa gga act tac tgg gat     1056
Thr Ile Glu Lys Glu Gln Lys Met Ser Asp Glu Gly Thr Tyr Trp Asp
            340                 345                 350 tgt gtg aaa gat ggt att aac agg aga aga acg aga ata gct tgt tta     1104
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Cys | Val | Lys | Asp | Gly | Ile | Asn | Arg | Arg | Thr | Arg | Ile | Ala | Cys | Leu |      |
|     | 355 |     |     |     | 360 |     |     |     |     | 365 |     |     |     |     |      |

```
tgt tgg atc ggt caa tgc tcc tgt ggt gca tca tta att ggt tat tca   1152
Cys Trp Ile Gly Gln Cys Ser Cys Gly Ala Ser Leu Ile Gly Tyr Ser
370             375                 380 act tac ttt tat gaa aaa gct ggt gtt agc act gat acg gct ttt act   1200
Thr Tyr Phe Tyr Glu Lys Ala Gly Val Ser Thr Asp Thr Ala Phe Thr
385             390                 395                 400 ttc agt att atc caa tat tgt ctt ggt att gct gca acg ttt gta tcc   1248
Phe Ser Ile Ile Gln Tyr Cys Leu Gly Ile Ala Ala Thr Phe Val Ser
            405                 410                 415 tgg tgg gct tca aaa tat tgt ggc aga ttt gac ctt tat gct ttt ggg   1296
Trp Trp Ala Ser Lys Tyr Cys Gly Arg Phe Asp Leu Tyr Ala Phe Gly
        420                 425                 430 ctg gct ttt cag gct att atg ttc ttc att atc ggt ggt tta gga tgt   1344
Leu Ala Phe Gln Ala Ile Met Phe Phe Ile Ile Gly Gly Leu Gly Cys
    435                 440                 445 tca gac act cat ggc gct aaa atg ggt agt ggt gct ctt cta atg gtt   1392
Ser Asp Thr His Gly Ala Lys Met Gly Ser Gly Ala Leu Leu Met Val
450                 455                 460 gtc gcg ttc ttt tac aac ctc ggt att gca cct gtt gtt ttt tgc tta   1440
Val Ala Phe Phe Tyr Asn Leu Gly Ile Ala Pro Val Val Phe Cys Leu
465                 470                 475                 480 gtg tct gaa atg ccg tct tca agg cta aga acc aaa aca att att ttg   1488
Val Ser Glu Met Pro Ser Ser Arg Leu Arg Thr Lys Thr Ile Ile Leu
            485                 490                 495 gct cgt aat gct tac aat gtg atc caa gtt gta gtt aca gtt ttg atc   1536
Ala Arg Asn Ala Tyr Asn Val Ile Gln Val Val Val Thr Val Leu Ile
        500                 505                 510 atg tac caa ttg aac tca gag aaa tgg aat tgg ggt gct aaa tca ggc   1584
Met Tyr Gln Leu Asn Ser Glu Lys Trp Asn Trp Gly Ala Lys Ser Gly
    515                 520                 525 ttt ttc tgg gga gga ttt tgt ctg gcc act tta gct tgg gct gtt gtc   1632
Phe Phe Trp Gly Gly Phe Cys Leu Ala Thr Leu Ala Trp Ala Val Val
530                 535                 540 gat tta cca gaa acc gct ggc agg act ttt att gag ata aat gaa ttg   1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac   1728
Phe Arg Leu Gly Val Pro Ala Arg Lys Phe Lys Ser Thr Lys Val Asp
            565                 570                 575 cct ttt gca gct gcc aaa gca gca gct gca gaa att aat gtt aaa gat   1776
Pro Phe Ala Ala Ala Lys Ala Ala Ala Ala Glu Ile Asn Val Lys Asp
        580                 585                 590 ccg aag gaa gat ttg gaa act tct gtg gta gat gaa ggg cga agc acc   1824
Pro Lys Glu Asp Leu Glu Thr Ser Val Val Asp Glu Gly Arg Ser Thr
    595                 600                 605 cca tct gtt gtg aac aaa                                           1842
Pro Ser Val Val Asn Lys
    610

<210> SEQ ID NO 6
<211> LENGTH: 614
<212> TYPE: PRT
<213> ORGANISM: Saccharomyces cerevisiae

<400> SEQUENCE: 6

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30
```

```
Ser Ile Glu Met Glu Glu Gln Gly Lys Lys Ser Asp Phe Asp Leu Ser
        35                  40                  45
His Leu Glu Tyr Gly Pro Gly Ser Leu Ile Pro Asn Asp Asn Asn Glu
    50                  55                  60
Glu Val Pro Asp Leu Leu Asp Glu Ala Met Gln Asp Ala Lys Glu Ala
65                  70                  75                  80
Asp Glu Ser Glu Arg Gly Met Pro Leu Met Thr Ala Leu Lys Thr Tyr
                85                  90                  95
Pro Lys Ala Ala Ala Trp Ser Leu Leu Val Ser Thr Thr Leu Ile Gln
            100                 105                 110
Glu Gly Tyr Asp Thr Ala Ile Leu Gly Ala Phe Tyr Ala Leu Pro Val
            115                 120                 125
Phe Gln Lys Lys Tyr Gly Ser Leu Asn Ser Asn Thr Gly Asp Tyr Glu
        130                 135                 140
Ile Ser Val Ser Trp Gln Ile Gly Leu Cys Leu Cys Tyr Met Ala Gly
145                 150                 155                 160
Glu Ile Val Gly Leu Gln Val Thr Gly Pro Ser Val Asp Tyr Met Gly
                165                 170                 175
Asn Arg Tyr Thr Leu Ile Met Ala Leu Phe Phe Leu Ala Ala Phe Ile
            180                 185                 190
Phe Ile Leu Tyr Phe Cys Lys Ser Leu Gly Met Ile Ala Val Gly Gln
        195                 200                 205
Ala Leu Cys Gly Met Pro Trp Gly Cys Phe Gln Cys Leu Thr Val Ser
    210                 215                 220
Tyr Ala Ser Glu Ile Cys Pro Leu Ala Leu Arg Tyr Tyr Leu Thr Thr
225                 230                 235                 240
Tyr Ser Asn Leu Cys Trp Thr Phe Gly Gln Leu Phe Ala Ala Gly Ile
                245                 250                 255
Met Lys Asn Ser Gln Asn Lys Tyr Ala Asn Ser Glu Leu Gly Tyr Lys
            260                 265                 270
Leu Pro Phe Ala Leu Gln Trp Ile Trp Pro Leu Pro Leu Ala Val Gly
        275                 280                 285
Ile Phe Leu Ala Pro Glu Ser Pro Trp Trp Leu Val Lys Lys Gly Arg
    290                 295                 300
Ile Asp Gln Ala Arg Arg Ser Leu Glu Arg Ile Leu Ser Gly Lys Gly
305                 310                 315                 320
Pro Glu Lys Glu Leu Leu Val Ser Met Glu Leu Asp Lys Ile Lys Thr
                325                 330                 335
Thr Ile Glu Lys Glu Gln Lys Met Ser Asp Glu Gly Thr Tyr Trp Asp
            340                 345                 350
Cys Val Lys Asp Gly Ile Asn Arg Arg Thr Arg Ile Ala Cys Leu
        355                 360                 365
Cys Trp Ile Gly Gln Cys Ser Cys Gly Ala Ser Leu Ile Gly Tyr Ser
    370                 375                 380
Thr Tyr Phe Tyr Glu Lys Ala Gly Val Ser Thr Asp Thr Ala Phe Thr
385                 390                 395                 400
Phe Ser Ile Ile Gln Tyr Cys Leu Gly Ile Ala Ala Thr Phe Val Ser
                405                 410                 415
Trp Trp Ala Ser Lys Tyr Cys Gly Arg Phe Asp Leu Tyr Ala Phe Gly
            420                 425                 430
Leu Ala Phe Gln Ala Ile Met Phe Phe Ile Ile Gly Gly Leu Gly Cys
        435                 440                 445
Ser Asp Thr His Gly Ala Lys Met Gly Ser Gly Ala Leu Leu Met Val
```

```
                450             455             460
Val Ala Phe Phe Tyr Asn Leu Gly Ile Ala Pro Val Val Phe Cys Leu
465                 470                 475                 480

Val Ser Glu Met Pro Ser Ser Arg Leu Arg Thr Lys Thr Ile Ile Leu
                485                 490                 495

Ala Arg Asn Ala Tyr Asn Val Ile Gln Val Val Thr Val Leu Ile
                500                 505                 510

Met Tyr Gln Leu Asn Ser Glu Lys Trp Asn Trp Gly Ala Lys Ser Gly
                515                 520                 525

Phe Phe Trp Gly Gly Phe Cys Leu Ala Thr Leu Ala Trp Ala Val Val
530                 535                 540

Asp Leu Pro Glu Thr Ala Gly Arg Thr Phe Ile Glu Ile Asn Glu Leu
545                 550                 555                 560

Phe Arg Leu Gly Val Pro Ala Arg Lys Phe Lys Ser Thr Lys Val Asp
                565                 570                 575

Pro Phe Ala Ala Lys Ala Ala Ala Glu Ile Asn Val Lys Asp
                580                 585                 590

Pro Lys Glu Asp Leu Glu Thr Ser Val Val Asp Glu Gly Arg Ser Thr
                595                 600                 605

Pro Ser Val Val Asn Lys
                610

<210> SEQ ID NO 7
<211> LENGTH: 1845
<212> TYPE: DNA
<213> ORGANISM: Saccharomyces cerevisiae
<220> FEATURE:
<221> NAME/KEY: CDS
<222> LOCATION: (1)..(1845)
<223> OTHER INFORMATION: Mtt1 Transporter Protein

<400> SEQUENCE: 7 atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
                20                  25                  30 tcg ata gag atg gag gag caa ggt aag aaa agt gat ttt gat ctt tcc     144
Ser Ile Glu Met Glu Glu Gln Gly Lys Lys Ser Asp Phe Asp Leu Ser
            35                  40                  45 cat cat gag tac ggt cca ggt tca cta aca cca aac gat aat aat gaa     192
His His Glu Tyr Gly Pro Gly Ser Leu Thr Pro Asn Asp Asn Asn Glu
        50                  55                  60 gaa gtc ccc gac ctt ctc gat gaa gct atg cag gac gcc aaa gag gca     240
Glu Val Pro Asp Leu Leu Asp Glu Ala Met Gln Asp Ala Lys Glu Ala
65                  70                  75                  80 gat gaa agt gag agg gga atg cca ctc atg aca gct ttg aag aca tat     288
Asp Glu Ser Glu Arg Gly Met Pro Leu Met Thr Ala Leu Lys Thr Tyr
                85                  90                  95 cca aaa gct gct gct tgg tca cta tta gtt tcc aca aca ttg att caa     336
Pro Lys Ala Ala Ala Trp Ser Leu Leu Val Ser Thr Thr Leu Ile Gln
            100                 105                 110 gag ggt tat gac aca gcc att cta gga tct ttc tat gcc ctg cct gtt     384
Glu Gly Tyr Asp Thr Ala Ile Leu Gly Ser Phe Tyr Ala Leu Pro Val
        115                 120                 125 ttt caa aaa aaa tat ggt tct ttg aat agc aat aca gga gat tat gaa     432
Phe Gln Lys Lys Tyr Gly Ser Leu Asn Ser Asn Thr Gly Asp Tyr Glu
    130                 135                 140
```

```
att tca gct tcc tgg caa att ggc ttg tcc tta tgc gtt acg gct ggt        480
Ile Ser Ala Ser Trp Gln Ile Gly Leu Ser Leu Cys Val Thr Ala Gly
145                 150                 155                 160 gaa att gta ggt ttg caa atg act ggg cct ttt gta gat tat atg ggt        528
Glu Ile Val Gly Leu Gln Met Thr Gly Pro Phe Val Asp Tyr Met Gly
                165                 170                 175 aat cgc tat aca ttg att ttg gca ttg att ctt ctt gct gca ttc acc        576
Asn Arg Tyr Thr Leu Ile Leu Ala Leu Ile Leu Leu Ala Ala Phe Thr
            180                 185                 190 ttt att ctg tat ttt tgc aag ggt ttg ggt atg att gct gtg gga caa        624
Phe Ile Leu Tyr Phe Cys Lys Gly Leu Gly Met Ile Ala Val Gly Gln
        195                 200                 205 gta ttg tgt ggt atg cca tgg ggt tgt ttc caa tgt ttg acc gtt tct        672
Val Leu Cys Gly Met Pro Trp Gly Cys Phe Gln Cys Leu Thr Val Ser
    210                 215                 220 tat gct tct gaa att tgt cct atg gcc cta aga tac tat ttg acg act        720
Tyr Ala Ser Glu Ile Cys Pro Met Ala Leu Arg Tyr Tyr Leu Thr Thr
225                 230                 235                 240 tat tct aat tta tgt tgg acg ttc ggt caa ctt ttc gct gct ggt att        768
Tyr Ser Asn Leu Cys Trp Thr Phe Gly Gln Leu Phe Ala Ala Gly Ile
                245                 250                 255 atg aaa aac tcc caa aat aag tac cct aac tca gaa cta gga tat aag        816
Met Lys Asn Ser Gln Asn Lys Tyr Pro Asn Ser Glu Leu Gly Tyr Lys
            260                 265                 270 cta cct ttt gct ttg cag tgg atc tgg cct gct cct ctt gca ata ggt        864
Leu Pro Phe Ala Leu Gln Trp Ile Trp Pro Ala Pro Leu Ala Ile Gly
        275                 280                 285 att ttt ttt gca cca gag tct cca tgg tgg ctg gtt aaa aaa gga agg        912
Ile Phe Phe Ala Pro Glu Ser Pro Trp Trp Leu Val Lys Lys Gly Arg
    290                 295                 300 att gat caa gca agg aga tca ctt gaa aga aca ttg agt ggt aaa gga        960
Ile Asp Gln Ala Arg Arg Ser Leu Glu Arg Thr Leu Ser Gly Lys Gly
305                 310                 315                 320 ccc gag aag gaa tta ctg gta agt atg gag cta gat aat atc aaa gta       1008
Pro Glu Lys Glu Leu Leu Val Ser Met Glu Leu Asp Asn Ile Lys Val
                325                 330                 335 acc att gaa aag gaa aaa aag ctg tca gac tca gaa ggt tcc tat tgg       1056
Thr Ile Glu Lys Glu Lys Lys Leu Ser Asp Ser Glu Gly Ser Tyr Trp
            340                 345                 350 gat tgt ctg aag gac agt gtt aat agg aga aga acg aga ata gct tgt       1104
Asp Cys Leu Lys Asp Ser Val Asn Arg Arg Arg Thr Arg Ile Ala Cys
        355                 360                 365 tta tgt tgg gtc ggt caa acc acc tgt ggt aca tca tta att ggt aat       1152
Leu Cys Trp Val Gly Gln Thr Thr Cys Gly Thr Ser Leu Ile Gly Asn
    370                 375                 380 tca act tac ttt tat gaa aaa gct gga gtt ggt act gat acg gct ttc       1200
Ser Thr Tyr Phe Tyr Glu Lys Ala Gly Val Gly Thr Asp Thr Ala Phe
385                 390                 395                 400 act ttc agt att atc caa tat tgt ctt ggt att gcc gca aca ttt ctt       1248
Thr Phe Ser Ile Ile Gln Tyr Cys Leu Gly Ile Ala Ala Thr Phe Leu
                405                 410                 415 tct tgg tgg gct tca aaa tat ttt ggt agg ttt gac ctt tac gca ttt       1296
Ser Trp Trp Ala Ser Lys Tyr Phe Gly Arg Phe Asp Leu Tyr Ala Phe
            420                 425                 430 gga ttg gct ata caa aca gtt tca ttg ttt atc ata gga ggt ttg gga       1344
Gly Leu Ala Ile Gln Thr Val Ser Leu Phe Ile Ile Gly Gly Leu Gly
        435                 440                 445 tgc tcc gac tcg cat ggc gct gaa atg gga agt ggt tct ctt tta atg       1392
Cys Ser Asp Ser His Gly Ala Glu Met Gly Ser Gly Ser Leu Leu Met
    450                 455                 460
```

```
gtt ctt tcc ttc ttc tac aat ttg ggt att gct ccc gtt gtg ttt tgc    1440
Val Leu Ser Phe Phe Tyr Asn Leu Gly Ile Ala Pro Val Val Phe Cys
465                 470                 475                 480 tta gtg tcc gaa ata cca tcc tca agg cta aga act aaa tcg att att    1488
Leu Val Ser Glu Ile Pro Ser Ser Arg Leu Arg Thr Lys Ser Ile Ile
                485                 490                 495 ctg gct cgt aac gca tat aat atg gca tct att gta act act gtt ttg    1536
Leu Ala Arg Asn Ala Tyr Asn Met Ala Ser Ile Val Thr Thr Val Leu
            500                 505                 510 atc atg tac caa ttg aac tca gaa aaa tgg aac tgg ggt gcc aag tcg    1584
Ile Met Tyr Gln Leu Asn Ser Glu Lys Trp Asn Trp Gly Ala Lys Ser
        515                 520                 525 ggc ttt ttc tgg gga ggg tta tgt ttt gcc act cta gtt tgg gcc gta    1632
Gly Phe Phe Trp Gly Gly Leu Cys Phe Ala Thr Leu Val Trp Ala Val
    530                 535                 540 att gac cta cca gaa act gct ggc agg act ttt att gag ata aat gaa    1680
Ile Asp Leu Pro Glu Thr Ala Gly Arg Thr Phe Ile Glu Ile Asn Glu
545                 550                 555                 560 ttg ttt aga ctt ggt gtt cca gca aga aag ttc aag tcg act aaa gtc    1728
Leu Phe Arg Leu Gly Val Pro Ala Arg Lys Phe Lys Ser Thr Lys Val
                565                 570                 575 gac cct ttt gca gct gcc aaa gca gca gct gca gaa att aat gtt aaa    1776
Asp Pro Phe Ala Ala Ala Lys Ala Ala Ala Ala Glu Ile Asn Val Lys
            580                 585                 590 gat ccg aag gaa gat ttg gaa act tct gtg gta gat gaa ggg cga agc    1824
Asp Pro Lys Glu Asp Leu Glu Thr Ser Val Val Asp Glu Gly Arg Ser
        595                 600                 605 acc cca tct gtt gtg aac aaa                                        1845
Thr Pro Ser Val Val Asn Lys
    610                 615

<210> SEQ ID NO 8
<211> LENGTH: 615
<212> TYPE: PRT
<213> ORGANISM: Saccharomyces cerevisiae

<400> SEQUENCE: 8

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Asp Leu Ser
        35                  40                  45

His His Glu Tyr Gly Pro Gly Ser Leu Thr Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ser Phe Tyr Ala Leu Pro Val
        115                 120                 125

Phe Gln Lys Lys Tyr Gly Ser Leu Asn Ser Asn Thr Gly Asp Tyr Glu
    130                 135                 140

Ile Ser Ala Ser Trp Gln Ile Gly Leu Ser Leu Cys Val Thr Ala Gly
145                 150                 155                 160

Glu Ile Val Gly Leu Gln Met Thr Gly Pro Phe Val Asp Tyr Met Gly
                165                 170                 175
```

-continued

```
Asn Arg Tyr Thr Leu Ile Leu Ala Leu Ile Leu Ala Ala Phe Thr
                180                 185                 190

Phe Ile Leu Tyr Phe Cys Lys Gly Leu Gly Met Ile Ala Val Gly Gln
        195                 200                 205

Val Leu Cys Gly Met Pro Trp Gly Cys Phe Gln Cys Leu Thr Val Ser
    210                 215                 220

Tyr Ala Ser Glu Ile Cys Pro Met Ala Leu Arg Tyr Tyr Leu Thr Thr
225                 230                 235                 240

Tyr Ser Asn Leu Cys Trp Thr Phe Gly Gln Leu Phe Ala Ala Gly Ile
                245                 250                 255

Met Lys Asn Ser Gln Asn Lys Tyr Pro Asn Ser Glu Leu Gly Tyr Lys
            260                 265                 270

Leu Pro Phe Ala Leu Gln Trp Ile Trp Pro Ala Pro Leu Ala Ile Gly
        275                 280                 285

Ile Phe Phe Ala Pro Glu Ser Pro Trp Trp Leu Val Lys Lys Gly Arg
    290                 295                 300

Ile Asp Gln Ala Arg Arg Ser Leu Glu Arg Thr Leu Ser Gly Lys Gly
305                 310                 315                 320

Pro Glu Lys Glu Leu Leu Val Ser Met Glu Leu Asp Asn Ile Lys Val
                325                 330                 335

Thr Ile Glu Lys Glu Lys Lys Leu Ser Asp Ser Glu Gly Ser Tyr Trp
            340                 345                 350

Asp Cys Leu Lys Asp Ser Val Asn Arg Arg Thr Arg Ile Ala Cys
        355                 360                 365

Leu Cys Trp Val Gly Gln Thr Thr Cys Gly Thr Ser Leu Ile Gly Asn
    370                 375                 380

Ser Thr Tyr Phe Tyr Glu Lys Ala Gly Val Gly Thr Asp Thr Ala Phe
385                 390                 395                 400

Thr Phe Ser Ile Ile Gln Tyr Cys Leu Gly Ile Ala Ala Thr Phe Leu
                405                 410                 415

Ser Trp Trp Ala Ser Lys Tyr Phe Gly Arg Phe Asp Leu Tyr Ala Phe
            420                 425                 430

Gly Leu Ala Ile Gln Thr Val Ser Leu Phe Ile Ile Gly Gly Leu Gly
        435                 440                 445

Cys Ser Asp Ser His Gly Ala Glu Met Gly Ser Gly Ser Leu Leu Met
    450                 455                 460

Val Leu Ser Phe Phe Tyr Asn Leu Gly Ile Ala Pro Val Val Phe Cys
465                 470                 475                 480

Leu Val Ser Glu Ile Pro Ser Ser Arg Leu Arg Thr Lys Ser Ile Ile
                485                 490                 495

Leu Ala Arg Asn Ala Tyr Asn Met Ala Ser Ile Val Thr Thr Val Leu
            500                 505                 510

Ile Met Tyr Gln Leu Asn Ser Glu Lys Trp Asn Trp Gly Ala Lys Ser
        515                 520                 525

Gly Phe Phe Trp Gly Gly Leu Cys Phe Ala Thr Leu Val Trp Ala Val
    530                 535                 540

Ile Asp Leu Pro Glu Thr Ala Gly Arg Thr Phe Ile Glu Ile Asn Glu
545                 550                 555                 560

Leu Phe Arg Leu Gly Val Pro Ala Arg Lys Phe Lys Ser Thr Lys Val
                565                 570                 575

Asp Pro Phe Ala Ala Lys Ala Ala Ala Glu Ile Asn Val Lys
            580                 585                 590

Asp Pro Lys Glu Asp Leu Glu Thr Ser Val Val Asp Glu Gly Arg Ser
```

```
                   595                 600                 605
Thr Pro Ser Val Val Asn Lys
    610                 615

<210> SEQ ID NO 9
<211> LENGTH: 1848
<212> TYPE: DNA
<213> ORGANISM: Saccharomyces cerevisiae
<220> FEATURE:
<221> NAME/KEY: CDS
<222> LOCATION: (1)..(1848)
<223> OTHER INFORMATION: Agt1 Transporter Protein

<400> SEQUENCE: 9 atg aaa aat atc att tca ttg gta agc aag aag aag gct gcc tca aaa      48
Met Lys Asn Ile Ile Ser Leu Val Ser Lys Lys Lys Ala Ala Ser Lys
1               5                   10                  15 aat gag gat aaa aac att tct gag tct tca aga gat att gta aac caa      96
Asn Glu Asp Lys Asn Ile Ser Glu Ser Ser Arg Asp Ile Val Asn Gln
            20                  25                  30 cag gag gtt ttc aat act gaa gat ttt gaa gaa ggg aaa aag gat agt     144
Gln Glu Val Phe Asn Thr Glu Asp Phe Glu Glu Gly Lys Lys Asp Ser
        35                  40                  45 gcc ttt gag cta gac cac tta gag ttc acc acc aat tca gcc cag tta     192
Ala Phe Glu Leu Asp His Leu Glu Phe Thr Thr Asn Ser Ala Gln Leu
    50                  55                  60 gga gat tct gac gaa gat aac gag aat gtg att aat gag atg aac gct     240
Gly Asp Ser Asp Glu Asp Asn Glu Asn Val Ile Asn Glu Met Asn Ala
65                  70                  75                  80 act gat gat gca aat gaa gct aac agc gag gaa aaa agc atg act ttg     288
Thr Asp Asp Ala Asn Glu Ala Asn Ser Glu Glu Lys Ser Met Thr Leu
                85                  90                  95 aag cag gcg ttg cta aaa tat cca aaa gca gcc ctg tgg tcc ata tta     336
Lys Gln Ala Leu Leu Lys Tyr Pro Lys Ala Ala Leu Trp Ser Ile Leu
            100                 105                 110 gtg tct act acc ctg gtt atg gaa ggt tat gat acc gca cta ctg agc     384
Val Ser Thr Thr Leu Val Met Glu Gly Tyr Asp Thr Ala Leu Leu Ser
        115                 120                 125 gca ctg tat gcc ctg cca gtt ttt cag aga aaa ttc ggt act ttg aac     432
Ala Leu Tyr Ala Leu Pro Val Phe Gln Arg Lys Phe Gly Thr Leu Asn
    130                 135                 140 ggg gag ggt tct tac gaa att act tcc caa tgg cag att ggt tta aac     480
Gly Glu Gly Ser Tyr Glu Ile Thr Ser Gln Trp Gln Ile Gly Leu Asn
145                 150                 155                 160 atg tgt gtc ctt tgt ggt gag atg att ggt ttg caa atc acg act tat     528
Met Cys Val Leu Cys Gly Glu Met Ile Gly Leu Gln Ile Thr Thr Tyr
                165                 170                 175 atg gtt gaa ttt atg ggg aat cgt tat acg atg att aca gca ctt ggt     576
Met Val Glu Phe Met Gly Asn Arg Tyr Thr Met Ile Thr Ala Leu Gly
            180                 185                 190 ttg tta act gct tat atc ttt atc ctc tac tac tgt aaa agt tta gct     624
Leu Leu Thr Ala Tyr Ile Phe Ile Leu Tyr Tyr Cys Lys Ser Leu Ala
        195                 200                 205 atg att gct gtg gga caa att ctc tca gct ata cca tgg ggt tgt ttc     672
Met Ile Ala Val Gly Gln Ile Leu Ser Ala Ile Pro Trp Gly Cys Phe
    210                 215                 220 caa agt ttg gct gtt act tat gct tcg gaa gtt tgc cct tta gca tta     720
Gln Ser Leu Ala Val Thr Tyr Ala Ser Glu Val Cys Pro Leu Ala Leu
225                 230                 235                 240 aga tat tac atg acc agt tac tcc aac att tgt tgg tta ttt ggt caa     768
Arg Tyr Tyr Met Thr Ser Tyr Ser Asn Ile Cys Trp Leu Phe Gly Gln
                245                 250                 255
```

-continued

| | | |
|---|---|---|
| atc ttc gcc tct ggt att atg aaa aac tca caa gag aat tta ggg aac<br>Ile Phe Ala Ser Gly Ile Met Lys Asn Ser Gln Glu Asn Leu Gly Asn<br>260                        265                       270 | | 816 |
| tcc gac ttg ggc tat aaa ttg cca ttt gct tta caa tgg att tgg cct<br>Ser Asp Leu Gly Tyr Lys Leu Pro Phe Ala Leu Gln Trp Ile Trp Pro<br>            275                       280                       285 | | 864 |
| gct cct tta atg atc ggt atc ttt ttc gct cct gag tcg ccc tgg tgg<br>Ala Pro Leu Met Ile Gly Ile Phe Phe Ala Pro Glu Ser Pro Trp Trp<br>290                       295                       300 | | 912 |
| ttg gtg aga aag gat agg gtc gct gag gca aga aaa tct tta agc aga<br>Leu Val Arg Lys Asp Arg Val Ala Glu Ala Arg Lys Ser Leu Ser Arg<br>305                       310                       315                   320 | | 960 |
| att ttg agt ggt aaa ggc gcc gag aag gac att caa gtt gat ctt act<br>Ile Leu Ser Gly Lys Gly Ala Glu Lys Asp Ile Gln Val Asp Leu Thr<br>            325                       330                       335 | | 1008 |
| tta aag cag att gaa ttg act att gaa aaa gaa aga ctt tta gca tct<br>Leu Lys Gln Ile Glu Leu Thr Ile Glu Lys Glu Arg Leu Leu Ala Ser<br>                  340                       345                   350 | | 1056 |
| aaa tca gga tca ttc ttt aat tgt ttc aag gga gtt aat gga aga aga<br>Lys Ser Gly Ser Phe Phe Asn Cys Phe Lys Gly Val Asn Gly Arg Arg<br>355                       360                       365 | | 1104 |
| acg aga ctt gca tgt tta act tgg gta gct caa aat agt agc ggt gcc<br>Thr Arg Leu Ala Cys Leu Thr Trp Val Ala Gln Asn Ser Ser Gly Ala<br>        370                       375                       380 | | 1152 |
| gtt tta ctt ggt tac tcg aca tat ttt ttt gaa aga gca ggt atg gcc<br>Val Leu Leu Gly Tyr Ser Thr Tyr Phe Phe Glu Arg Ala Gly Met Ala<br>385                       390                       395                   400 | | 1200 |
| acc gac aag gcg ttt act ttt tct cta att cag tac tgt ctt ggg tta<br>Thr Asp Lys Ala Phe Thr Phe Ser Leu Ile Gln Tyr Cys Leu Gly Leu<br>            405                       410                       415 | | 1248 |
| gcg ggt aca ctt tgc tcc tgg gta ata tct ggc cgt gtt ggt aga tgg<br>Ala Gly Thr Leu Cys Ser Trp Val Ile Ser Gly Arg Val Gly Arg Trp<br>                  420                       425                   430 | | 1296 |
| aca ata ctg acc tat ggt ctt gca ttt caa atg gtc tgc tta ttt att<br>Thr Ile Leu Thr Tyr Gly Leu Ala Phe Gln Met Val Cys Leu Phe Ile<br>435                       440                       445 | | 1344 |
| att ggt gga atg ggt ttt ggt tct gga agc agc gct agt aat ggt gcc<br>Ile Gly Gly Met Gly Phe Gly Ser Gly Ser Ser Ala Ser Asn Gly Ala<br>        450                       455                       460 | | 1392 |
| ggt ggt tta ttg ctg gct tta tca ttc ttt tac aat gct ggt atc ggt<br>Gly Gly Leu Leu Leu Ala Leu Ser Phe Phe Tyr Asn Ala Gly Ile Gly<br>465                       470                       475                   480 | | 1440 |
| gca gtt gtt tac tgt atc gtt gct gaa att cca tca gcg gag ttg aga<br>Ala Val Val Tyr Cys Ile Val Ala Glu Ile Pro Ser Ala Glu Leu Arg<br>                  485                       490                   495 | | 1488 |
| act aag act ata gtg ctg gcc cgt att tgc tac aat ctc atg gcc gtt<br>Thr Lys Thr Ile Val Leu Ala Arg Ile Cys Tyr Asn Leu Met Ala Val<br>            500                       505                       510 | | 1536 |
| att aac gct ata tta acg ccc tat atg cta aac gtg agc gat tgg aac<br>Ile Asn Ala Ile Leu Thr Pro Tyr Met Leu Asn Val Ser Asp Trp Asn<br>515                       520                       525 | | 1584 |
| tgg ggt gcc aaa act ggt cta tac tgg ggt ggt ttc aca gca gtc act<br>Trp Gly Ala Lys Thr Gly Leu Tyr Trp Gly Gly Phe Thr Ala Val Thr<br>        530                       535                       540 | | 1632 |
| tta gct tgg gtc atc atc gat ctg cct gag aca act ggt aga acc ttc<br>Leu Ala Trp Val Ile Ile Asp Leu Pro Glu Thr Thr Gly Arg Thr Phe<br>545                       550                       555                   560 | | 1680 |
| agt gaa att aat gaa ctt ttc aac caa ggg gtt cct gcc aga aaa ttt<br>Ser Glu Ile Asn Glu Leu Phe Asn Gln Gly Val Pro Ala Arg Lys Phe<br>                  565                       570                   575 | | 1728 |

```
gca tct act gtg gtt gat cca ttc gga aag gga aaa act caa cat gat   1776
Ala Ser Thr Val Val Asp Pro Phe Gly Lys Gly Lys Thr Gln His Asp
            580                 585                 590 tcg cta gct gat gag agt atc agt cag tcc tca agc ata aaa cag cga   1824
Ser Leu Ala Asp Glu Ser Ile Ser Gln Ser Ser Ser Ile Lys Gln Arg
        595                 600                 605 gaa tta aat gca gct gat aaa tgt                                   1848
Glu Leu Asn Ala Ala Asp Lys Cys
    610                 615

<210> SEQ ID NO 10
<211> LENGTH: 616
<212> TYPE: PRT
<213> ORGANISM: Saccharomyces cerevisiae

<400> SEQUENCE: 10

Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asp Phe Glu Glu Gly Lys Lys Asp Ser
        35                  40                  45

Ala Phe Glu Leu Asp His Leu Glu Phe Thr Thr Asn Ser Ala Gln Leu
    50                  55                  60

Gly Asp Ser Asp Glu Asp Asn Glu Asn Val Ile Asn Glu Met Asn Ala
65              70                  75                  80

Thr Asp Asp Ala Asn Glu Ala Asn Ser Glu Glu Lys Ser Met Thr Leu
            85                  90                  95

Lys Gln Ala Leu Leu Lys Tyr Pro Lys Ala Ala Leu Trp Ser Ile Leu
        100                 105                 110

Val Ser Thr Thr Leu Val Met Glu Gly Tyr Asp Thr Ala Leu Leu Ser
    115                 120                 125

Ala Leu Tyr Ala Leu Pro Val Phe Gln Arg Lys Phe Gly Thr Leu Asn
    130                 135                 140

Gly Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
            180                 185                 190

Leu Leu Thr Ala Tyr Ile Phe Ile Leu Tyr Tyr Cys Lys Ser Leu Ala
        195                 200                 205

Met Ile Ala Val Gly Gln Ile Leu Ser Ala Ile Pro Trp Gly Cys Phe
    210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285

Ala Pro Leu Met Ile Gly Ile Phe Phe Ala Pro Glu Ser Pro Trp Trp
    290                 295                 300

Leu Val Arg Lys Asp Arg Val Ala Glu Ala Arg Lys Ser Leu Ser Arg
305                 310                 315                 320
```

Ile Leu Ser Gly Lys Gly Ala Glu Lys Asp Ile Gln Val Asp Leu Thr
                325                 330                 335

Leu Lys Gln Ile Glu Leu Thr Ile Glu Lys Glu Arg Leu Leu Ala Ser
            340                 345                 350

Lys Ser Gly Ser Phe Phe Asn Cys Phe Lys Gly Val Asn Gly Arg Arg
        355                 360                 365

Thr Arg Leu Ala Cys Leu Thr Trp Val Ala Gln Asn Ser Ser Gly Ala
    370                 375                 380

Val Leu Leu Gly Tyr Ser Thr Tyr Phe Phe Glu Arg Ala Gly Met Ala
385                 390                 395                 400

Thr Asp Lys Ala Phe Thr Phe Ser Leu Ile Gln Tyr Cys Leu Gly Leu
                405                 410                 415

Ala Gly Thr Leu Cys Ser Trp Val Ile Ser Gly Arg Val Gly Arg Trp
            420                 425                 430

Thr Ile Leu Thr Tyr Gly Leu Ala Phe Gln Met Val Cys Leu Phe Ile
        435                 440                 445

Ile Gly Gly Met Gly Phe Gly Ser Gly Ser Ala Ser Asn Gly Ala
    450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
            500                 505                 510

Ile Asn Ala Ile Leu Thr Pro Tyr Met Leu Asn Val Ser Asp Trp Asn
        515                 520                 525

Trp Gly Ala Lys Thr Gly Leu Tyr Trp Gly Phe Thr Ala Val Thr
    530                 535                 540

Leu Ala Trp Val Ile Ile Asp Leu Pro Glu Thr Thr Gly Arg Thr Phe
545                 550                 555                 560

Ser Glu Ile Asn Glu Leu Phe Asn Gln Gly Val Pro Ala Arg Lys Phe
                565                 570                 575

Ala Ser Thr Val Val Asp Pro Phe Gly Lys Gly Lys Thr Gln His Asp
            580                 585                 590

Ser Leu Ala Asp Glu Ser Ile Ser Gln Ser Ser Ser Ile Lys Gln Arg
        595                 600                 605

Glu Leu Asn Ala Ala Asp Lys Cys
    610                 615

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agagctcagc atataaagag aca                                          23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 12
tggatccgta tctacctact gg                                      22

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgagctcaca tagaagaaca tcaaa                                   25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atggatccat atgaaaaata tcatt                                   25

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tctagaatta catccaagac tattaattaa ctatg                        35

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggatccgta tctacctact gg                                      22

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtctttccca tcttgagtac ggtcc                                   25

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
```
caaaatcact tttcttacct tgctcct        27

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atgagtacgg tccaggttca ctaa        24

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gatgggaaag atcaaaatca cttttc        26

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtctttccca tcatgagtac ggtcca        26

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caaaatcact tttcttacct tgctcct        27

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtctttccca tcatgagtac ggtcc        25

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caaaatcact tttcttacct tgctcct        27

<210> SEQ ID NO 25
<211> LENGTH: 1842
<212> TYPE: DNA
<213> ORGANISM: Artificial Sequence
<220> FEATURE:
<223> OTHER INFORMATION: Description of Artificial Sequence: Synthetic
      MAL61[D46G] polynucleotide
<220> FEATURE:
<221> NAME/KEY: CDS
<222> LOCATION: (1)..(1842)
<223> OTHER INFORMATION: Mal61p[Gly46]

<400> SEQUENCE: 25

| | | | | | | | | | | | | | | | | |
|---|---|---|---|---|---|---|---|---|---|---|---|---|---|---|---|---|
| atg | aag | gga | tta | tcc | tca | tta | ata | aac | aga | aaa | aaa | gac | agg | aac | gac | 48 |
| Met | Lys | Gly | Leu | Ser | Ser | Leu | Ile | Asn | Arg | Lys | Lys | Asp | Arg | Asn | Asp | |
| 1 | | | | 5 | | | | | 10 | | | | | 15 | | |
| tca | cac | tta | gat | gag | atc | gag | aat | ggc | gtg | aac | gct | acc | gaa | ttc | aac | 96 |
| Ser | His | Leu | Asp | Glu | Ile | Glu | Asn | Gly | Val | Asn | Ala | Thr | Glu | Phe | Asn | |
| | | | 20 | | | | | 25 | | | | | 30 | | | |
| tcg | ata | gag | atg | gag | gag | caa | ggt | aag | aaa | agt | gat | ttt | ggt | ctt | tcc | 144 |
| Ser | Ile | Glu | Met | Glu | Glu | Gln | Gly | Lys | Lys | Ser | Asp | Phe | Gly | Leu | Ser | |
| | 35 | | | | | 40 | | | | | 45 | | | | | |
| cat | ctt | gag | tac | ggt | cca | ggt | tca | cta | ata | cca | aac | gat | aat | aat | gaa | 192 |
| His | Leu | Glu | Tyr | Gly | Pro | Gly | Ser | Leu | Ile | Pro | Asn | Asp | Asn | Asn | Glu | |
| 50 | | | | | 55 | | | | | 60 | | | | | | |
| gaa | gtc | ccc | gac | ctt | ctc | gat | gaa | gct | atg | cag | gac | gcc | aaa | gag | gca | 240 |
| Glu | Val | Pro | Asp | Leu | Leu | Asp | Glu | Ala | Met | Gln | Asp | Ala | Lys | Glu | Ala | |
| 65 | | | | 70 | | | | | 75 | | | | | 80 | | |
| gat | gaa | agt | gag | agg | gga | atg | cca | ctc | atg | aca | gct | ttg | aag | aca | tat | 288 |
| Asp | Glu | Ser | Glu | Arg | Gly | Met | Pro | Leu | Met | Thr | Ala | Leu | Lys | Thr | Tyr | |
| | | | 85 | | | | | 90 | | | | | 95 | | | |
| cca | aaa | gct | gct | gct | tgg | tca | cta | tta | gtt | tcc | aca | aca | ttg | att | caa | 336 |
| Pro | Lys | Ala | Ala | Ala | Trp | Ser | Leu | Leu | Val | Ser | Thr | Thr | Leu | Ile | Gln | |
| | | 100 | | | | | 105 | | | | | 110 | | | | |
| gag | ggt | tat | gac | aca | gcc | att | cta | gga | gct | ttc | tat | gcc | ctg | cct | gtt | 384 |
| Glu | Gly | Tyr | Asp | Thr | Ala | Ile | Leu | Gly | Ala | Phe | Tyr | Ala | Leu | Pro | Val | |
| | | | 115 | | | | | 120 | | | | | 125 | | | |
| ttt | caa | aaa | aaa | tat | ggt | tct | ttg | aat | agc | aat | aca | gga | gat | tat | gaa | 432 |
| Phe | Gln | Lys | Lys | Tyr | Gly | Ser | Leu | Asn | Ser | Asn | Thr | Gly | Asp | Tyr | Glu | |
| | 130 | | | | | 135 | | | | | 140 | | | | | |
| att | tca | gtt | tcc | tgg | caa | atc | ggt | cta | tgt | cta | tgc | tac | atg | gca | ggt | 480 |
| Ile | Ser | Val | Ser | Trp | Gln | Ile | Gly | Leu | Cys | Leu | Cys | Tyr | Met | Ala | Gly | |
| 145 | | | | | 150 | | | | | 155 | | | | | 160 | |
| gag | att | gtc | ggt | ttg | caa | gtg | act | ggg | cct | tct | gta | gat | tac | atg | ggc | 528 |
| Glu | Ile | Val | Gly | Leu | Gln | Val | Thr | Gly | Pro | Ser | Val | Asp | Tyr | Met | Gly | |
| | | | 165 | | | | | 170 | | | | | 175 | | | |
| aac | cgt | tac | act | ctg | atc | atg | gcg | ttg | ttc | ttt | tta | gcg | gct | ttc | att | 576 |
| Asn | Arg | Tyr | Thr | Leu | Ile | Met | Ala | Leu | Phe | Phe | Leu | Ala | Ala | Phe | Ile | |
| | | | | 180 | | | | | 185 | | | | | 190 | | |
| ttc | att | ctg | tat | ttt | tgc | aag | agt | ttg | ggt | atg | att | gcc | gtg | gga | cag | 624 |
| Phe | Ile | Leu | Tyr | Phe | Cys | Lys | Ser | Leu | Gly | Met | Ile | Ala | Val | Gly | Gln | |
| | | | 195 | | | | | 200 | | | | | 205 | | | |
| gca | ttg | tgt | ggt | atg | cca | tgg | ggt | tgt | ttc | caa | tgt | ttg | acc | gtt | tct | 672 |
| Ala | Leu | Cys | Gly | Met | Pro | Trp | Gly | Cys | Phe | Gln | Cys | Leu | Thr | Val | Ser | |
| | 210 | | | | | 215 | | | | | 220 | | | | | |
| tat | gct | tct | gaa | att | tgt | cct | ttg | gcc | cta | aga | tac | tat | ttg | acg | act | 720 |
| Tyr | Ala | Ser | Glu | Ile | Cys | Pro | Leu | Ala | Leu | Arg | Tyr | Tyr | Leu | Thr | Thr | |
| 225 | | | | | 230 | | | | | 235 | | | | | 240 | |
| tat | tct | aat | tta | tgt | tgg | acg | ttc | ggt | caa | ctt | ttc | gct | gct | ggt | att | 768 |
| Tyr | Ser | Asn | Leu | Cys | Trp | Thr | Phe | Gly | Gln | Leu | Phe | Ala | Ala | Gly | Ile | |
| | | | | 245 | | | | | 250 | | | | | 255 | | |
| atg | aaa | aat | tcc | cag | aac | aaa | tat | gcc | aac | tca | gaa | cta | gga | tat | aag | 816 |
| | | | | | | | | | | | | | | | | |

```
                Met Lys Asn Ser Gln Asn Lys Tyr Ala Asn Ser Glu Leu Gly Tyr Lys
                            260                 265                 270 cta cct ttt gct ttg cag tgg atc tgg ccc ctt cct ttg gcg gta ggt        864
Leu Pro Phe Ala Leu Gln Trp Ile Trp Pro Leu Pro Leu Ala Val Gly
            275                 280                 285 att ttt ttg gca cca gag tct cca tgg tgg ctg gtt aaa aaa gga agg        912
Ile Phe Leu Ala Pro Glu Ser Pro Trp Trp Leu Val Lys Lys Gly Arg
            290                 295                 300 att gat cag gcg agg aga tca ctt gaa aga ata tta agt ggt aaa gga        960
Ile Asp Gln Ala Arg Arg Ser Leu Glu Arg Ile Leu Ser Gly Lys Gly
305                 310                 315                 320 ccc gag aaa gaa tta cta gtg agt atg gaa ctc gat aaa atc aaa act       1008
Pro Glu Lys Glu Leu Leu Val Ser Met Glu Leu Asp Lys Ile Lys Thr
                325                 330                 335 act ata gaa aag gag cag aaa atg tct gat gaa gga act tac tgg gat       1056
Thr Ile Glu Lys Glu Gln Lys Met Ser Asp Glu Gly Thr Tyr Trp Asp
            340                 345                 350 tgt gtg aaa gat ggt att aac agg aga aga acg aga ata gct tgt tta       1104
Cys Val Lys Asp Gly Ile Asn Arg Arg Arg Thr Arg Ile Ala Cys Leu
            355                 360                 365 tgt tgg atc ggt caa tgc tcc tgt ggt gca tca tta att ggt tat tca       1152
Cys Trp Ile Gly Gln Cys Ser Cys Gly Ala Ser Leu Ile Gly Tyr Ser
            370                 375                 380 act tac ttt tat gaa aaa gct ggt gtt agc act gat acg gct ttt act       1200
Thr Tyr Phe Tyr Glu Lys Ala Gly Val Ser Thr Asp Thr Ala Phe Thr
385                 390                 395                 400 ttc agt att atc caa tat tgt ctt ggt att gct gca acg ttt gta tcc       1248
Phe Ser Ile Ile Gln Tyr Cys Leu Gly Ile Ala Ala Thr Phe Val Ser
            405                 410                 415 tgg tgg gct tca aaa tat tgt ggc aga ttt gac ctt tat gct ttt ggg       1296
Trp Trp Ala Ser Lys Tyr Cys Gly Arg Phe Asp Leu Tyr Ala Phe Gly
            420                 425                 430 ctg gct ttt cag gct att atg ttc ttc att atc ggt ggt tta gga tgt       1344
Leu Ala Phe Gln Ala Ile Met Phe Phe Ile Ile Gly Gly Leu Gly Cys
            435                 440                 445 tca gac act cat ggc gct aaa atg ggt agt ggt gct ctt cta atg gtt       1392
Ser Asp Thr His Gly Ala Lys Met Gly Ser Gly Ala Leu Leu Met Val
450                 455                 460 gtc gcg ttc ttt tac aac ctc ggt att gca cct gtt gtt ttt tgc tta       1440
Val Ala Phe Phe Tyr Asn Leu Gly Ile Ala Pro Val Val Phe Cys Leu
465                 470                 475                 480 gtg tct gaa atg ccg tct tca agg cta aga acc aaa aca att att ttg       1488
Val Ser Glu Met Pro Ser Ser Arg Leu Arg Thr Lys Thr Ile Ile Leu
            485                 490                 495 gct cgt aat gct tac aat gtg atc caa gtt gta gtt aca gtt ttg atc       1536
Ala Arg Asn Ala Tyr Asn Val Ile Gln Val Val Val Thr Val Leu Ile
            500                 505                 510 atg tac caa ttg aac tca gag aaa tgg aat tgg ggt gct aaa tca ggc       1584
Met Tyr Gln Leu Asn Ser Glu Lys Trp Asn Trp Gly Ala Lys Ser Gly
            515                 520                 525 ttt ttc tgg gga gga ttt tgt ctg gcc act tta gct tgg gct gtt gtc       1632
Phe Phe Trp Gly Gly Phe Cys Leu Ala Thr Leu Ala Trp Ala Val Val
            530                 535                 540 gat tta cca gaa acc gct ggc agg act ttt att gag ata aat gaa ttg       1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac       1728
Phe Arg Leu Gly Val Pro Ala Arg Lys Phe Lys Ser Thr Lys Val Asp
                565                 570                 575 cct ttt gca gct gcc aaa gca gca gct gca gaa att aat gtt aaa gat       1776
Pro Phe Ala Ala Ala Lys Ala Ala Ala Ala Glu Ile Asn Val Lys Asp
```

```
                     Pro Phe Ala Ala Ala Lys Ala Ala Ala Glu Ile Asn Val Lys Asp
                                 580                 585                 590 ccg aag gaa gat ttg gaa act tct gtg gta gat gaa ggg cga agc acc              1824
Pro Lys Glu Asp Leu Glu Thr Ser Val Val Asp Glu Gly Arg Ser Thr
            595                 600                 605 cca tct gtt gtg aac aaa                                                      1842
Pro Ser Val Val Asn Lys
        610

<210> SEQ ID NO 26
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Gly Leu Ser
        35                  40                  45

His Leu Glu Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ala Phe Tyr Ala Leu Pro Val
        115                 120                 125

Phe Gln Lys Lys Tyr Gly Ser Leu Asn Ser Asn Thr Gly Asp Tyr Glu
    130                 135                 140

Ile Ser Val Ser Trp Gln Ile Gly Leu Cys Leu Cys Tyr Met Ala Gly
145                 150                 155                 160

Glu Ile Val Gly Leu Gln Val Thr Gly Pro Ser Val Asp Tyr Met Gly
                165                 170                 175

Asn Arg Tyr Thr Leu Ile Met Ala Leu Phe Phe Leu Ala Ala Phe Ile
            180                 185                 190

Phe Ile Leu Tyr Phe Cys Lys Ser Leu Gly Met Ile Ala Val Gly Gln
        195                 200                 205

Ala Leu Cys Gly Met Pro Trp Gly Cys Phe Gln Cys Leu Thr Val Ser
    210                 215                 220

Tyr Ala Ser Glu Ile Cys Pro Leu Ala Leu Arg Tyr Tyr Leu Thr Thr
225                 230                 235                 240

Tyr Ser Asn Leu Cys Trp Thr Phe Gly Gln Leu Phe Ala Ala Gly Ile
                245                 250                 255

Met Lys Asn Ser Gln Asn Lys Tyr Ala Asn Ser Glu Leu Gly Tyr Lys
            260                 265                 270

Leu Pro Phe Ala Leu Gln Trp Ile Trp Pro Leu Pro Leu Ala Val Gly
        275                 280                 285

Ile Phe Leu Ala Pro Glu Ser Pro Trp Trp Leu Val Lys Lys Gly Arg
    290                 295                 300

Ile Asp Gln Ala Arg Arg Ser Leu Glu Arg Ile Leu Ser Gly Lys Gly
```

```
                        305                 310                 315                 320
Pro Glu Lys Glu Leu Leu Val Ser Met Glu Leu Asp Lys Ile Lys Thr
                325                 330                 335

Thr Ile Glu Lys Glu Gln Lys Met Ser Asp Glu Gly Thr Tyr Trp Asp
            340                 345                 350

Cys Val Lys Asp Gly Ile Asn Arg Arg Thr Arg Ile Ala Cys Leu
        355                 360                 365

Cys Trp Ile Gly Gln Cys Ser Cys Gly Ala Ser Leu Ile Gly Tyr Ser
    370                 375                 380

Thr Tyr Phe Tyr Glu Lys Ala Gly Val Ser Thr Asp Thr Ala Phe Thr
385                 390                 395                 400

Phe Ser Ile Ile Gln Tyr Cys Leu Gly Ile Ala Ala Thr Phe Val Ser
                405                 410                 415

Trp Trp Ala Ser Lys Tyr Cys Gly Arg Phe Asp Leu Tyr Ala Phe Gly
            420                 425                 430

Leu Ala Phe Gln Ala Ile Met Phe Phe Ile Ile Gly Gly Leu Gly Cys
        435                 440                 445

Ser Asp Thr His Gly Ala Lys Met Gly Ser Gly Ala Leu Leu Met Val
    450                 455                 460

Val Ala Phe Phe Tyr Asn Leu Gly Ile Ala Pro Val Val Phe Cys Leu
465                 470                 475                 480

Val Ser Glu Met Pro Ser Ser Arg Leu Arg Thr Lys Thr Ile Ile Leu
                485                 490                 495

Ala Arg Asn Ala Tyr Asn Val Ile Gln Val Val Val Thr Val Leu Ile
            500                 505                 510

Met Tyr Gln Leu Asn Ser Glu Lys Trp Asn Trp Gly Ala Lys Ser Gly
        515                 520                 525

Phe Phe Trp Gly Gly Phe Cys Leu Ala Thr Leu Ala Trp Ala Val Val
    530                 535                 540

Asp Leu Pro Glu Thr Ala Gly Arg Thr Phe Ile Glu Ile Asn Glu Leu
545                 550                 555                 560

Phe Arg Leu Gly Val Pro Ala Arg Lys Phe Lys Ser Thr Lys Val Asp
                565                 570                 575

Pro Phe Ala Ala Ala Lys Ala Ala Ala Glu Ile Asn Val Lys Asp
            580                 585                 590

Pro Lys Glu Asp Leu Glu Thr Ser Val Val Asp Glu Gly Arg Ser Thr
        595                 600                 605

Pro Ser Val Val Asn Lys
    610

<210> SEQ ID NO 27
<211> LENGTH: 1842
<212> TYPE: DNA
<213> ORGANISM: Artificial Sequence
<220> FEATURE:
<223> OTHER INFORMATION: Description of Artificial Sequence: Synthetic
      MAL61[L50H] polynucleotide
<220> FEATURE:
<221> NAME/KEY: CDS
<222> LOCATION: (1)..(1842)
<223> OTHER INFORMATION: Mal61p[His50]

<400> SEQUENCE: 27 atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac     96
Ser His Leu Asp Glu Ile Glu Asn Gly Val Asn Ala Thr Glu Phe Asn
```

-continued

```
            20                  25                  30
tcg ata gag atg gag gag caa ggt aag aaa agt gat ttt gat ctt tcc        144
Ser Ile Glu Met Glu Glu Gln Gly Lys Lys Ser Asp Phe Asp Leu Ser
         35                  40                  45 cat cat gag tac ggt cca ggt tca cta ata cca aac gat aat aat gaa        192
His His Glu Tyr Gly Pro Gly Ser Leu Ile Pro Asn Asp Asn Asn Glu
 50                  55                  60 gaa gtc ccc gac ctt ctc gat gaa gct atg cag gac gcc aaa gag gca        240
Glu Val Pro Asp Leu Leu Asp Glu Ala Met Gln Asp Ala Lys Glu Ala
 65                  70                  75                  80 gat gaa agt gag agg gga atg cca ctc atg aca gct ttg aag aca tat        288
Asp Glu Ser Glu Arg Gly Met Pro Leu Met Thr Ala Leu Lys Thr Tyr
                 85                  90                  95 cca aaa gct gct gct tgg tca cta tta gtt tcc aca aca ttg att caa        336
Pro Lys Ala Ala Ala Trp Ser Leu Leu Val Ser Thr Thr Leu Ile Gln
            100                 105                 110 gag ggt tat gac aca gcc att cta gga gct ttc tat gcc ctg cct gtt        384
Glu Gly Tyr Asp Thr Ala Ile Leu Gly Ala Phe Tyr Ala Leu Pro Val
        115                 120                 125 ttt caa aaa aaa tat ggt tct ttg aat agc aat aca gga gat tat gaa        432
Phe Gln Lys Lys Tyr Gly Ser Leu Asn Ser Asn Thr Gly Asp Tyr Glu
130                 135                 140 att tca gtt tcc tgg caa atc ggt cta tgt cta tgc tac atg gca ggt        480
Ile Ser Val Ser Trp Gln Ile Gly Leu Cys Leu Cys Tyr Met Ala Gly
145                 150                 155                 160 gag att gtc ggt ttg caa gtg act ggg cct tct gta gat tac atg ggc        528
Glu Ile Val Gly Leu Gln Val Thr Gly Pro Ser Val Asp Tyr Met Gly
                165                 170                 175 aac cgt tac act ctg atc atg gcg ttg ttc ttt tta gcg gct ttc att        576
Asn Arg Tyr Thr Leu Ile Met Ala Leu Phe Phe Leu Ala Ala Phe Ile
            180                 185                 190 ttc att ctg tat ttt tgc aag agt ttg ggt atg att gcc gtg gga cag        624
Phe Ile Leu Tyr Phe Cys Lys Ser Leu Gly Met Ile Ala Val Gly Gln
        195                 200                 205 gca ttg tgt ggt atg cca tgg ggt tgt ttc caa tgt ttg acc gtt tct        672
Ala Leu Cys Gly Met Pro Trp Gly Cys Phe Gln Cys Leu Thr Val Ser
210                 215                 220 tat gct tct gaa att tgt cct ttg gcc cta aga tac tat ttg acg act        720
Tyr Ala Ser Glu Ile Cys Pro Leu Ala Leu Arg Tyr Tyr Leu Thr Thr
225                 230                 235                 240 tat tct aat tta tgt tgg acg ttc ggt caa ctt ttc gct gct ggt att        768
Tyr Ser Asn Leu Cys Trp Thr Phe Gly Gln Leu Phe Ala Ala Gly Ile
                245                 250                 255 atg aaa aat tcc cag aac aaa tat gcc aac tca gaa cta gga tat aag        816
Met Lys Asn Ser Gln Asn Lys Tyr Ala Asn Ser Glu Leu Gly Tyr Lys
            260                 265                 270 cta cct ttt gct ttg cag tgg atc tgg ccc ctt cct ttg gcg gta ggt        864
Leu Pro Phe Ala Leu Gln Trp Ile Trp Pro Leu Pro Leu Ala Val Gly
        275                 280                 285 att ttt ttg gca cca gag tct cca tgg tgg ctg gtt aaa aaa gga agg        912
Ile Phe Leu Ala Pro Glu Ser Pro Trp Trp Leu Val Lys Lys Gly Arg
290                 295                 300 att gat cag gcg agg aga tca ctt gaa aga ata tta agt ggt aaa gga        960
Ile Asp Gln Ala Arg Arg Ser Leu Glu Arg Ile Leu Ser Gly Lys Gly
305                 310                 315                 320 ccc gag aaa gaa tta cta gtg agt atg gaa ctc gat aaa atc aaa act       1008
Pro Glu Lys Glu Leu Leu Val Ser Met Glu Leu Asp Lys Ile Lys Thr
                325                 330                 335 act ata gaa aag gag cag aaa atg tct gat gaa gga act tac tgg gat       1056
Thr Ile Glu Lys Glu Gln Lys Met Ser Asp Glu Gly Thr Tyr Trp Asp
```

```
                340             345             350
tgt gtg aaa gat ggt att aac agg aga aga acg aga ata gct tgt tta    1104
Cys Val Lys Asp Gly Ile Asn Arg Arg Arg Thr Arg Ile Ala Cys Leu
    355             360             365 tgt tgg atc ggt caa tgc tcc tgt ggt gca tca tta att ggt tat tca    1152
Cys Trp Ile Gly Gln Cys Ser Cys Gly Ala Ser Leu Ile Gly Tyr Ser
370             375             380 act tac ttt tat gaa aaa gct ggt gtt agc act gat acg gct ttt act    1200
Thr Tyr Phe Tyr Glu Lys Ala Gly Val Ser Thr Asp Thr Ala Phe Thr
385             390             395             400 ttc agt att atc caa tat tgt ctt ggt att gct gca acg ttt gta tcc    1248
Phe Ser Ile Ile Gln Tyr Cys Leu Gly Ile Ala Ala Thr Phe Val Ser
            405             410             415 tgg tgg gct tca aaa tat tgt ggc aga ttt gac ctt tat gct ttt ggg    1296
Trp Trp Ala Ser Lys Tyr Cys Gly Arg Phe Asp Leu Tyr Ala Phe Gly
        420             425             430 ctg gct ttt cag gct att atg ttc ttc att atc ggt ggt tta gga tgt    1344
Leu Ala Phe Gln Ala Ile Met Phe Phe Ile Ile Gly Gly Leu Gly Cys
            435             440             445 tca gac act cat ggc gct aaa atg ggt agt ggt gct ctt cta atg gtt    1392
Ser Asp Thr His Gly Ala Lys Met Gly Ser Gly Ala Leu Leu Met Val
450             455             460 gtc gcg ttc ttt tac aac ctc ggt att gca cct gtt gtt ttt tgc tta    1440
Val Ala Phe Phe Tyr Asn Leu Gly Ile Ala Pro Val Val Phe Cys Leu
465             470             475             480 gtg tct gaa atg ccg tct tca agg cta aga acc aaa aca att att ttg    1488
Val Ser Glu Met Pro Ser Ser Arg Leu Arg Thr Lys Thr Ile Ile Leu
            485             490             495 gct cgt aat gct tac aat gtg atc caa gtt gta gtt aca gtt ttg atc    1536
Ala Arg Asn Ala Tyr Asn Val Ile Gln Val Val Val Thr Val Leu Ile
        500             505             510 atg tac caa ttg aac tca gag aaa tgg aat tgg ggt gct aaa tca ggc    1584
Met Tyr Gln Leu Asn Ser Glu Lys Trp Asn Trp Gly Ala Lys Ser Gly
            515             520             525 ttt ttc tgg gga gga ttt tgt ctg gcc act tta gct tgg gct gtt gtc    1632
Phe Phe Trp Gly Gly Phe Cys Leu Ala Thr Leu Ala Trp Ala Val Val
530             535             540 gat tta cca gaa acc gct ggc agg act ttt att gag ata aat gaa ttg    1680
Asp Leu Pro Glu Thr Ala Gly Arg Thr Phe Ile Glu Ile Asn Glu Leu
545             550             555             560 ttt aga ctt ggt gtt cca gca aga aag ttc aag tcg act aaa gtc gac    1728
Phe Arg Leu Gly Val Pro Ala Arg Lys Phe Lys Ser Thr Lys Val Asp
            565             570             575 cct ttt gca gct gcc aaa gca gca gct gca gaa att aat gtt aaa gat    1776
Pro Phe Ala Ala Ala Lys Ala Ala Ala Ala Glu Ile Asn Val Lys Asp
        580             585             590 ccg aag gaa gat ttg gaa act tct gtg gta gat gaa ggg cga agc acc    1824
Pro Lys Glu Asp Leu Glu Thr Ser Val Val Asp Glu Gly Arg Ser Thr
            595             600             605 cca tct gtt gtg aac aaa                                            1842
Pro Ser Val Val Asn Lys
        610

<210> SEQ ID NO 28
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28
```

```
Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Asp Leu Ser
        35                  40                  45

His His Glu Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
                100                 105                 110

Glu Gly Tyr Asp Thr Ala Ile Leu Gly Ala Phe Tyr Ala Leu Pro Val
            115                 120                 125

Phe Gln Lys Lys Tyr Gly Ser Leu Asn Ser Asn Thr Gly Asp Tyr Glu
    130                 135                 140

Ile Ser Val Ser Trp Gln Ile Gly Leu Cys Leu Cys Tyr Met Ala Gly
145                 150                 155                 160

Glu Ile Val Gly Leu Gln Val Thr Gly Pro Ser Val Asp Tyr Met Gly
                165                 170                 175

Asn Arg Tyr Thr Leu Ile Met Ala Leu Phe Phe Leu Ala Ala Phe Ile
            180                 185                 190

Phe Ile Leu Tyr Phe Cys Lys Ser Leu Gly Met Ile Ala Val Gly Gln
    195                 200                 205

Ala Leu Cys Gly Met Pro Trp Gly Cys Phe Gln Cys Leu Thr Val Ser
    210                 215                 220

Tyr Ala Ser Glu Ile Cys Pro Leu Ala Leu Arg Tyr Tyr Leu Thr Thr
225                 230                 235                 240

Tyr Ser Asn Leu Cys Trp Thr Phe Gly Gln Leu Phe Ala Ala Gly Ile
            245                 250                 255

Met Lys Asn Ser Gln Asn Lys Tyr Ala Asn Ser Glu Leu Gly Tyr Lys
            260                 265                 270

Leu Pro Phe Ala Leu Gln Trp Ile Trp Pro Leu Pro Leu Ala Val Gly
    275                 280                 285

Ile Phe Leu Ala Pro Glu Ser Pro Trp Trp Leu Val Lys Lys Gly Arg
    290                 295                 300

Ile Asp Gln Ala Arg Arg Ser Leu Glu Arg Ile Leu Ser Gly Lys Gly
305                 310                 315                 320

Pro Glu Lys Glu Leu Leu Val Ser Met Glu Leu Asp Lys Ile Lys Thr
                325                 330                 335

Thr Ile Glu Lys Glu Gln Lys Met Ser Asp Glu Gly Thr Tyr Trp Asp
            340                 345                 350

Cys Val Lys Asp Gly Ile Asn Arg Arg Thr Arg Ile Ala Cys Leu
            355                 360                 365

Cys Trp Ile Gly Gln Cys Ser Cys Gly Ala Ser Leu Ile Gly Tyr Ser
    370                 375                 380

Thr Tyr Phe Tyr Glu Lys Ala Gly Val Ser Thr Asp Thr Ala Phe Thr
385                 390                 395                 400

Phe Ser Ile Ile Gln Tyr Cys Leu Gly Ile Ala Ala Thr Phe Val Ser
                405                 410                 415

Trp Trp Ala Ser Lys Tyr Cys Gly Arg Phe Asp Leu Tyr Ala Phe Gly
```

```
                      420                 425                 430
Leu Ala Phe Gln Ala Ile Met Phe Ile Ile Gly Gly Leu Gly Cys
                435                 440                 445
Ser Asp Thr His Gly Ala Lys Met Gly Ser Gly Ala Leu Leu Met Val
        450                 455                 460
Val Ala Phe Phe Tyr Asn Leu Gly Ile Ala Pro Val Val Phe Cys Leu
465                 470                 475                 480
Val Ser Glu Met Pro Ser Ser Arg Leu Arg Thr Lys Thr Ile Ile Leu
                485                 490                 495
Ala Arg Asn Ala Tyr Asn Val Ile Gln Val Val Thr Val Leu Ile
        500                 505                 510
Met Tyr Gln Leu Asn Ser Glu Lys Trp Asn Trp Gly Ala Lys Ser Gly
                515                 520                 525
Phe Phe Trp Gly Gly Phe Cys Leu Ala Thr Leu Ala Trp Ala Val Val
        530                 535                 540
Asp Leu Pro Glu Thr Ala Gly Arg Thr Phe Ile Glu Ile Asn Glu Leu
545                 550                 555                 560
Phe Arg Leu Gly Val Pro Ala Arg Lys Phe Lys Ser Thr Lys Val Asp
                565                 570                 575
Pro Phe Ala Ala Ala Lys Ala Ala Ala Glu Ile Asn Val Lys Asp
        580                 585                 590
Pro Lys Glu Asp Leu Glu Thr Ser Val Val Asp Glu Gly Arg Ser Thr
                595                 600                 605
Pro Ser Val Val Asn Lys
        610

<210> SEQ ID NO 29
<211> LENGTH: 1842
<212> TYPE: DNA
<213> ORGANISM: Artificial Sequence
<220> FEATURE:
<223> OTHER INFORMATION: Description of Artificial Sequence: Synthetic
      MAL61[D46G,L50H] polynucleotide
<220> FEATURE:
<221> NAME/KEY: CDS
<222> LOCATION: (1)..(1842)
<223> OTHER INFORMATION: Mal61p[Gly46, His50]

<400> SEQUENCE: 29 atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
            20                  25                  30 tcg ata gag atg gag gag caa ggt aag aaa agt gat ttt ggt ctt tcc     144
Ser Ile Glu Met Glu Glu Gln Gly Lys Lys Ser Asp Phe Gly Leu Ser
        35                  40                  45 cat cat gag tac ggt cca ggt tca cta ata cca aac gat aat aat gaa     192
His His Glu Tyr Gly Pro Gly Ser Leu Ile Pro Asn Asp Asn Asn Glu
    50                  55                  60 gaa gtc ccc gac ctt ctc gat gaa gct atg cag gac gcc aaa gag gca     240
Glu Val Pro Asp Leu Leu Asp Glu Ala Met Gln Asp Ala Lys Glu Ala
65                  70                  75                  80 gat gaa agt gag agg gga atg cca ctc atg aca gct ttg aag aca tat     288
Asp Glu Ser Glu Arg Gly Met Pro Leu Met Thr Ala Leu Lys Thr Tyr
                85                  90                  95 cca aaa gct gct gct tgg tca cta tta gtt tcc aca aca ttg att caa     336
Pro Lys Ala Ala Ala Trp Ser Leu Leu Val Ser Thr Thr Leu Ile Gln
            100                 105                 110
```

| | | |
|---|---|---|
| gag ggt tat gac aca gcc att cta gga gct ttc tat gcc ctg cct gtt<br>Glu Gly Tyr Asp Thr Ala Ile Leu Gly Ala Phe Tyr Ala Leu Pro Val<br>115                    120                    125 | 384 |
| ttt caa aaa aaa tat ggt tct ttg aat agc aat aca gga gat tat gaa<br>Phe Gln Lys Lys Tyr Gly Ser Leu Asn Ser Asn Thr Gly Asp Tyr Glu<br>130                    135                    140 | 432 |
| att tca gtt tcc tgg caa atc ggt cta tgt cta tgc tac atg gca ggt<br>Ile Ser Val Ser Trp Gln Ile Gly Leu Cys Leu Cys Tyr Met Ala Gly<br>145                    150                    155                    160 | 480 |
| gag att gtc ggt ttg caa gtg act ggg cct tct gta gat tac atg ggc<br>Glu Ile Val Gly Leu Gln Val Thr Gly Pro Ser Val Asp Tyr Met Gly<br>                    165                    170                    175 | 528 |
| aac cgt tac act ctg atc atg gcg ttg ttc ttt tta gcg gct ttc att<br>Asn Arg Tyr Thr Leu Ile Met Ala Leu Phe Phe Leu Ala Ala Phe Ile<br>                180                    185                    190 | 576 |
| ttc att ctg tat ttt tgc aag agt ttg ggt atg att gcc gtg gga cag<br>Phe Ile Leu Tyr Phe Cys Lys Ser Leu Gly Met Ile Ala Val Gly Gln<br>195                    200                    205 | 624 |
| gca ttg tgt ggt atg cca tgg ggt tgt ttc caa tgt ttg acc gtt tct<br>Ala Leu Cys Gly Met Pro Trp Gly Cys Phe Gln Cys Leu Thr Val Ser<br>          210                    215                    220 | 672 |
| tat gct tct gaa att tgt cct ttg gcc cta aga tac tat ttg acg act<br>Tyr Ala Ser Glu Ile Cys Pro Leu Ala Leu Arg Tyr Tyr Leu Thr Thr<br>225                    230                    235                    240 | 720 |
| tat tct aat tta tgt tgg acg ttc ggt caa ctt ttc gct gct ggt att<br>Tyr Ser Asn Leu Cys Trp Thr Phe Gly Gln Leu Phe Ala Ala Gly Ile<br>                245                    250                    255 | 768 |
| atg aaa aat tcc cag aac aaa tat gcc aac tca gaa cta gga tat aag<br>Met Lys Asn Ser Gln Asn Lys Tyr Ala Asn Ser Glu Leu Gly Tyr Lys<br>          260                    265                    270 | 816 |
| cta cct ttt gct ttg cag tgg atc tgg ccc ctt cct ttg gcg gta ggt<br>Leu Pro Phe Ala Leu Gln Trp Ile Trp Pro Leu Pro Leu Ala Val Gly<br>                275                    280                    285 | 864 |
| att ttt ttg gca cca gag tct cca tgg tgg ctg gtt aaa aaa gga agg<br>Ile Phe Leu Ala Pro Glu Ser Pro Trp Trp Leu Val Lys Lys Gly Arg<br>290                    295                    300 | 912 |
| att gat cag gcg agg aga tca ctt gaa aga ata tta agt ggt aaa gga<br>Ile Asp Gln Ala Arg Arg Ser Leu Glu Arg Ile Leu Ser Gly Lys Gly<br>305                    310                    315                    320 | 960 |
| ccc gag aaa gaa tta cta gtg agt atg gaa ctc gat aaa atc aaa act<br>Pro Glu Lys Glu Leu Leu Val Ser Met Glu Leu Asp Lys Ile Lys Thr<br>                325                    330                    335 | 1008 |
| act ata gaa aag gag cag aaa atg tct gat gaa gga act tac tgg gat<br>Thr Ile Glu Lys Glu Gln Lys Met Ser Asp Glu Gly Thr Tyr Trp Asp<br>                340                    345                    350 | 1056 |
| tgt gtg aaa gat ggt att aac agg aga aga acg aga ata gct tgt tta<br>Cys Val Lys Asp Gly Ile Asn Arg Arg Arg Thr Arg Ile Ala Cys Leu<br>          355                    360                    365 | 1104 |
| tgt tgg atc ggt caa tgc tcc tgt ggt gca tca tta att ggt tat tca<br>Cys Trp Ile Gly Gln Cys Ser Cys Gly Ala Ser Leu Ile Gly Tyr Ser<br>          370                    375                    380 | 1152 |
| act tac ttt tat gaa aaa gct ggt gtt agc act gat acg gct ttt act<br>Thr Tyr Phe Tyr Glu Lys Ala Gly Val Ser Thr Asp Thr Ala Phe Thr<br>385                    390                    395                    400 | 1200 |
| ttc agt att atc caa tat tgt ctt ggt att gct gca acg ttt gta tcc<br>Phe Ser Ile Ile Gln Tyr Cys Leu Gly Ile Ala Ala Thr Phe Val Ser<br>                405                    410                    415 | 1248 |
| tgg tgg gct tca aaa tat tgt ggc aga ttt gac ctt tat gct ttt ggg<br>Trp Trp Ala Ser Lys Tyr Cys Gly Arg Phe Asp Leu Tyr Ala Phe Gly<br>          420                    425                    430 | 1296 |

```
ctg gct ttt cag gct att atg ttc ttc att atc ggt ggt tta gga tgt    1344
Leu Ala Phe Gln Ala Ile Met Phe Phe Ile Ile Gly Gly Leu Gly Cys
        435                 440                 445 tca gac act cat ggc gct aaa atg ggt agt ggt gct ctt cta atg gtt    1392
Ser Asp Thr His Gly Ala Lys Met Gly Ser Gly Ala Leu Leu Met Val
    450                 455                 460 gtc gcg ttc ttt tac aac ctc ggt att gca cct gtt gtt ttt tgc tta    1440
Val Ala Phe Phe Tyr Asn Leu Gly Ile Ala Pro Val Val Phe Cys Leu
465                 470                 475                 480 gtg tct gaa atg ccg tct tca agg cta aga acc aaa aca att att ttg    1488
Val Ser Glu Met Pro Ser Ser Arg Leu Arg Thr Lys Thr Ile Ile Leu
                485                 490                 495 gct cgt aat gct tac aat gtg atc caa gtt gta gtt aca gtt ttg atc    1536
Ala Arg Asn Ala Tyr Asn Val Ile Gln Val Val Thr Val Leu Ile
            500                 505                 510 atg tac caa ttg aac tca gag aaa tgg aat tgg ggt gct aaa tca ggc    1584
Met Tyr Gln Leu Asn Ser Glu Lys Trp Asn Trp Gly Ala Lys Ser Gly
        515                 520                 525 ttt ttc tgg gga gga ttt tgt ctg gcc act tta gct tgg gct gtt gtc    1632
Phe Phe Trp Gly Gly Phe Cys Leu Ala Thr Leu Ala Trp Ala Val Val
    530                 535                 540 gat tta cca gaa acc gct ggc agg act ttt att gag ata aat gaa ttg    1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac    1728
Phe Arg Leu Gly Val Pro Ala Arg Lys Phe Lys Ser Thr Lys Val Asp
                565                 570                 575 cct ttt gca gct gcc aaa gca gca gct gca gaa att aat gtt aaa gat    1776
Pro Phe Ala Ala Ala Lys Ala Ala Ala Ala Glu Ile Asn Val Lys Asp
            580                 585                 590 ccg aag gaa gat ttg gaa act tct gtg gta gat gaa ggg cga agc acc    1824
Pro Lys Glu Asp Leu Glu Thr Ser Val Val Asp Glu Gly Arg Ser Thr
        595                 600                 605 cca tct gtt gtg aac aaa                                            1842
Pro Ser Val Val Asn Lys
    610

<210> SEQ ID NO 30
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Gly Leu Ser
        35                  40                  45

His His Glu Tyr Gly Pro Gly Ser Leu Ile Pro Asn Asp Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110
```

```
Glu Gly Tyr Asp Thr Ala Ile Leu Gly Ala Phe Tyr Ala Leu Pro Val
            115                 120                 125

Phe Gln Lys Lys Tyr Gly Ser Leu Asn Ser Asn Thr Gly Asp Tyr Glu
130                 135                 140

Ile Ser Val Ser Trp Gln Ile Gly Leu Cys Leu Cys Tyr Met Ala Gly
145                 150                 155                 160

Glu Ile Val Gly Leu Gln Val Thr Gly Pro Ser Val Asp Tyr Met Gly
            165                 170                 175

Asn Arg Tyr Thr Leu Ile Met Ala Leu Phe Phe Leu Ala Ala Phe Ile
            180                 185                 190

Phe Ile Leu Tyr Phe Cys Lys Ser Leu Gly Met Ile Ala Val Gly Gln
            195                 200                 205

Ala Leu Cys Gly Met Pro Trp Gly Cys Phe Gln Cys Leu Thr Val Ser
            210                 215                 220

Tyr Ala Ser Glu Ile Cys Pro Leu Ala Leu Arg Tyr Tyr Leu Thr Thr
225                 230                 235                 240

Tyr Ser Asn Leu Cys Trp Thr Phe Gly Gln Leu Phe Ala Ala Gly Ile
                245                 250                 255

Met Lys Asn Ser Gln Asn Lys Tyr Ala Asn Ser Glu Leu Gly Tyr Lys
            260                 265                 270

Leu Pro Phe Ala Leu Gln Trp Ile Trp Pro Leu Pro Leu Ala Val Gly
            275                 280                 285

Ile Phe Leu Ala Pro Glu Ser Pro Trp Trp Leu Val Lys Lys Gly Arg
            290                 295                 300

Ile Asp Gln Ala Arg Arg Ser Leu Glu Arg Ile Leu Ser Gly Lys Gly
305                 310                 315                 320

Pro Glu Lys Glu Leu Leu Val Ser Met Glu Leu Asp Lys Ile Lys Thr
                325                 330                 335

Thr Ile Glu Lys Glu Gln Lys Met Ser Asp Glu Gly Thr Tyr Trp Asp
            340                 345                 350

Cys Val Lys Asp Gly Ile Asn Arg Arg Thr Arg Ile Ala Cys Leu
            355                 360                 365

Cys Trp Ile Gly Gln Cys Ser Cys Gly Ala Ser Leu Ile Gly Tyr Ser
            370                 375                 380

Thr Tyr Phe Tyr Glu Lys Ala Gly Val Ser Thr Asp Thr Ala Phe Thr
385                 390                 395                 400

Phe Ser Ile Ile Gln Tyr Cys Leu Gly Ile Ala Ala Thr Phe Val Ser
                405                 410                 415

Trp Trp Ala Ser Lys Tyr Cys Gly Arg Phe Asp Leu Tyr Ala Phe Gly
                420                 425                 430

Leu Ala Phe Gln Ala Ile Met Phe Phe Ile Ile Gly Gly Leu Gly Cys
            435                 440                 445

Ser Asp Thr His Gly Ala Lys Met Gly Ser Gly Ala Leu Leu Met Val
450                 455                 460

Val Ala Phe Phe Tyr Asn Leu Gly Ile Ala Pro Val Val Phe Cys Leu
465                 470                 475                 480

Val Ser Glu Met Pro Ser Ser Arg Leu Arg Thr Lys Thr Ile Ile Leu
                485                 490                 495

Ala Arg Asn Ala Tyr Asn Val Ile Gln Val Val Thr Val Leu Ile
            500                 505                 510

Met Tyr Gln Leu Asn Ser Glu Lys Trp Asn Trp Gly Ala Lys Ser Gly
            515                 520                 525

Phe Phe Trp Gly Gly Phe Cys Leu Ala Thr Leu Ala Trp Ala Val Val
```

```
                530              535             540
Asp Leu Pro Glu Thr Ala Gly Arg Thr Phe Ile Glu Ile Asn Glu Leu
545                 550                 555                 560

Phe Arg Leu Gly Val Pro Ala Arg Lys Phe Lys Ser Thr Lys Val Asp
                565                 570                 575

Pro Phe Ala Ala Ala Lys Ala Ala Ala Glu Ile Asn Val Lys Asp
                580                 585                 590

Pro Lys Glu Asp Leu Glu Thr Ser Val Val Asp Glu Gly Arg Ser Thr
                595                 600                 605

Pro Ser Val Val Asn Lys
    610

<210> SEQ ID NO 31
<211> LENGTH: 1848
<212> TYPE: DNA
<213> ORGANISM: Artificial Sequence
<220> FEATURE:
<223> OTHER INFORMATION: Description of Artificial Sequence: Synthetic
      AGT1[E56K] polynucleotide
<220> FEATURE:
<221> NAME/KEY: CDS
<222> LOCATION: (1)..(1848)
<223> OTHER INFORMATION: Agt1p[Lys56]

<400> SEQUENCE: 31 atg aaa aat atc att tca ttg gta agc aag aag aag gct gcc tca aaa    48
Met Lys Asn Ile Ile Ser Leu Val Ser Lys Lys Lys Ala Ala Ser Lys
1               5                   10                  15 aat gag gat aaa aac att tct gag tct tca aga gat att gta aac caa    96
Asn Glu Asp Lys Asn Ile Ser Glu Ser Ser Arg Asp Ile Val Asn Gln
            20                  25                  30 cag gag gtt ttc aat act gaa gat ttt gaa gaa ggg aaa aag gat agt   144
Gln Glu Val Phe Asn Thr Glu Asp Phe Glu Glu Gly Lys Lys Asp Ser
        35                  40                  45 gcc ttt gag cta gac cac tta aag ttc acc acc aat tca gcc cag tta   192
Ala Phe Glu Leu Asp His Leu Lys Phe Thr Thr Asn Ser Ala Gln Leu
    50                  55                  60 gga gat tct gac gaa gat aac gag aat gtg att aat gag atg aac gct   240
Gly Asp Ser Asp Glu Asp Asn Glu Asn Val Ile Asn Glu Met Asn Ala
65                  70                  75                  80 act gat gat gca aat gaa gct aac agc gag gaa aaa agc atg act ttg   288
Thr Asp Asp Ala Asn Glu Ala Asn Ser Glu Glu Lys Ser Met Thr Leu
                85                  90                  95 aag cag gcg ttg cta aaa tat cca aaa gca gcc ctg tgg tcc ata tta   336
Lys Gln Ala Leu Leu Lys Tyr Pro Lys Ala Ala Leu Trp Ser Ile Leu
            100                 105                 110 gtg tct act acc ctg gtt atg gaa ggt tat gat acc gca cta ctg agc   384
Val Ser Thr Thr Leu Val Met Glu Gly Tyr Asp Thr Ala Leu Leu Ser
        115                 120                 125 gca ctg tat gcc ctg cca gtt ttt cag aga aaa ttc ggt act ttg aac   432
Ala Leu Tyr Ala Leu Pro Val Phe Gln Arg Lys Phe Gly Thr Leu Asn
    130                 135                 140 ggg gag ggt tct tac gaa att act tcc caa tgg cag att ggt tta aac   480
Gly Glu Gly Ser Tyr Glu Ile Thr Ser Gln Trp Gln Ile Gly Leu Asn
145                 150                 155                 160 atg tgt gtc ctt tgt ggt gag atg att ggt ttg caa atc acg act tat   528
Met Cys Val Leu Cys Gly Glu Met Ile Gly Leu Gln Ile Thr Thr Tyr
                165                 170                 175 atg gtt gaa ttt atg ggg aat cgt tat acg atg att aca gca ctt ggt   576
Met Val Glu Phe Met Gly Asn Arg Tyr Thr Met Ile Thr Ala Leu Gly
            180                 185                 190
```

```
ttg tta act gct tat atc ttt atc ctc tac tac tgt aaa agt tta gct      624
Leu Leu Thr Ala Tyr Ile Phe Ile Leu Tyr Tyr Cys Lys Ser Leu Ala
            195                 200                 205 atg att gct gtg gga caa att ctc tca gct ata cca tgg ggt tgt ttc      672
Met Ile Ala Val Gly Gln Ile Leu Ser Ala Ile Pro Trp Gly Cys Phe
    210                 215                 220 caa agt ttg gct gtt act tat gct tcg gaa gtt tgc cct tta gca tta      720
Gln Ser Leu Ala Val Thr Tyr Ala Ser Glu Val Cys Pro Leu Ala Leu
225                 230                 235                 240 aga tat tac atg acc agt tac tcc aac att tgt tgg tta ttt ggt caa      768
Arg Tyr Tyr Met Thr Ser Tyr Ser Asn Ile Cys Trp Leu Phe Gly Gln
                245                 250                 255 atc ttc gcc tct ggt att atg aaa aac tca caa gag aat tta ggg aac      816
Ile Phe Ala Ser Gly Ile Met Lys Asn Ser Gln Glu Asn Leu Gly Asn
            260                 265                 270 tcc gac ttg ggc tat aaa ttg cca ttt gct tta caa tgg att tgg cct      864
Ser Asp Leu Gly Tyr Lys Leu Pro Phe Ala Leu Gln Trp Ile Trp Pro
        275                 280                 285 gct cct tta atg atc ggt atc ttt ttc gct cct gag tcg ccc tgg tgg      912
Ala Pro Leu Met Ile Gly Ile Phe Phe Ala Pro Glu Ser Pro Trp Trp
    290                 295                 300 ttg gtg aga aag gat agg gtc gct gag gca aga aaa tct tta agc aga      960
Leu Val Arg Lys Asp Arg Val Ala Glu Ala Arg Lys Ser Leu Ser Arg
305                 310                 315                 320 att ttg agt ggt aaa ggc gcc gag aag gac att caa gtt gat ctt act     1008
Ile Leu Ser Gly Lys Gly Ala Glu Lys Asp Ile Gln Val Asp Leu Thr
                325                 330                 335 tta aag cag att gaa ttg act att gaa aaa gaa aga ctt tta gca tct     1056
Leu Lys Gln Ile Glu Leu Thr Ile Glu Lys Glu Arg Leu Leu Ala Ser
            340                 345                 350 aaa tca gga tca ttc ttt aat tgt ttc aag gga gtt aat gga aga aga     1104
Lys Ser Gly Ser Phe Phe Asn Cys Phe Lys Gly Val Asn Gly Arg Arg
        355                 360                 365 acg aga ctt gca tgt tta act tgg gta gct caa aat agt agc ggt gcc     1152
Thr Arg Leu Ala Cys Leu Thr Trp Val Ala Gln Asn Ser Ser Gly Ala
    370                 375                 380 gtt tta ctt ggt tac tcg aca tat ttt ttt gaa aga gca ggt atg gcc     1200
Val Leu Leu Gly Tyr Ser Thr Tyr Phe Phe Glu Arg Ala Gly Met Ala
385                 390                 395                 400 acc gac aag gcg ttt act ttt tct cta att cag tac tgt ctt ggg tta     1248
Thr Asp Lys Ala Phe Thr Phe Ser Leu Ile Gln Tyr Cys Leu Gly Leu
                405                 410                 415 gcg ggt aca ctt tgc tcc tgg gta ata tct ggc cgt gtt ggt aga tgg     1296
Ala Gly Thr Leu Cys Ser Trp Val Ile Ser Gly Arg Val Gly Arg Trp
            420                 425                 430 aca ata ctg acc tat ggt ctt gca ttt caa atg gtc tgc tta ttt att     1344
Thr Ile Leu Thr Tyr Gly Leu Ala Phe Gln Met Val Cys Leu Phe Ile
        435                 440                 445 att ggt gga atg ggt ttt ggt tct gga agc agc gct agt aat ggt gcc     1392
Ile Gly Gly Met Gly Phe Gly Ser Gly Ser Ser Ala Ser Asn Gly Ala
    450                 455                 460 ggt ggt tta ttg ctg gct tta tca ttc ttt tac aat gct ggt atc ggt     1440
Gly Gly Leu Leu Leu Ala Leu Ser Phe Phe Tyr Asn Ala Gly Ile Gly
465                 470                 475                 480 gca gtt gtt tac tgt atc gtt gct gaa att cca tca gcg gag ttg aga     1488
Ala Val Val Tyr Cys Ile Val Ala Glu Ile Pro Ser Ala Glu Leu Arg
                485                 490                 495 act aag act ata gtg ctg gcc cgt att tgc tac aat ctc atg gcc gtt     1536
Thr Lys Thr Ile Val Leu Ala Arg Ile Cys Tyr Asn Leu Met Ala Val
            500                 505                 510
```

```
att aac gct ata tta acg ccc tat atg cta aac gtg agc gat tgg aac      1584
Ile Asn Ala Ile Leu Thr Pro Tyr Met Leu Asn Val Ser Asp Trp Asn
        515                 520                 525 tgg ggt gcc aaa act ggt cta tac tgg ggt ggt ttc aca gca gtc act      1632
Trp Gly Ala Lys Thr Gly Leu Tyr Trp Gly Gly Phe Thr Ala Val Thr
530                 535                 540 tta gct tgg gtc atc atc gat ctg cct gag aca act ggt aga acc ttc      1680
Leu Ala Trp Val Ile Ile Asp Leu Pro Glu Thr Thr Gly Arg Thr Phe
545                 550                 555                 560 agt gaa att aat gaa ctt ttc aac caa ggg gtt cct gcc aga aaa ttt      1728
Ser Glu Ile Asn Glu Leu Phe Asn Gln Gly Val Pro Ala Arg Lys Phe
                565                 570                 575 gca tct act gtg gtt gat cca ttc gga aag gga aaa act caa cat gat      1776
Ala Ser Thr Val Val Asp Pro Phe Gly Lys Gly Lys Thr Gln His Asp
            580                 585                 590 tcg cta gct gat gag agt atc agt cag tcc tca agc ata aaa cag cga      1824
Ser Leu Ala Asp Glu Ser Ile Ser Gln Ser Ser Ser Ile Lys Gln Arg
        595                 600                 605 gaa tta aat gca gct gat aaa tgt                                      1848
Glu Leu Asn Ala Ala Asp Lys Cys
    610                 615

<210> SEQ ID NO 32
<211> LENGTH: 616
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
                20                  25                  30

Gln Glu Val Phe Asn Thr Glu Asp Phe Glu Glu Gly Lys Lys Asp Ser
            35                  40                  45

Ala Phe Glu Leu Asp His Leu Lys Phe Thr Thr Asn Ser Ala Gln Leu
        50                  55                  60

Gly Asp Ser Asp Glu Asp Asn Glu Asn Val Ile Asn Glu Met Asn Ala
65                  70                  75                  80

Thr Asp Asp Ala Asn Glu Ala Asn Ser Glu Glu Lys Ser Met Thr Leu
                85                  90                  95

Lys Gln Ala Leu Leu Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
        115                 120                 125

Ala Leu Tyr Ala Leu Pro Val Phe Gln Arg Lys Phe Gly Thr Leu Asn
    130                 135                 140

Gly Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
            180                 185                 190

Leu Leu Thr Ala Tyr Ile Phe Ile Leu Tyr Tyr Cys Lys Ser Leu Ala
        195                 200                 205

Met Ile Ala Val Gly Gln Ile Leu Ser Ala Ile Pro Trp Gly Cys Phe
    210                 215                 220
```

```
Gln Ser Leu Ala Val Thr Tyr Ala Ser Glu Val Cys Pro Leu Ala Leu
225                 230                 235                 240

Arg Tyr Met Thr Ser Tyr Ser Asn Ile Cys Trp Leu Phe Gly Gln
            245                 250                 255

Ile Phe Ala Ser Gly Ile Met Lys Asn Ser Gln Glu Asn Leu Gly Asn
                260                 265                 270

Ser Asp Leu Gly Tyr Lys Leu Pro Phe Ala Leu Gln Trp Ile Trp Pro
            275                 280                 285

Ala Pro Leu Met Ile Gly Ile Phe Phe Ala Pro Glu Ser Pro Trp Trp
            290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Val Asp Leu Thr
                325                 330                 335

Leu Lys Gln Ile Glu Leu Thr Ile Glu Lys Glu Arg Leu Leu Ala Ser
            340                 345                 350

Lys Ser Gly Ser Phe Phe Asn Cys Phe Lys Gly Val Asn Gly Arg Arg
            355                 360                 365

Thr Arg Leu Ala Cys Leu Thr Trp Val Ala Gln Asn Ser Ser Gly Ala
370                 375                 380

Val Leu Leu Gly Tyr Ser Thr Tyr Phe Glu Arg Ala Gly Met Ala
385                 390                 395                 400

Thr Asp Lys Ala Phe Thr Phe Ser Leu Ile Gln Tyr Cys Leu Gly Leu
                405                 410                 415

Ala Gly Thr Leu Cys Ser Trp Val Ile Ser Arg Val Gly Arg Trp
            420                 425                 430

Thr Ile Leu Thr Tyr Gly Leu Ala Phe Gln Met Val Cys Leu Phe Ile
            435                 440                 445

Ile Gly Gly Met Gly Phe Gly Ser Gly Ser Ser Ala Ser Asn Gly Ala
                450                 455                 460

Gly Gly Leu Leu Leu Ala Leu Ser Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
            500                 505                 510

Ile Asn Ala Ile Leu Thr Pro Tyr Met Leu Asn Val Ser Asp Trp Asn
            515                 520                 525

Trp Gly Ala Lys Thr Gly Leu Tyr Trp Gly Gly Phe Thr Ala Val Thr
            530                 535                 540

Leu Ala Trp Val Ile Ile Asp Leu Pro Glu Thr Thr Gly Arg Thr Phe
545                 550                 555                 560

Ser Glu Ile Asn Glu Leu Phe Asn Gln Gly Val Pro Ala Arg Lys Phe
                565                 570                 575

Ala Ser Thr Val Val Asp Pro Phe Gly Lys Gly Lys Thr Gln His Asp
            580                 585                 590

Ser Leu Ala Asp Glu Ser Ile Ser Gln Ser Ser Ile Lys Gln Arg
            595                 600                 605

Glu Leu Asn Ala Ala Asp Lys Cys
    610                 615

<210> SEQ ID NO 33
<211> LENGTH: 1848
<212> TYPE: DNA
```

-continued

<213> ORGANISM: Artificial Sequence
<220> FEATURE:
<223> OTHER INFORMATION: Description of Artificial Sequence: Synthetic AGT1[E56G] polynucleotide
<220> FEATURE:
<221> NAME/KEY: CDS
<222> LOCATION: (1)..(1848)
<223> OTHER INFORMATION: Agt1p[Gly56]

<400> SEQUENCE: 33

```
atg aaa aat atc att tca ttg gta agc aag aag aag gct gcc tca aaa      48
Met Lys Asn Ile Ile Ser Leu Val Ser Lys Lys Lys Ala Ala Ser Lys
1               5                   10                  15 aat gag gat aaa aac att tct gag tct tca aga gat att gta aac caa      96
Asn Glu Asp Lys Asn Ile Ser Glu Ser Ser Arg Asp Ile Val Asn Gln
            20                  25                  30 cag gag gtt ttc aat act gaa gat ttt gaa gaa ggg aaa aag gat agt     144
Gln Glu Val Phe Asn Thr Glu Asp Phe Glu Glu Gly Lys Lys Asp Ser
        35                  40                  45 gcc ttt gag cta gac cac tta ggg ttc acc acc aat tca gcc cag tta     192
Ala Phe Glu Leu Asp His Leu Gly Phe Thr Thr Asn Ser Ala Gln Leu
    50                  55                  60 gga gat tct gac gaa gat aac gag aat gtg att aat gag atg aac gct     240
Gly Asp Ser Asp Glu Asp Asn Glu Asn Val Ile Asn Glu Met Asn Ala
65                  70                  75                  80 act gat gat gca aat gaa gct aac agc gag gaa aaa agc atg act ttg     288
Thr Asp Asp Ala Asn Glu Ala Asn Ser Glu Glu Lys Ser Met Thr Leu
                85                  90                  95 aag cag gcg ttg cta aaa tat cca aaa gca gcc ctg tgg tcc ata tta     336
Lys Gln Ala Leu Leu Lys Tyr Pro Lys Ala Ala Leu Trp Ser Ile Leu
            100                 105                 110 gtg tct act acc ctg gtt atg gaa ggt tat gat acc gca cta ctg agc     384
Val Ser Thr Thr Leu Val Met Glu Gly Tyr Asp Thr Ala Leu Leu Ser
        115                 120                 125 gca ctg tat gcc ctg cca gtt ttt cag aga aaa ttc ggt act ttg aac     432
Ala Leu Tyr Ala Leu Pro Val Phe Gln Arg Lys Phe Gly Thr Leu Asn
    130                 135                 140 ggg gag ggt tct tac gaa att act tcc caa tgg cag att ggt tta aac     480
Gly Glu Gly Ser Tyr Glu Ile Thr Ser Gln Trp Gln Ile Gly Leu Asn
145                 150                 155                 160 atg tgt gtc ctt tgt ggt gag atg att ggt ttg caa atc acg act tat     528
Met Cys Val Leu Cys Gly Glu Met Ile Gly Leu Gln Ile Thr Thr Tyr
                165                 170                 175 atg gtt gaa ttt atg ggg aat cgt tat acg atg att aca gca ctt ggt     576
Met Val Glu Phe Met Gly Asn Arg Tyr Thr Met Ile Thr Ala Leu Gly
            180                 185                 190 ttg tta act gct tat atc ttt atc ctc tac tac tgt aaa agt tta gct     624
Leu Leu Thr Ala Tyr Ile Phe Ile Leu Tyr Tyr Cys Lys Ser Leu Ala
        195                 200                 205 atg att gct gtg gga caa att ctc tca gct ata cca tgg ggt tgt ttc     672
Met Ile Ala Val Gly Gln Ile Leu Ser Ala Ile Pro Trp Gly Cys Phe
    210                 215                 220 caa agt ttg gct gtt act tat gct tcg gaa gtt tgc cct tta gca tta     720
Gln Ser Leu Ala Val Thr Tyr Ala Ser Glu Val Cys Pro Leu Ala Leu
225                 230                 235                 240 aga tat tac atg acc agt tac tcc aac att tgt tgg tta ttt ggt caa     768
Arg Tyr Tyr Met Thr Ser Tyr Ser Asn Ile Cys Trp Leu Phe Gly Gln
                245                 250                 255 atc ttc gcc tct ggt att atg aaa aac tca caa gag aat tta ggg aac     816
Ile Phe Ala Ser Gly Ile Met Lys Asn Ser Gln Glu Asn Leu Gly Asn
            260                 265                 270 tcc gac ttg ggc tat aaa ttg cca ttt gct tta caa tgg att tgg cct     864
```

```
Ser Asp Leu Gly Tyr Lys Leu Pro Phe Ala Leu Gln Trp Ile Trp Pro
        275                 280                 285 gct cct tta atg atc ggt atc ttt ttc gct cct gag tcg ccc tgg tgg      912
Ala Pro Leu Met Ile Gly Ile Phe Phe Ala Pro Glu Ser Pro Trp Trp
290                 295                 300 ttg gtg aga aag gat agg gtc gct gag gca aga aaa tct tta agc aga      960
Leu Val Arg Lys Asp Arg Val Ala Glu Ala Arg Lys Ser Leu Ser Arg
305                 310                 315                 320 att ttg agt ggt aaa ggc gcc gag aag gac att caa gtt gat ctt act     1008
Ile Leu Ser Gly Lys Gly Ala Glu Lys Asp Ile Gln Val Asp Leu Thr
            325                 330                 335 tta aag cag att gaa ttg act att gaa aaa gaa aga ctt tta gca tct     1056
Leu Lys Gln Ile Glu Leu Thr Ile Glu Lys Glu Arg Leu Leu Ala Ser
        340                 345                 350 aaa tca gga tca ttc ttt aat tgt ttc aag gga gtt aat gga aga aga     1104
Lys Ser Gly Ser Phe Phe Asn Cys Phe Lys Gly Val Asn Gly Arg Arg
355                 360                 365 acg aga ctt gca tgt tta act tgg gta gct caa aat agt agc ggt gcc     1152
Thr Arg Leu Ala Cys Leu Thr Trp Val Ala Gln Asn Ser Ser Gly Ala
370                 375                 380 gtt tta ctt ggt tac tcg aca tat ttt ttt gaa aga gca ggt atg gcc     1200
Val Leu Leu Gly Tyr Ser Thr Tyr Phe Phe Glu Arg Ala Gly Met Ala
385                 390                 395                 400 acc gac aag gcg ttt act ttt tct cta att cag tac tgt ctt ggg tta     1248
Thr Asp Lys Ala Phe Thr Phe Ser Leu Ile Gln Tyr Cys Leu Gly Leu
            405                 410                 415 gcg ggt aca ctt tgc tcc tgg gta ata tct ggc cgt gtt ggt aga tgg     1296
Ala Gly Thr Leu Cys Ser Trp Val Ile Ser Gly Arg Val Gly Arg Trp
        420                 425                 430 aca ata ctg acc tat ggt ctt gca ttt caa atg gtc tgc tta ttt att     1344
Thr Ile Leu Thr Tyr Gly Leu Ala Phe Gln Met Val Cys Leu Phe Ile
435                 440                 445 att ggt gga atg ggt ttt ggt tct gga agc agc gct agt aat ggt gcc     1392
Ile Gly Gly Met Gly Phe Gly Ser Gly Ser Ser Ala Ser Asn Gly Ala
450                 455                 460 ggt ggt tta ttg ctg gct tta tca ttc ttt tac aat gct ggt atc ggt     1440
Gly Gly Leu Leu Leu Ala Leu Ser Phe Phe Tyr Asn Ala Gly Ile Gly
465                 470                 475                 480 gca gtt gtt tac tgt atc gtt gct gaa att cca tca gcg gag ttg aga     1488
Ala Val Val Tyr Cys Ile Val Ala Glu Ile Pro Ser Ala Glu Leu Arg
            485                 490                 495 act aag act ata gtg ctg gcc cgt att tgc tac aat ctc atg gcc gtt     1536
Thr Lys Thr Ile Val Leu Ala Arg Ile Cys Tyr Asn Leu Met Ala Val
        500                 505                 510 att aac gct ata tta acg ccc tat atg cta aac gtg agc gat tgg aac     1584
Ile Asn Ala Ile Leu Thr Pro Tyr Met Leu Asn Val Ser Asp Trp Asn
515                 520                 525 tgg ggt gcc aaa act ggt cta tac tgg ggt ggt ttc aca gca gtc act     1632
Trp Gly Ala Lys Thr Gly Leu Tyr Trp Gly Gly Phe Thr Ala Val Thr
530                 535                 540 tta gct tgg gtc atc atc gat ctg cct gag aca act ggt aga acc ttc     1680
Leu Ala Trp Val Ile Ile Asp Leu Pro Glu Thr Thr Gly Arg Thr Phe
545                 550                 555                 560 agt gaa att aat gaa ctt ttc aac caa ggg gtt cct gcc aga aaa ttt     1728
Ser Glu Ile Asn Glu Leu Phe Asn Gln Gly Val Pro Ala Arg Lys Phe
            565                 570                 575 gca tct act gtg gtt gat cca ttc gga aag gga aaa act caa cat gat     1776
Ala Ser Thr Val Val Asp Pro Phe Gly Lys Gly Lys Thr Gln His Asp
        580                 585                 590 tcg cta gct gat gag agt atc agt cag tcc tca agc ata aaa cag cga    1824
```

```
Ser Leu Ala Asp Glu Ser Ile Ser Gln Ser Ser Ile Lys Gln Arg
        595                 600                 605 gaa tta aat gca gct gat aaa tgt                                      1848
Glu Leu Asn Ala Ala Asp Lys Cys
    610                 615
```

<210> SEQ ID NO 34
<211> LENGTH: 616
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asp Phe Glu Gly Lys Lys Asp Ser
        35                  40                  45

Ala Phe Glu Leu Asp His Leu Gly Phe Thr Thr Asn Ser Ala Gln Leu
    50                  55                  60

Gly Asp Ser Asp Glu Asp Asn Glu Asn Val Ile Asn Glu Met Asn Ala
65                  70                  75                  80

Thr Asp Asp Ala Asn Glu Ala Asn Ser Glu Glu Lys Ser Met Thr Leu
                85                  90                  95

Lys Gln Ala Leu Leu Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
        115                 120                 125

Ala Leu Tyr Ala Leu Pro Val Phe Gln Arg Lys Phe Gly Thr Leu Asn
    130                 135                 140

Gly Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
            180                 185                 190

Leu Leu Thr Ala Tyr Ile Phe Ile Leu Tyr Tyr Cys Lys Ser Leu Ala
        195                 200                 205

Met Ile Ala Val Gly Gln Ile Leu Ser Ala Ile Pro Trp Gly Cys Phe
    210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285

Ala Pro Leu Met Ile Gly Ile Phe Phe Ala Pro Glu Ser Pro Trp Trp
    290                 295                 300

Leu Val Arg Lys Asp Arg Val Ala Glu Ala Lys Ser Leu Ser Arg
305                 310                 315                 320

Ile Leu Ser Gly Lys Gly Ala Glu Lys Asp Ile Gln Val Asp Leu Thr
                325                 330                 335
```

```
Leu Lys Gln Ile Glu Leu Thr Ile Glu Lys Glu Arg Leu Leu Ala Ser
            340                 345                 350

Lys Ser Gly Ser Phe Phe Asn Cys Phe Lys Gly Val Asn Gly Arg Arg
        355                 360                 365

Thr Arg Leu Ala Cys Leu Thr Trp Val Ala Gln Asn Ser Ser Gly Ala
370                 375                 380

Val Leu Leu Gly Tyr Ser Thr Tyr Phe Glu Arg Ala Gly Met Ala
385                 390                 395                 400

Thr Asp Lys Ala Phe Thr Phe Ser Leu Ile Gln Tyr Cys Leu Gly Leu
                405                 410                 415

Ala Gly Thr Leu Cys Ser Trp Val Ile Ser Gly Arg Val Gly Arg Trp
            420                 425                 430

Thr Ile Leu Thr Tyr Gly Leu Ala Phe Gln Met Val Cys Leu Phe Ile
            435                 440                 445

Ile Gly Gly Met Gly Phe Gly Ser Gly Ser Ser Ala Ser Asn Gly Ala
450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
            500                 505                 510

Ile Asn Ala Ile Leu Thr Pro Tyr Met Leu Asn Val Ser Asp Trp Asn
            515                 520                 525

Trp Gly Ala Lys Thr Gly Leu Tyr Trp Gly Gly Phe Thr Ala Val Thr
            530                 535                 540

Leu Ala Trp Val Ile Ile Asp Leu Pro Glu Thr Thr Gly Arg Thr Phe
545                 550                 555                 560

Ser Glu Ile Asn Glu Leu Phe Asn Gln Gly Val Pro Ala Arg Lys Phe
                565                 570                 575

Ala Ser Thr Val Val Asp Pro Phe Gly Lys Gly Lys Thr Gln His Asp
            580                 585                 590

Ser Leu Ala Asp Glu Ser Ile Ser Gln Ser Ser Ile Lys Gln Arg
            595                 600                 605

Glu Leu Asn Ala Ala Asp Lys Cys
        610                 615

<210> SEQ ID NO 35
<211> LENGTH: 1845
<212> TYPE: DNA
<213> ORGANISM: Artificial Sequence
<220> FEATURE:
<223> OTHER INFORMATION: Description of Artificial Sequence: Synthetic
      MTT1[D46G] polynucleotide
<220> FEATURE:
<221> NAME/KEY: CDS
<222> LOCATION: (1)..(1845)
<223> OTHER INFORMATION: Mtt1p[Gly46]

<400> SEQUENCE: 35 atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
                20                  25                  30 tcg ata gag atg gag gag caa ggt aag aaa agt gat ttt ggt ctt tcc     144
Ser Ile Glu Met Glu Glu Gln Gly Lys Lys Ser Asp Phe Gly Leu Ser
```

-continued

```
                 35                  40                  45
cat cat gag tac ggt cca ggt tca cta aca cca aac gat aat aat gaa         192
His His Glu Tyr Gly Pro Gly Ser Leu Thr Pro Asn Asp Asn Asn Glu
 50                  55                  60 gaa gtc ccc gac ctt ctc gat gaa gct atg cag gac gcc aaa gag gca         240
Glu Val Pro Asp Leu Leu Asp Glu Ala Met Gln Asp Ala Lys Glu Ala
 65                  70                  75                  80 gat gaa agt gag agg gga atg cca ctc atg aca gct ttg aag aca tat         288
Asp Glu Ser Glu Arg Gly Met Pro Leu Met Thr Ala Leu Lys Thr Tyr
                 85                  90                  95 cca aaa gct gct gct tgg tca cta tta gtt tcc aca aca ttg att caa         336
Pro Lys Ala Ala Ala Trp Ser Leu Leu Val Ser Thr Thr Leu Ile Gln
            100                 105                 110 gag ggt tat gac aca gcc att cta gga tct ttc tat gcc ctg cct gtt         384
Glu Gly Tyr Asp Thr Ala Ile Leu Gly Ser Phe Tyr Ala Leu Pro Val
            115                 120                 125 ttt caa aaa aaa tat ggt tct ttg aat agc aat aca gga gat tat gaa         432
Phe Gln Lys Lys Tyr Gly Ser Leu Asn Ser Asn Thr Gly Asp Tyr Glu
130                 135                 140 att tca gct tcc tgg caa att ggc ttg tcc tta tgc gtt acg gct ggt         480
Ile Ser Ala Ser Trp Gln Ile Gly Leu Ser Leu Cys Val Thr Ala Gly
145                 150                 155                 160 gaa att gta ggt ttg caa atg act ggg cct ttt gta gat tat atg ggt         528
Glu Ile Val Gly Leu Gln Met Thr Gly Pro Phe Val Asp Tyr Met Gly
                165                 170                 175 aat cgc tat aca ttg att ctg gca ttg att ctt ctt gct gca ttc acc         576
Asn Arg Tyr Thr Leu Ile Leu Ala Leu Ile Leu Leu Ala Ala Phe Thr
            180                 185                 190 ttt att ctg tat ttt tgc aag ggt ttg ggt atg att gct gtg gga caa         624
Phe Ile Leu Tyr Phe Cys Lys Gly Leu Gly Met Ile Ala Val Gly Gln
            195                 200                 205 gta ttg tgt ggt atg cca tgg ggt tgt ttc caa tgt ttg acc gtt tct         672
Val Leu Cys Gly Met Pro Trp Gly Cys Phe Gln Cys Leu Thr Val Ser
210                 215                 220 tat gct tct gaa att tgt cct atg gcc cta aga tac tat ttg acg act         720
Tyr Ala Ser Glu Ile Cys Pro Met Ala Leu Arg Tyr Tyr Leu Thr Thr
225                 230                 235                 240 tat tct aat tta tgt tgg acg ttc ggt caa ctt ttc gct gct ggt att         768
Tyr Ser Asn Leu Cys Trp Thr Phe Gly Gln Leu Phe Ala Ala Gly Ile
                245                 250                 255 atg aaa aac tcc caa aat aag tac cct aac tca gaa cta gga tat aag         816
Met Lys Asn Ser Gln Asn Lys Tyr Pro Asn Ser Glu Leu Gly Tyr Lys
            260                 265                 270 cta cct ttt gct ttg cag tgg atc tgg cct gct cct ctt gca ata ggt         864
Leu Pro Phe Ala Leu Gln Trp Ile Trp Pro Ala Pro Leu Ala Ile Gly
            275                 280                 285 att ttt ttt gca cca gag tct cca tgg tgg ctg gtt aaa aaa gga agg         912
Ile Phe Phe Ala Pro Glu Ser Pro Trp Trp Leu Val Lys Lys Gly Arg
            290                 295                 300 att gat caa gca agg aga tca ctt gaa aga aca ttg agt ggt aaa gga         960
Ile Asp Gln Ala Arg Arg Ser Leu Glu Arg Thr Leu Ser Gly Lys Gly
305                 310                 315                 320 ccc gag aag gaa tta ctg gta agt atg gag cta gat aat atc aaa gta        1008
Pro Glu Lys Glu Leu Leu Val Ser Met Glu Leu Asp Asn Ile Lys Val
                325                 330                 335 acc att gaa aag gaa aaa aag ctg tca gac tca gaa ggt tcc tat tgg        1056
Thr Ile Glu Lys Glu Lys Lys Leu Ser Asp Ser Glu Gly Ser Tyr Trp
            340                 345                 350 gat tgt ctg aag gac agt gtt aat agg aga aga acg aga ata gct tgt        1104
Asp Cys Leu Lys Asp Ser Val Asn Arg Arg Arg Thr Arg Ile Ala Cys
```

| | | | | | | | | | | | | | | | |
|---|---|---|---|---|---|---|---|---|---|---|---|---|---|---|---|
| | | | | 355 | | | | 360 | | | | | 365 | | |
| tta | tgt | tgg | gtc | ggt | caa | acc | acc | tgt | ggt | aca | tca | tta | att | ggt | aat | 1152 |
| Leu | Cys | Trp | Val | Gly | Gln | Thr | Thr | Cys | Gly | Thr | Ser | Leu | Ile | Gly | Asn | |
| | 370 | | | | | 375 | | | | | 380 | | | | | |
| tca | act | tac | ttt | tat | gaa | aaa | gct | gga | gtt | ggt | act | gat | acg | gct | ttc | 1200 |
| Ser | Thr | Tyr | Phe | Tyr | Glu | Lys | Ala | Gly | Val | Gly | Thr | Asp | Thr | Ala | Phe | |
| 385 | | | | | 390 | | | | | 395 | | | | | 400 | |
| act | ttc | agt | att | atc | caa | tat | tgt | ctt | ggt | att | gcc | gca | aca | ttt | ctt | 1248 |
| Thr | Phe | Ser | Ile | Ile | Gln | Tyr | Cys | Leu | Gly | Ile | Ala | Ala | Thr | Phe | Leu | |
| | | | | 405 | | | | | 410 | | | | | 415 | | |
| tct | tgg | tgg | gct | tca | aaa | tat | ttt | ggt | agg | ttt | gac | ctt | tac | gca | ttc | 1296 |
| Ser | Trp | Trp | Ala | Ser | Lys | Tyr | Phe | Gly | Arg | Phe | Asp | Leu | Tyr | Ala | Phe | |
| | | | 420 | | | | | 425 | | | | | 430 | | | |
| gga | ttg | gct | ata | caa | aca | gtt | tca | ttg | ttt | atc | ata | gga | ggt | ttg | gga | 1344 |
| Gly | Leu | Ala | Ile | Gln | Thr | Val | Ser | Leu | Phe | Ile | Ile | Gly | Gly | Leu | Gly | |
| | | | | 435 | | | | | 440 | | | | | 445 | | |
| tgc | tcc | gac | tcg | cat | ggc | gct | gaa | atg | gga | agt | ggt | tct | ctt | tta | atg | 1392 |
| Cys | Ser | Asp | Ser | His | Gly | Ala | Glu | Met | Gly | Ser | Gly | Ser | Leu | Leu | Met | |
| | 450 | | | | | 455 | | | | | 460 | | | | | |
| gtt | ctt | tcc | ttc | ttc | tac | aat | ttg | ggt | att | gct | ccc | gtt | gtg | ttt | tgc | 1440 |
| Val | Leu | Ser | Phe | Phe | Tyr | Asn | Leu | Gly | Ile | Ala | Pro | Val | Val | Phe | Cys | |
| 465 | | | | | 470 | | | | | 475 | | | | | 480 | |
| tta | gtg | tcc | gaa | ata | cca | tcc | tca | agg | cta | aga | act | aaa | tcg | att | att | 1488 |
| Leu | Val | Ser | Glu | Ile | Pro | Ser | Ser | Arg | Leu | Arg | Thr | Lys | Ser | Ile | Ile | |
| | | | | 485 | | | | | 490 | | | | | 495 | | |
| ctg | gct | cgt | aac | gca | tat | aat | atg | gca | tct | att | gta | act | act | gtt | ttg | 1536 |
| Leu | Ala | Arg | Asn | Ala | Tyr | Asn | Met | Ala | Ser | Ile | Val | Thr | Thr | Val | Leu | |
| | | | 500 | | | | | 505 | | | | | 510 | | | |
| atc | atg | tac | caa | ttg | aac | tca | gaa | aaa | tgg | aac | tgg | ggt | gcc | aag | tcg | 1584 |
| Ile | Met | Tyr | Gln | Leu | Asn | Ser | Glu | Lys | Trp | Asn | Trp | Gly | Ala | Lys | Ser | |
| | | | | 515 | | | | | 520 | | | | | 525 | | |
| ggc | ttt | ttc | tgg | gga | ggg | tta | tgt | ttt | gcc | act | cta | gtt | tgg | gcc | gta | 1632 |
| Gly | Phe | Phe | Trp | Gly | Gly | Leu | Cys | Phe | Ala | Thr | Leu | Val | Trp | Ala | Val | |
| | 530 | | | | | 535 | | | | | 540 | | | | | |
| att | gac | cta | cca | gaa | act | gct | ggc | agg | act | ttt | att | gag | ata | aat | gaa | 1680 |
| Ile | Asp | Leu | Pro | Glu | Thr | Ala | Gly | Arg | Thr | Phe | Ile | Glu | Ile | Asn | Glu | |
| 545 | | | | | 550 | | | | | 555 | | | | | 560 | |
| ttg | ttt | aga | ctt | ggt | gtt | cca | gca | aga | aag | ttc | aag | tcg | act | aaa | gtc | 1728 |
| Leu | Phe | Arg | Leu | Gly | Val | Pro | Ala | Arg | Lys | Phe | Lys | Ser | Thr | Lys | Val | |
| | | | | 565 | | | | | 570 | | | | | 575 | | |
| gac | cct | ttt | gca | gct | gcc | aaa | gca | gca | gct | gca | gaa | att | aat | gtt | aaa | 1776 |
| Asp | Pro | Phe | Ala | Ala | Ala | Lys | Ala | Ala | Ala | Ala | Glu | Ile | Asn | Val | Lys | |
| | | | 580 | | | | | 585 | | | | | 590 | | | |
| gat | ccg | aag | gaa | gat | ttg | gaa | act | tct | gtg | gta | gat | gaa | ggg | cga | agc | 1824 |
| Asp | Pro | Lys | Glu | Asp | Leu | Glu | Thr | Ser | Val | Val | Asp | Glu | Gly | Arg | Ser | |
| | | | | 595 | | | | | 600 | | | | | 605 | | |
| acc | cca | tct | gtt | gtg | aac | aaa | | | | | | | | | | 1845 |
| Thr | Pro | Ser | Val | Val | Asn | Lys | | | | | | | | | | |
| | 610 | | | | | 615 | | | | | | | | | | |

<210> SEQ ID NO 36
<211> LENGTH: 615
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 36

Met Lys Gly Leu Ser Ser Leu Ile Asn Arg Lys Lys Asp Arg Asn Asp
1               5                   10                  15

-continued

Ser His Leu Asp Glu Ile Glu Asn Gly Val Asn Ala Thr Glu Phe Asn
        20                  25                  30

Ser Ile Glu Met Glu Glu Gln Gly Lys Lys Ser Asp Phe Gly Leu Ser
        35                  40                  45

His His Glu Tyr Gly Pro Gly Ser Leu Thr Pro Asn Asp Asn Asn Glu
 50                  55                  60

Glu Val Pro Asp Leu Leu Asp Glu Ala Met Gln Asp Ala Lys Glu Ala
 65                  70                  75                  80

Asp Glu Ser Glu Arg Gly Met Pro Leu Met Thr Ala Leu Lys Thr Tyr
                 85                  90                  95

Pro Lys Ala Ala Ala Trp Ser Leu Leu Val Ser Thr Thr Leu Ile Gln
                100                 105                 110

Glu Gly Tyr Asp Thr Ala Ile Leu Gly Ser Phe Tyr Ala Leu Pro Val
                115                 120                 125

Phe Gln Lys Lys Tyr Gly Ser Leu Asn Ser Asn Thr Gly Asp Tyr Glu
        130                 135                 140

Ile Ser Ala Ser Trp Gln Ile Gly Leu Ser Leu Cys Val Thr Ala Gly
145                 150                 155                 160

Glu Ile Val Gly Leu Gln Met Thr Gly Pro Phe Val Asp Tyr Met Gly
                165                 170                 175

Asn Arg Tyr Thr Leu Ile Leu Ala Leu Ile Leu Ala Ala Phe Thr
                180                 185                 190

Phe Ile Leu Tyr Phe Cys Lys Gly Leu Gly Met Ile Ala Val Gly Gln
        195                 200                 205

Val Leu Cys Gly Met Pro Trp Gly Cys Phe Gln Cys Leu Thr Val Ser
        210                 215                 220

Tyr Ala Ser Glu Ile Cys Pro Met Ala Leu Arg Tyr Tyr Leu Thr Thr
225                 230                 235                 240

Tyr Ser Asn Leu Cys Trp Thr Phe Gly Gln Leu Phe Ala Ala Gly Ile
                245                 250                 255

Met Lys Asn Ser Gln Asn Lys Tyr Pro Asn Ser Glu Leu Gly Tyr Lys
                260                 265                 270

Leu Pro Phe Ala Leu Gln Trp Ile Trp Pro Ala Pro Leu Ala Ile Gly
        275                 280                 285

Ile Phe Phe Ala Pro Glu Ser Pro Trp Trp Leu Val Lys Lys Gly Arg
290                 295                 300

Ile Asp Gln Ala Arg Arg Ser Leu Glu Arg Thr Leu Ser Gly Lys Gly
305                 310                 315                 320

Pro Glu Lys Glu Leu Leu Val Ser Met Glu Leu Asp Asn Ile Lys Val
                325                 330                 335

Thr Ile Glu Lys Glu Lys Lys Leu Ser Asp Ser Glu Gly Ser Tyr Trp
                340                 345                 350

Asp Cys Leu Lys Asp Ser Val Asn Arg Arg Thr Arg Ile Ala Cys
        355                 360                 365

Leu Cys Trp Val Gly Gln Thr Thr Cys Gly Thr Ser Leu Ile Gly Asn
        370                 375                 380

Ser Thr Tyr Phe Tyr Glu Lys Ala Gly Val Gly Thr Asp Thr Ala Phe
385                 390                 395                 400

Thr Phe Ser Ile Ile Gln Tyr Cys Leu Gly Ile Ala Ala Thr Phe Leu
                405                 410                 415

Ser Trp Trp Ala Ser Lys Tyr Phe Gly Arg Phe Asp Leu Tyr Ala Phe
        420                 425                 430

Gly Leu Ala Ile Gln Thr Val Ser Leu Phe Ile Ile Gly Gly Leu Gly
        435                 440                 445

```
Cys Ser Asp Ser His Gly Ala Glu Met Gly Ser Gly Ser Leu Leu Met
    450                 455                 460

Val Leu Ser Phe Phe Tyr Asn Leu Gly Ile Ala Pro Val Val Phe Cys
465                 470                 475                 480

Leu Val Ser Glu Ile Pro Ser Ser Arg Leu Arg Thr Lys Ser Ile Ile
                485                 490                 495

Leu Ala Arg Asn Ala Tyr Asn Met Ala Ser Ile Val Thr Thr Val Leu
            500                 505                 510

Ile Met Tyr Gln Leu Asn Ser Glu Lys Trp Asn Trp Gly Ala Lys Ser
        515                 520                 525

Gly Phe Phe Trp Gly Gly Leu Cys Phe Ala Thr Leu Val Trp Ala Val
    530                 535                 540

Ile Asp Leu Pro Glu Thr Ala Gly Arg Thr Phe Ile Glu Ile Asn Glu
545                 550                 555                 560

Leu Phe Arg Leu Gly Val Pro Ala Arg Lys Phe Lys Ser Thr Lys Val
                565                 570                 575

Asp Pro Phe Ala Ala Ala Lys Ala Ala Ala Glu Ile Asn Val Lys
            580                 585                 590

Asp Pro Lys Glu Asp Leu Glu Thr Ser Val Val Asp Glu Gly Arg Ser
        595                 600                 605

Thr Pro Ser Val Val Asn Lys
    610                 615

<210> SEQ ID NO 37
<211> LENGTH: 1842
<212> TYPE: DNA
<213> ORGANISM: Artificial Sequence
<220> FEATURE:
<223> OTHER INFORMATION: Description of Artificial Sequence: Synthetic
      MAL31[E51V] polynucleotide
<220> FEATURE:
<221> NAME/KEY: CDS
<222> LOCATION: (1)..(1842)
<223> OTHER INFORMATION: Mal31p[Val51]

<400> SEQUENCE: 37 atg aag gga tta tcc tca tta ata aac aga aaa aaa gac agg aac gac     48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac     96
Ser His Leu Asp Glu Ile Glu Asn Gly Val Asn Ala Thr Glu Phe Asn
            20                  25                  30 tcg ata gag atg gag gag caa ggt aag aaa agt gat ttt gat ctt tcc    144
Ser Ile Glu Met Glu Glu Gln Gly Lys Lys Ser Asp Phe Asp Leu Ser
        35                  40                  45 cat ctt gtg tac ggt cca ggt tca cta ata cca aac gat aat aat gaa    192
His Leu Val Tyr Gly Pro Gly Ser Leu Ile Pro Asn Asp Asn Asn Glu
    50                  55                  60 gaa gtc ccc gac ctt ctc gat gaa gct atg cag gac gcc aaa gag gca    240
Glu Val Pro Asp Leu Leu Asp Glu Ala Met Gln Asp Ala Lys Glu Ala
65                  70                  75                  80 gat gaa agt gag agg gga atg cca ctc atg aca gct ttg aag aca tat    288
Asp Glu Ser Glu Arg Gly Met Pro Leu Met Thr Ala Leu Lys Thr Tyr
                85                  90                  95 cca aaa gct gct gct tgg tca cta tta gtt tcc aca aca ttg att caa    336
Pro Lys Ala Ala Ala Trp Ser Leu Leu Val Ser Thr Thr Leu Ile Gln
            100                 105                 110 gag ggt tat gac aca gcc att cta gga gct ttc tat gcc ctg cct gtt    384
Glu Gly Tyr Asp Thr Ala Ile Leu Gly Ala Phe Tyr Ala Leu Pro Val
        115                 120                 125
```

|     |     |     |     |     |     |     |     |     |     |     |     |     |     |     |     | |
|---|---|---|---|---|---|---|---|---|---|---|---|---|---|---|---|---|
| ttt | caa | aaa | aaa | tat | ggt | tct | ttg | aat | agc | aat | aca | gga | gat | tat | gaa | 432 |
| Phe | Gln | Lys | Lys | Tyr | Gly | Ser | Leu | Asn | Ser | Asn | Thr | Gly | Asp | Tyr | Glu | |
|     | 130 |     |     |     |     | 135 |     |     |     |     | 140 |     |     |     |     | |
| att | tca | gtt | tcc | tgg | caa | atc | ggt | cta | tgt | cta | tgc | tac | atg | gca | ggt | 480 |
| Ile | Ser | Val | Ser | Trp | Gln | Ile | Gly | Leu | Cys | Leu | Cys | Tyr | Met | Ala | Gly | |
| 145 |     |     |     |     | 150 |     |     |     |     | 155 |     |     |     |     | 160 | |
| gag | att | gtc | ggt | ttg | caa | atg | act | ggg | cct | tct | gta | gat | tac | atg | ggc | 528 |
| Glu | Ile | Val | Gly | Leu | Gln | Met | Thr | Gly | Pro | Ser | Val | Asp | Tyr | Met | Gly | |
|     |     |     |     | 165 |     |     |     |     | 170 |     |     |     |     | 175 |     | |
| aac | cgt | tac | act | ctg | atc | atg | gcg | ttg | ttc | ttt | tta | gcg | gct | ttc | att | 576 |
| Asn | Arg | Tyr | Thr | Leu | Ile | Met | Ala | Leu | Phe | Phe | Leu | Ala | Ala | Phe | Ile | |
|     |     |     | 180 |     |     |     |     | 185 |     |     |     |     | 190 |     |     | |
| ttc | att | ctg | tat | ttt | tgc | aag | agt | ttg | ggt | atg | att | gcc | gtg | gga | cag | 624 |
| Phe | Ile | Leu | Tyr | Phe | Cys | Lys | Ser | Leu | Gly | Met | Ile | Ala | Val | Gly | Gln | |
|     |     | 195 |     |     |     |     | 200 |     |     |     |     | 205 |     |     |     | |
| gca | ttg | tgt | ggt | atg | cca | tgg | ggt | tgt | ttc | caa | tgt | ttg | acc | gtt | tct | 672 |
| Ala | Leu | Cys | Gly | Met | Pro | Trp | Gly | Cys | Phe | Gln | Cys | Leu | Thr | Val | Ser | |
|     | 210 |     |     |     |     | 215 |     |     |     |     | 220 |     |     |     |     | |
| tat | gct | tct | gaa | att | tgt | cct | ttg | gcc | cta | aga | tac | tat | ttg | acg | act | 720 |
| Tyr | Ala | Ser | Glu | Ile | Cys | Pro | Leu | Ala | Leu | Arg | Tyr | Tyr | Leu | Thr | Thr | |
| 225 |     |     |     |     | 230 |     |     |     |     | 235 |     |     |     |     | 240 | |
| tat | tct | aat | tta | tgt | tgg | gcg | ttc | ggt | caa | ctt | ttc | gct | gct | ggt | att | 768 |
| Tyr | Ser | Asn | Leu | Cys | Trp | Ala | Phe | Gly | Gln | Leu | Phe | Ala | Ala | Gly | Ile | |
|     |     |     |     | 245 |     |     |     |     | 250 |     |     |     |     | 255 |     | |
| atg | aaa | aat | tcc | cag | aac | aaa | tat | gcc | aac | tca | gaa | cta | gga | tat | aag | 816 |
| Met | Lys | Asn | Ser | Gln | Asn | Lys | Tyr | Ala | Asn | Ser | Glu | Leu | Gly | Tyr | Lys | |
|     |     |     | 260 |     |     |     |     | 265 |     |     |     |     | 270 |     |     | |
| cta | cct | ttt | gct | ttg | cag | tgg | atc | tgg | ccc | ctt | cct | ttg | gcg | gta | ggt | 864 |
| Leu | Pro | Phe | Ala | Leu | Gln | Trp | Ile | Trp | Pro | Leu | Pro | Leu | Ala | Val | Gly | |
|     |     | 275 |     |     |     |     | 280 |     |     |     |     | 285 |     |     |     | |
| att | ttt | ttt | gca | cca | gag | tct | cca | tgg | tgg | ctg | gtt | aaa | aaa | gga | agg | 912 |
| Ile | Phe | Phe | Ala | Pro | Glu | Ser | Pro | Trp | Trp | Leu | Val | Lys | Lys | Gly | Arg | |
|     | 290 |     |     |     |     | 295 |     |     |     |     | 300 |     |     |     |     | |
| att | gat | caa | gcg | agg | aga | tca | ctt | gaa | aga | aca | tta | agt | ggt | aaa | gga | 960 |
| Ile | Asp | Gln | Ala | Arg | Arg | Ser | Leu | Glu | Arg | Thr | Leu | Ser | Gly | Lys | Gly | |
| 305 |     |     |     |     | 310 |     |     |     |     | 315 |     |     |     |     | 320 | |
| ccc | gag | aaa | gaa | tta | cta | gtg | agt | atg | gaa | ctc | gat | aaa | atc | aaa | act | 1008 |
| Pro | Glu | Lys | Glu | Leu | Leu | Val | Ser | Met | Glu | Leu | Asp | Lys | Ile | Lys | Thr | |
|     |     |     |     | 325 |     |     |     |     | 330 |     |     |     |     | 335 |     | |
| act | ata | gaa | aag | gag | cag | aaa | atg | tct | gat | gaa | gga | act | tac | tgg | gat | 1056 |
| Thr | Ile | Glu | Lys | Glu | Gln | Lys | Met | Ser | Asp | Glu | Gly | Thr | Tyr | Trp | Asp | |
|     |     |     | 340 |     |     |     |     | 345 |     |     |     |     | 350 |     |     | |
| tgt | gtg | aaa | gat | ggt | att | aac | agg | aga | aga | acg | aga | ata | gct | tgt | tta | 1104 |
| Cys | Val | Lys | Asp | Gly | Ile | Asn | Arg | Arg | Arg | Thr | Arg | Ile | Ala | Cys | Leu | |
|     |     | 355 |     |     |     |     | 360 |     |     |     |     | 365 |     |     |     | |
| tgt | tgg | atc | ggt | caa | tgc | tcc | tgt | ggt | gca | tca | tta | att | ggt | tat | tca | 1152 |
| Cys | Trp | Ile | Gly | Gln | Cys | Ser | Cys | Gly | Ala | Ser | Leu | Ile | Gly | Tyr | Ser | |
|     | 370 |     |     |     |     | 375 |     |     |     |     | 380 |     |     |     |     | |
| act | tac | ttt | tat | gaa | aaa | gct | ggt | gtt | agc | act | gat | acg | gct | ttt | act | 1200 |
| Thr | Tyr | Phe | Tyr | Glu | Lys | Ala | Gly | Val | Ser | Thr | Asp | Thr | Ala | Phe | Thr | |
| 385 |     |     |     |     | 390 |     |     |     |     | 395 |     |     |     |     | 400 | |
| ttc | agt | att | atc | caa | tat | tgt | ctt | ggt | att | gct | gca | acg | ttt | ata | tcc | 1248 |
| Phe | Ser | Ile | Ile | Gln | Tyr | Cys | Leu | Gly | Ile | Ala | Ala | Thr | Phe | Ile | Ser | |
|     |     |     |     | 405 |     |     |     |     | 410 |     |     |     |     | 415 |     | |
| tgg | tgg | gct | tca | aaa | tat | tgt | ggc | aga | ttt | gac | ctt | tat | gct | ttt | ggg | 1296 |
| Trp | Trp | Ala | Ser | Lys | Tyr | Cys | Gly | Arg | Phe | Asp | Leu | Tyr | Ala | Phe | Gly | |
|     |     |     | 420 |     |     |     |     | 425 |     |     |     |     | 430 |     |     | |
| ctg | gct | ttt | cag | gct | att | atg | ttc | ttc | att | atc | ggt | ggt | tta | gga | tgt | 1344 |
| Leu | Ala | Phe | Gln | Ala | Ile | Met | Phe | Phe | Ile | Ile | Gly | Gly | Leu | Gly | Cys | |
|     |     | 435 |     |     |     |     | 440 |     |     |     |     | 445 |     |     |     | |

```
tca gac act cat ggc gct aaa atg ggt agt ggt gct ctt cta atg gtt    1392
Ser Asp Thr His Gly Ala Lys Met Gly Ser Gly Ala Leu Leu Met Val
    450                 455                 460 gtc gcg ttc ttt tac aac ctc ggt att gca cct gtt gtt ttt tgc tta    1440
Val Ala Phe Phe Tyr Asn Leu Gly Ile Ala Pro Val Val Phe Cys Leu
465                 470                 475                 480 gtg tct gaa ata ccg tct tca agg cta aga acc aaa aca att att ttg    1488
Val Ser Glu Ile Pro Ser Ser Arg Leu Arg Thr Lys Thr Ile Ile Leu
                485                 490                 495 gct cgt aat gct tac aat gtg atc caa gtt gta gtt aca gtt ttg atc    1536
Ala Arg Asn Ala Tyr Asn Val Ile Gln Val Val Val Thr Val Leu Ile
            500                 505                 510 atg tac caa ttg aac tca gag aaa tgg aat tgg ggt gct aaa tca ggc    1584
Met Tyr Gln Leu Asn Ser Glu Lys Trp Asn Trp Gly Ala Lys Ser Gly
        515                 520                 525 ttt ttc tgg gga gga ttt tgt ctg gcc act tta gct tgg gct gtt gtc    1632
Phe Phe Trp Gly Gly Phe Cys Leu Ala Thr Leu Ala Trp Ala Val Val
    530                 535                 540 gat tta cca gaa acc gct ggc agg act ttt att gag ata aat gaa ttg    1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac    1728
Phe Arg Leu Gly Val Pro Ala Arg Lys Phe Lys Ser Thr Lys Val Asp
                565                 570                 575 cct ttt gca gct gcc aaa gca gca gct gca gaa att aat gtt aaa gat    1776
Pro Phe Ala Ala Ala Lys Ala Ala Ala Glu Ile Asn Val Lys Asp
            580                 585                 590 ccg aag gaa gat ttg gaa act tct gtg gta gat gaa ggg cga aac acc    1824
Pro Lys Glu Asp Leu Glu Thr Ser Val Val Asp Glu Gly Arg Asn Thr
        595                 600                 605 tca tct gtt gtg aac aaa                                            1842
Ser Ser Val Val Asn Lys
    610

<210> SEQ ID NO 38
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Asp Leu Ser
        35                  40                  45

His Leu Val Tyr Gly Pro Gly Ser Leu Ile Pro Asn Asp Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ala Phe Tyr Ala Leu Pro Val
        115                 120                 125
```

```
Phe Gln Lys Lys Tyr Gly Ser Leu Asn Ser Asn Thr Gly Asp Tyr Glu
    130                 135                 140

Ile Ser Val Ser Trp Gln Ile Gly Leu Cys Leu Cys Tyr Met Ala Gly
145                 150                 155                 160

Glu Ile Val Gly Leu Gln Met Thr Gly Pro Ser Val Asp Tyr Met Gly
                165                 170                 175

Asn Arg Tyr Thr Leu Ile Met Ala Leu Phe Phe Leu Ala Ala Phe Ile
            180                 185                 190

Phe Ile Leu Tyr Phe Cys Lys Ser Leu Gly Met Ile Ala Val Gly Gln
        195                 200                 205

Ala Leu Cys Gly Met Pro Trp Gly Cys Phe Gln Cys Leu Thr Val Ser
210                 215                 220

Tyr Ala Ser Glu Ile Cys Pro Leu Ala Leu Arg Tyr Tyr Leu Thr Thr
225                 230                 235                 240

Tyr Ser Asn Leu Cys Trp Ala Phe Gly Gln Leu Phe Ala Ala Gly Ile
                245                 250                 255

Met Lys Asn Ser Gln Asn Lys Tyr Ala Asn Ser Glu Leu Gly Tyr Lys
            260                 265                 270

Leu Pro Phe Ala Leu Gln Trp Ile Trp Pro Leu Pro Leu Ala Val Gly
        275                 280                 285

Ile Phe Phe Ala Pro Glu Ser Pro Trp Trp Leu Val Lys Lys Gly Arg
290                 295                 300

Ile Asp Gln Ala Arg Arg Ser Leu Glu Arg Thr Leu Ser Gly Lys Gly
305                 310                 315                 320

Pro Glu Lys Glu Leu Leu Val Ser Met Glu Leu Asp Lys Ile Lys Thr
                325                 330                 335

Thr Ile Glu Lys Glu Gln Lys Met Ser Asp Glu Gly Thr Tyr Trp Asp
            340                 345                 350

Cys Val Lys Asp Gly Ile Asn Arg Arg Thr Arg Ile Ala Cys Leu
        355                 360                 365

Cys Trp Ile Gly Gln Cys Ser Cys Gly Ala Ser Leu Ile Gly Tyr Ser
370                 375                 380

Thr Tyr Phe Tyr Glu Lys Ala Gly Val Ser Thr Asp Thr Ala Phe Thr
385                 390                 395                 400

Phe Ser Ile Ile Gln Tyr Cys Leu Gly Ile Ala Ala Thr Phe Ile Ser
                405                 410                 415

Trp Trp Ala Ser Lys Tyr Cys Gly Arg Phe Asp Leu Tyr Ala Phe Gly
            420                 425                 430

Leu Ala Phe Gln Ala Ile Met Phe Phe Ile Ile Gly Gly Leu Gly Cys
        435                 440                 445

Ser Asp Thr His Gly Ala Lys Met Gly Ser Gly Ala Leu Leu Met Val
450                 455                 460

Val Ala Phe Phe Tyr Asn Leu Gly Ile Ala Pro Val Val Phe Cys Leu
465                 470                 475                 480

Val Ser Glu Ile Pro Ser Ser Arg Leu Arg Thr Lys Thr Ile Ile Leu
                485                 490                 495

Ala Arg Asn Ala Tyr Asn Val Ile Gln Val Val Thr Val Leu Ile
            500                 505                 510

Met Tyr Gln Leu Asn Ser Glu Lys Trp Asn Trp Gly Ala Lys Ser Gly
        515                 520                 525

Phe Phe Trp Gly Gly Phe Cys Leu Ala Thr Leu Ala Trp Ala Val Val
530                 535                 540

Asp Leu Pro Glu Thr Ala Gly Arg Thr Phe Ile Glu Ile Asn Glu Leu
545                 550                 555                 560
```

-continued

Phe Arg Leu Gly Val Pro Ala Arg Lys Phe Lys Ser Thr Lys Val Asp
            565                 570                 575

Pro Phe Ala Ala Ala Lys Ala Ala Ala Glu Ile Asn Val Lys Asp
        580                 585                 590

Pro Lys Glu Asp Leu Glu Thr Ser Val Val Asp Glu Gly Arg Asn Thr
        595                 600                 605

Ser Ser Val Val Asn Lys
    610

<210> SEQ ID NO 39
<211> LENGTH: 1842
<212> TYPE: DNA
<213> ORGANISM: Artificial Sequence
<220> FEATURE:
<223> OTHER INFORMATION: Description of Artificial Sequence: Synthetic
      MAL31[S48P] polynucleotide
<220> FEATURE:
<221> NAME/KEY: CDS
<222> LOCATION: (1)..(1842)
<223> OTHER INFORMATION: Mal31p[Pro48]

<400> SEQUENCE: 39

| atg aag gga tta tcc tca tta ata aac aga aaa aaa gac agg aac gac | 48 |
| Met Lys Gly Leu Ser Ser Leu Ile Asn Arg Lys Lys Asp Arg Asn Asp | |
| 1               5                   10                  15 | |

| tca cac tta gat gag atc gag aat ggc gtg aac gct acc gaa ttc aac | 96 |
| Ser His Leu Asp Glu Ile Glu Asn Gly Val Asn Ala Thr Glu Phe Asn | |
|             20                  25                  30 | |

| tcg ata gag atg gag gag caa ggt aag aaa agt gat ttt gat ctt ccc | 144 |
| Ser Ile Glu Met Glu Glu Gln Gly Lys Lys Ser Asp Phe Asp Leu Pro | |
|         35                  40                  45 | |

| cat ctt gag tac ggt cca ggt tca cta ata cca aac gat aat aat gaa | 192 |
| His Leu Glu Tyr Gly Pro Gly Ser Leu Ile Pro Asn Asp Asn Asn Glu | |
|     50                  55                  60 | |

| gaa gtc ccc gac ctt ctc gat gaa gct atg cag gac gcc aaa gag gca | 240 |
| Glu Val Pro Asp Leu Leu Asp Glu Ala Met Gln Asp Ala Lys Glu Ala | |
| 65                  70                  75                  80 | |

| gat gaa agt gag agg gga atg cca ctc atg aca gct ttg aag aca tat | 288 |
| Asp Glu Ser Glu Arg Gly Met Pro Leu Met Thr Ala Leu Lys Thr Tyr | |
|                 85                  90                  95 | |

| cca aaa gct gct gct tgg tca cta tta gtt tcc aca aca ttg att caa | 336 |
| Pro Lys Ala Ala Ala Trp Ser Leu Leu Val Ser Thr Thr Leu Ile Gln | |
|             100                 105                 110 | |

| gag ggt tat gac aca gcc att cta gga gct ttc tat gcc ctg cct gtt | 384 |
| Glu Gly Tyr Asp Thr Ala Ile Leu Gly Ala Phe Tyr Ala Leu Pro Val | |
|         115                 120                 125 | |

| ttt caa aaa aaa tat ggt tct ttg aat agc aat aca gga gat tat gaa | 432 |
| Phe Gln Lys Lys Tyr Gly Ser Leu Asn Ser Asn Thr Gly Asp Tyr Glu | |
|     130                 135                 140 | |

| att tca gtt tcc tgg caa atc ggt cta tgt cta tgc tac atg gca ggt | 480 |
| Ile Ser Val Ser Trp Gln Ile Gly Leu Cys Leu Cys Tyr Met Ala Gly | |
| 145                 150                 155                 160 | |

| gag att gtc ggt ttg caa atg act ggg cct tct gta gat tac atg ggc | 528 |
| Glu Ile Val Gly Leu Gln Met Thr Gly Pro Ser Val Asp Tyr Met Gly | |
|                 165                 170                 175 | |

| aac cgt tac act ctg atc atg gcg ttg ttc ttt tta gcg gct ttc att | 576 |
| Asn Arg Tyr Thr Leu Ile Met Ala Leu Phe Phe Leu Ala Ala Phe Ile | |
|             180                 185                 190 | |

| ttc att ctg tat ttt tgc aag agt ttg ggt atg att gcc gtg gga cag | 624 |
| Phe Ile Leu Tyr Phe Cys Lys Ser Leu Gly Met Ile Ala Val Gly Gln | |
|         195                 200                 205 | |

```
gca ttg tgt ggt atg cca tgg ggt tgt ttc caa tgt ttg acc gtt tct      672
Ala Leu Cys Gly Met Pro Trp Gly Cys Phe Gln Cys Leu Thr Val Ser
    210             215                 220 tat gct tct gaa att tgt cct ttg gcc cta aga tac tat ttg acg act      720
Tyr Ala Ser Glu Ile Cys Pro Leu Ala Leu Arg Tyr Tyr Leu Thr Thr
225             230                 235                 240 tat tct aat tta tgt tgg gcg ttc ggt caa ctt ttc gct gct ggt att      768
Tyr Ser Asn Leu Cys Trp Ala Phe Gly Gln Leu Phe Ala Ala Gly Ile
                245                 250                 255 atg aaa aat tcc cag aac aaa tat gcc aac tca gaa cta gga tat aag      816
Met Lys Asn Ser Gln Asn Lys Tyr Ala Asn Ser Glu Leu Gly Tyr Lys
            260                 265                 270 cta cct ttt gct ttg cag tgg atc tgg ccc ctt cct ttg gcg gta ggt      864
Leu Pro Phe Ala Leu Gln Trp Ile Trp Pro Leu Pro Leu Ala Val Gly
        275                 280                 285 att ttt ttt gca cca gag tct cca tgg tgg ctg gtt aaa aaa gga agg      912
Ile Phe Phe Ala Pro Glu Ser Pro Trp Trp Leu Val Lys Lys Gly Arg
    290                 295                 300 att gat caa gcg agg aga tca ctt gaa aga aca tta agt ggt aaa gga      960
Ile Asp Gln Ala Arg Arg Ser Leu Glu Arg Thr Leu Ser Gly Lys Gly
305             310                 315                 320 ccc gag aaa gaa tta cta gtg agt atg gaa ctc gat aaa atc aaa act     1008
Pro Glu Lys Glu Leu Leu Val Ser Met Glu Leu Asp Lys Ile Lys Thr
                325                 330                 335 act ata gaa aag gag cag aaa atg tct gat gaa gga act tac tgg gat     1056
Thr Ile Glu Lys Glu Gln Lys Met Ser Asp Glu Gly Thr Tyr Trp Asp
            340                 345                 350 tgt gtg aaa gat ggt att aac agg aga aga acg aga ata gct tgt tta     1104
Cys Val Lys Asp Gly Ile Asn Arg Arg Arg Thr Arg Ile Ala Cys Leu
        355                 360                 365 tgt tgg atc ggt caa tgc tcc tgt ggt gca tca tta att ggt tat tca     1152
Cys Trp Ile Gly Gln Cys Ser Cys Gly Ala Ser Leu Ile Gly Tyr Ser
    370                 375                 380 act tac ttt tat gaa aaa gct ggt gtt agc act gat acg gct ttt act     1200
Thr Tyr Phe Tyr Glu Lys Ala Gly Val Ser Thr Asp Thr Ala Phe Thr
385             390                 395                 400 ttc agt att atc caa tat tgt ctt ggt att gct gca acg ttt ata tcc     1248
Phe Ser Ile Ile Gln Tyr Cys Leu Gly Ile Ala Ala Thr Phe Ile Ser
                405                 410                 415 tgg tgg gct tca aaa tat tgt ggc aga ttt gac ctt tat gct ttt ggg     1296
Trp Trp Ala Ser Lys Tyr Cys Gly Arg Phe Asp Leu Tyr Ala Phe Gly
            420                 425                 430 ctg gct ttt cag gct att atg ttc ttc att atc ggt ggt tta gga tgt     1344
Leu Ala Phe Gln Ala Ile Met Phe Phe Ile Ile Gly Gly Leu Gly Cys
        435                 440                 445 tca gac act cat ggc gct aaa atg ggt agt ggt gct ctt cta atg gtt     1392
Ser Asp Thr His Gly Ala Lys Met Gly Ser Gly Ala Leu Leu Met Val
    450                 455                 460 gtc gcg ttc ttt tac aac ctc ggt att gca cct gtt gtt ttt tgc tta     1440
Val Ala Phe Phe Tyr Asn Leu Gly Ile Ala Pro Val Val Phe Cys Leu
465             470                 475                 480 gtg tct gaa ata ccg tct tca agg cta aga acc aaa aca att att ttg     1488
Val Ser Glu Ile Pro Ser Ser Arg Leu Arg Thr Lys Thr Ile Ile Leu
                485                 490                 495 gct cgt aat gct tac aat gtg atc caa gtt gta gtt aca gtt ttg atc     1536
Ala Arg Asn Ala Tyr Asn Val Ile Gln Val Val Val Thr Val Leu Ile
            500                 505                 510 atg tac caa ttg aac tca gag aaa tgg aat tgg ggt gct aaa tca ggc     1584
Met Tyr Gln Leu Asn Ser Glu Lys Trp Asn Trp Gly Ala Lys Ser Gly
        515                 520                 525
```

```
ttt ttc tgg gga gga ttt tgt ctg gcc act tta gct tgg gct gtt gtc    1632
Phe Phe Trp Gly Gly Phe Cys Leu Ala Thr Leu Ala Trp Ala Val Val
    530                 535                 540 gat tta cca gaa acc gct ggc agg act ttt att gag ata aat gaa ttg    1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac    1728
Phe Arg Leu Gly Val Pro Ala Arg Lys Phe Lys Ser Thr Lys Val Asp
                565                 570                 575 cct ttt gca gct gcc aaa gca gca gct gca gaa att aat gtt aaa gat    1776
Pro Phe Ala Ala Ala Lys Ala Ala Ala Ala Glu Ile Asn Val Lys Asp
            580                 585                 590 ccg aag gaa gat ttg gaa act tct gtg gta gat gaa ggg cga aac acc    1824
Pro Lys Glu Asp Leu Glu Thr Ser Val Val Asp Glu Gly Arg Asn Thr
        595                 600                 605 tca tct gtt gtg aac aaa                                            1842
Ser Ser Val Val Asn Lys
    610

<210> SEQ ID NO 40
<211> LENGTH: 614
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 40

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Asp Leu Pro
        35                  40                  45

His Leu Glu Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ala Phe Tyr Ala Leu Pro Val
        115                 120                 125

Phe Gln Lys Lys Tyr Gly Ser Leu Asn Ser Asn Thr Gly Asp Tyr Glu
    130                 135                 140

Ile Ser Val Ser Trp Gln Ile Gly Leu Cys Leu Cys Tyr Met Ala Gly
145                 150                 155                 160

Glu Ile Val Gly Leu Gln Met Thr Gly Pro Ser Val Asp Tyr Met Gly
                165                 170                 175

Asn Arg Tyr Thr Leu Ile Met Ala Leu Phe Phe Leu Ala Ala Phe Ile
            180                 185                 190

Phe Ile Leu Tyr Phe Cys Lys Ser Leu Gly Met Ile Ala Val Gly Gln
        195                 200                 205

Ala Leu Cys Gly Met Pro Trp Gly Cys Phe Gln Cys Leu Thr Val Ser
    210                 215                 220

Tyr Ala Ser Glu Ile Cys Pro Leu Ala Leu Arg Tyr Tyr Leu Thr Thr
225                 230                 235                 240
```

```
Tyr Ser Asn Leu Cys Trp Ala Phe Gly Gln Leu Phe Ala Ala Gly Ile
            245                 250                 255

Met Lys Asn Ser Gln Asn Lys Tyr Ala Asn Ser Glu Leu Gly Tyr Lys
        260                 265                 270

Leu Pro Phe Ala Leu Gln Trp Ile Trp Pro Leu Pro Leu Ala Val Gly
        275                 280                 285

Ile Phe Phe Ala Pro Glu Ser Pro Trp Trp Leu Val Lys Lys Gly Arg
        290                 295                 300

Ile Asp Gln Ala Arg Arg Ser Leu Glu Arg Thr Leu Ser Gly Lys Gly
305                 310                 315                 320

Pro Glu Lys Glu Leu Leu Val Ser Met Glu Leu Asp Lys Ile Lys Thr
                325                 330                 335

Thr Ile Glu Lys Glu Gln Lys Met Ser Asp Glu Gly Thr Tyr Trp Asp
                340                 345                 350

Cys Val Lys Asp Gly Ile Asn Arg Arg Thr Arg Ile Ala Cys Leu
                355                 360                 365

Cys Trp Ile Gly Gln Cys Ser Cys Gly Ala Ser Leu Ile Gly Tyr Ser
        370                 375                 380

Thr Tyr Phe Tyr Glu Lys Ala Gly Val Ser Thr Asp Thr Ala Phe Thr
385                 390                 395                 400

Phe Ser Ile Ile Gln Tyr Cys Leu Gly Ile Ala Ala Thr Phe Ile Ser
                405                 410                 415

Trp Trp Ala Ser Lys Tyr Cys Gly Arg Phe Asp Leu Tyr Ala Phe Gly
                420                 425                 430

Leu Ala Phe Gln Ala Ile Met Phe Phe Ile Ile Gly Gly Leu Gly Cys
            435                 440                 445

Ser Asp Thr His Gly Ala Lys Met Gly Ser Gly Ala Leu Leu Met Val
    450                 455                 460

Val Ala Phe Phe Tyr Asn Leu Gly Ile Ala Pro Val Val Phe Cys Leu
465                 470                 475                 480

Val Ser Glu Ile Pro Ser Ser Arg Leu Arg Thr Lys Thr Ile Ile Leu
                485                 490                 495

Ala Arg Asn Ala Tyr Asn Val Ile Gln Val Val Thr Val Leu Ile
            500                 505                 510

Met Tyr Gln Leu Asn Ser Glu Lys Trp Asn Trp Gly Ala Lys Ser Gly
        515                 520                 525

Phe Phe Trp Gly Gly Phe Cys Leu Ala Thr Leu Ala Trp Ala Val Val
    530                 535                 540

Asp Leu Pro Glu Thr Ala Gly Arg Thr Phe Ile Glu Ile Asn Glu Leu
545                 550                 555                 560

Phe Arg Leu Gly Val Pro Ala Arg Lys Phe Lys Ser Thr Lys Val Asp
                565                 570                 575

Pro Phe Ala Ala Ala Lys Ala Ala Ala Glu Ile Asn Val Lys Asp
            580                 585                 590

Pro Lys Glu Asp Leu Glu Thr Ser Val Val Asp Glu Gly Arg Asn Thr
        595                 600                 605

Ser Ser Val Val Asn Lys
    610
```

<210> SEQ ID NO 41
<211> LENGTH: 1842
<212> TYPE: DNA
<213> ORGANISM: Artificial Sequence
<220> FEATURE:
<223> OTHER INFORMATION: Description of Artificial Sequence: Synthetic MAL31[H49P] polynucleotide

```
-continued

<220> FEATURE:
<221> NAME/KEY: CDS
<222> LOCATION: (1)..(1842)
<223> OTHER INFORMATION: Mal31p[Pro49]

<400> SEQUENCE: 41 atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
            20                  25                  30 tcg ata gag atg gag gag caa ggt aag aaa agt gat ttt gat ctt tcc     144
Ser Ile Glu Met Glu Glu Gln Gly Lys Lys Ser Asp Phe Asp Leu Ser
        35                  40                  45 cct ctt gag tac ggt cca ggt tca cta ata cca aac gat aat aat gaa     192
Pro Leu Glu Tyr Gly Pro Gly Ser Leu Ile Pro Asn Asp Asn Asn Glu
    50                  55                  60 gaa gtc ccc gac ctt ctc gat gaa gct atg cag gac gcc aaa gag gca     240
Glu Val Pro Asp Leu Leu Asp Glu Ala Met Gln Asp Ala Lys Glu Ala
65                  70                  75                  80 gat gaa agt gag agg gga atg cca ctc atg aca gct ttg aag aca tat     288
Asp Glu Ser Glu Arg Gly Met Pro Leu Met Thr Ala Leu Lys Thr Tyr
                85                  90                  95 cca aaa gct gct gct tgg tca cta tta gtt tcc aca aca ttg att caa     336
Pro Lys Ala Ala Ala Trp Ser Leu Leu Val Ser Thr Thr Leu Ile Gln
            100                 105                 110 gag ggt tat gac aca gcc att cta gga gct ttc tat gcc ctg cct gtt     384
Glu Gly Tyr Asp Thr Ala Ile Leu Gly Ala Phe Tyr Ala Leu Pro Val
        115                 120                 125 ttt caa aaa aaa tat ggt tct ttg aat agc aat aca gga gat tat gaa     432
Phe Gln Lys Lys Tyr Gly Ser Leu Asn Ser Asn Thr Gly Asp Tyr Glu
    130                 135                 140 att tca gtt tcc tgg caa atc ggt cta tgt cta tgc tac atg gca ggt     480
Ile Ser Val Ser Trp Gln Ile Gly Leu Cys Leu Cys Tyr Met Ala Gly
145                 150                 155                 160 gag att gtc ggt ttg caa atg act ggg cct tct gta gat tac atg ggc     528
Glu Ile Val Gly Leu Gln Met Thr Gly Pro Ser Val Asp Tyr Met Gly
                165                 170                 175 aac cgt tac act ctg atc atg gcg ttg ttt tta gcg gct ttc att         576
Asn Arg Tyr Thr Leu Ile Met Ala Leu Phe Phe Leu Ala Ala Phe Ile
            180                 185                 190 ttc att ctg tat ttt tgc aag agt ttg ggt atg att gcc gtg gga cag     624
Phe Ile Leu Tyr Phe Cys Lys Ser Leu Gly Met Ile Ala Val Gly Gln
        195                 200                 205 gca ttg tgt ggt atg cca tgg ggt tgt ttc caa tgt ttg acc gtt tct     672
Ala Leu Cys Gly Met Pro Trp Gly Cys Phe Gln Cys Leu Thr Val Ser
    210                 215                 220 tat gct tct gaa att tgt cct ttg gcc cta aga tac tat ttg acg act     720
Tyr Ala Ser Glu Ile Cys Pro Leu Ala Leu Arg Tyr Tyr Leu Thr Thr
225                 230                 235                 240 tat tct aat tta tgt tgg gcg ttc ggt caa ctt ttc gct gct ggt att     768
Tyr Ser Asn Leu Cys Trp Ala Phe Gly Gln Leu Phe Ala Ala Gly Ile
                245                 250                 255 atg aaa aat tcc cag aac aaa tat gcc aac tca gaa cta gga tat aag     816
Met Lys Asn Ser Gln Asn Lys Tyr Ala Asn Ser Glu Leu Gly Tyr Lys
            260                 265                 270 cta cct ttt gct ttg cag tgg atc tgg ccc ctt cct ttg gcg gta ggt     864
Leu Pro Phe Ala Leu Gln Trp Ile Trp Pro Leu Pro Leu Ala Val Gly
        275                 280                 285 att ttt ttt gca cca gag tct cca tgg tgg ctg gtt aaa aaa gga agg     912
```

```
Ile Phe Phe Ala Pro Glu Ser Pro Trp Trp Leu Val Lys Lys Gly Arg
        290             295                 300 att gat caa gcg agg aga tca ctt gaa aga aca tta agt ggt aaa gga    960
Ile Asp Gln Ala Arg Arg Ser Leu Glu Arg Thr Leu Ser Gly Lys Gly
305             310                 315                 320 ccc gag aaa gaa tta cta gtg agt atg gaa ctc gat aaa atc aaa act   1008
Pro Glu Lys Glu Leu Leu Val Ser Met Glu Leu Asp Lys Ile Lys Thr
                325                 330                 335 act ata gaa aag gag cag aaa atg tct gat gaa gga act tac tgg gat   1056
Thr Ile Glu Lys Glu Gln Lys Met Ser Asp Glu Gly Thr Tyr Trp Asp
            340                 345                 350 tgt gtg aaa gat ggt att aac agg aga aga acg aga ata gct tgt tta   1104
Cys Val Lys Asp Gly Ile Asn Arg Arg Arg Thr Arg Ile Ala Cys Leu
        355                 360                 365 tgt tgg atc ggt caa tgc tcc tgt ggt gca tca tta att ggt tat tca   1152
Cys Trp Ile Gly Gln Cys Ser Cys Gly Ala Ser Leu Ile Gly Tyr Ser
    370                 375                 380 act tac ttt tat gaa aaa gct ggt gtt agc act gat acg gct ttt act   1200
Thr Tyr Phe Tyr Glu Lys Ala Gly Val Ser Thr Asp Thr Ala Phe Thr
385                 390                 395                 400 ttc agt att atc caa tat tgt ctt ggt att gct gca acg ttt ata tcc   1248
Phe Ser Ile Ile Gln Tyr Cys Leu Gly Ile Ala Ala Thr Phe Ile Ser
            405                 410                 415 tgg tgg gct tca aaa tat tgt ggc aga ttt gac ctt tat gct ttt ggg   1296
Trp Trp Ala Ser Lys Tyr Cys Gly Arg Phe Asp Leu Tyr Ala Phe Gly
        420                 425                 430 ctg gct ttt cag gct att atg ttc ttc att atc ggt ggt tta gga tgt   1344
Leu Ala Phe Gln Ala Ile Met Phe Phe Ile Ile Gly Gly Leu Gly Cys
    435                 440                 445 tca gac act cat ggc gct aaa atg ggt agt ggt gct ctt cta atg gtt   1392
Ser Asp Thr His Gly Ala Lys Met Gly Ser Gly Ala Leu Leu Met Val
450                 455                 460 gtc gcg ttc ttt tac aac ctc ggt att gca cct gtt gtt ttt tgc tta   1440
Val Ala Phe Phe Tyr Asn Leu Gly Ile Ala Pro Val Val Phe Cys Leu
465                 470                 475                 480 gtg tct gaa ata ccg tct tca agg cta aga acc aaa aca att att ttg   1488
Val Ser Glu Ile Pro Ser Ser Arg Leu Arg Thr Lys Thr Ile Ile Leu
            485                 490                 495 gct cgt aat gct tac aat gtg atc caa gtt gta gtt aca gtt ttg atc   1536
Ala Arg Asn Ala Tyr Asn Val Ile Gln Val Val Val Thr Val Leu Ile
        500                 505                 510 atg tac caa ttg aac tca gag aaa tgg aat tgg ggt gct aaa tca ggc   1584
Met Tyr Gln Leu Asn Ser Glu Lys Trp Asn Trp Gly Ala Lys Ser Gly
    515                 520                 525 ttt ttc tgg gga gga ttt tgt ctg gcc act tta gct tgg gct gtt gtc   1632
Phe Phe Trp Gly Gly Phe Cys Leu Ala Thr Leu Ala Trp Ala Val Val
530                 535                 540 gat tta cca gaa acc gct ggc agg act ttt att gag ata aat gaa ttg   1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac   1728
Phe Arg Leu Gly Val Pro Ala Arg Lys Phe Lys Ser Thr Lys Val Asp
            565                 570                 575 cct ttt gca gct gcc aaa gca gca gct gca gaa att aat gtt aaa gat   1776
Pro Phe Ala Ala Ala Lys Ala Ala Ala Glu Ile Asn Val Lys Asp
        580                 585                 590 ccg aag gaa gat ttg gaa act tct gtg gta gat gaa ggg cga aac acc   1824
Pro Lys Glu Asp Leu Glu Thr Ser Val Val Asp Glu Gly Arg Asn Thr
    595                 600                 605 tca tct gtt gtg aac aaa                                           1842
```

Ser Ser Val Val Asn Lys
        610

<210> SEQ ID NO 42
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Asp Leu Ser
        35                  40                  45

Pro Leu Glu Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ala Phe Tyr Ala Leu Pro Val
        115                 120                 125

Phe Gln Lys Lys Tyr Gly Ser Leu Asn Ser Asn Thr Gly Asp Tyr Glu
    130                 135                 140

Ile Ser Val Ser Trp Gln Ile Gly Leu Cys Leu Cys Tyr Met Ala Gly
145                 150                 155                 160

Glu Ile Val Gly Leu Gln Met Thr Gly Pro Ser Val Asp Tyr Met Gly
                165                 170                 175

Asn Arg Tyr Thr Leu Ile Met Ala Leu Phe Phe Leu Ala Ala Phe Ile
            180                 185                 190

Phe Ile Leu Tyr Phe Cys Lys Ser Leu Gly Met Ile Ala Val Gly Gln
        195                 200                 205

Ala Leu Cys Gly Met Pro Trp Gly Cys Phe Gln Cys Leu Thr Val Ser
    210                 215                 220

Tyr Ala Ser Glu Ile Cys Pro Leu Ala Leu Arg Tyr Tyr Leu Thr Thr
225                 230                 235                 240

Tyr Ser Asn Leu Cys Trp Ala Phe Gly Gln Leu Phe Ala Ala Gly Ile
                245                 250                 255

Met Lys Asn Ser Gln Asn Lys Tyr Ala Asn Ser Glu Leu Gly Tyr Lys
            260                 265                 270

Leu Pro Phe Ala Leu Gln Trp Ile Trp Pro Leu Pro Leu Ala Val Gly
        275                 280                 285

Ile Phe Phe Ala Pro Glu Ser Pro Trp Trp Leu Val Lys Lys Gly Arg
    290                 295                 300

Ile Asp Gln Ala Arg Arg Ser Leu Glu Arg Thr Leu Ser Gly Lys Gly
305                 310                 315                 320

Pro Glu Lys Glu Leu Leu Val Ser Met Glu Leu Asp Lys Ile Lys Thr
                325                 330                 335

Thr Ile Glu Lys Glu Gln Lys Met Ser Asp Glu Gly Thr Tyr Trp Asp
            340                 345                 350

-continued

```
        Cys Val Lys Asp Gly Ile Asn Arg Arg Thr Arg Ile Ala Cys Leu
                355                 360                 365

Cys Trp Ile Gly Gln Cys Ser Cys Gly Ala Ser Leu Ile Gly Tyr Ser
            370                 375                 380

Thr Tyr Phe Tyr Glu Lys Ala Gly Val Ser Thr Asp Thr Ala Phe Thr
        385                 390                 395                 400

Phe Ser Ile Ile Gln Tyr Cys Leu Gly Ile Ala Ala Thr Phe Ile Ser
                        405                 410                 415

Trp Trp Ala Ser Lys Tyr Cys Gly Arg Phe Asp Leu Tyr Ala Phe Gly
                    420                 425                 430

Leu Ala Phe Gln Ala Ile Met Phe Phe Ile Ile Gly Gly Leu Gly Cys
                435                 440                 445

Ser Asp Thr His Gly Ala Lys Met Gly Ser Gly Ala Leu Leu Met Val
            450                 455                 460

Val Ala Phe Phe Tyr Asn Leu Gly Ile Ala Pro Val Val Phe Cys Leu
        465                 470                 475                 480

Val Ser Glu Ile Pro Ser Ser Arg Leu Arg Thr Lys Thr Ile Ile Leu
                        485                 490                 495

Ala Arg Asn Ala Tyr Asn Val Ile Gln Val Val Val Thr Val Leu Ile
                    500                 505                 510

Met Tyr Gln Leu Asn Ser Glu Lys Trp Asn Trp Gly Ala Lys Ser Gly
                515                 520                 525

Phe Phe Trp Gly Gly Phe Cys Leu Ala Thr Leu Ala Trp Ala Val Val
            530                 535                 540

Asp Leu Pro Glu Thr Ala Gly Arg Thr Phe Ile Glu Ile Asn Glu Leu
        545                 550                 555                 560

Phe Arg Leu Gly Val Pro Ala Arg Lys Phe Lys Ser Thr Lys Val Asp
                        565                 570                 575

Pro Phe Ala Ala Ala Lys Ala Ala Ala Glu Ile Asn Val Lys Asp
                    580                 585                 590

Pro Lys Glu Asp Leu Glu Thr Ser Val Val Asp Glu Gly Arg Asn Thr
                595                 600                 605

Ser Ser Val Val Asn Lys
            610

<210> SEQ ID NO 43
<211> LENGTH: 1842
<212> TYPE: DNA
<213> ORGANISM: Artificial Sequence
<220> FEATURE:
<223> OTHER INFORMATION: Description of Artificial Sequence: Synthetic
      MAL31[L50P] polynucleotide
<220> FEATURE:
<221> NAME/KEY: CDS
<222> LOCATION: (1)..(1842)
<223> OTHER INFORMATION: Mal31p[Pro50]

<400> SEQUENCE: 43 atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
            20                  25                  30 tcg ata gag atg gag gag caa ggt aag aaa agt gat ttt gat ctt tcc     144
Ser Ile Glu Met Glu Glu Gln Gly Lys Lys Ser Asp Phe Asp Leu Ser
        35                  40                  45 cat cct gag tac ggt cca ggt tca cta ata cca aac gat aat aat gaa     192
His Pro Glu Tyr Gly Pro Gly Ser Leu Ile Pro Asn Asp Asn Asn Glu
```

|  |  |
|---|---|
| gaa gtc ccc gac ctt ctc gat gaa gct atg cag gac gcc aaa gag gca<br>Glu Val Pro Asp Leu Leu Asp Glu Ala Met Gln Asp Ala Lys Glu Ala<br>65                     70                        75                    80 | 240 |
| gat gaa agt gag agg gga atg cca ctc atg aca gct ttg aag aca tat<br>Asp Glu Ser Glu Arg Gly Met Pro Leu Met Thr Ala Leu Lys Thr Tyr<br>                  85                      90                    95 | 288 |
| cca aaa gct gct gct tgg tca cta tta gtt tcc aca aca ttg att caa<br>Pro Lys Ala Ala Ala Trp Ser Leu Leu Val Ser Thr Thr Leu Ile Gln<br>           100                    105                  110 | 336 |
| gag ggt tat gac aca gcc att cta gga gct ttc tat gcc ctg cct gtt<br>Glu Gly Tyr Asp Thr Ala Ile Leu Gly Ala Phe Tyr Ala Leu Pro Val<br>115                    120                    125 | 384 |
| ttt caa aaa aaa tat ggt tct ttg aat agc aat aca gga gat tat gaa<br>Phe Gln Lys Lys Tyr Gly Ser Leu Asn Ser Asn Thr Gly Asp Tyr Glu<br>130                    135                    140 | 432 |
| att tca gtt tcc tgg caa atc ggt cta tgt cta tgc tac atg gca ggt<br>Ile Ser Val Ser Trp Gln Ile Gly Leu Cys Leu Cys Tyr Met Ala Gly<br>145                    150                    155                  160 | 480 |
| gag att gtc ggt ttg caa atg act ggg cct tct gta gat tac atg ggc<br>Glu Ile Val Gly Leu Gln Met Thr Gly Pro Ser Val Asp Tyr Met Gly<br>                  165                    170                  175 | 528 |
| aac cgt tac act ctg atc atg gcg ttg ttt tta gcg gct ttc att<br>Asn Arg Tyr Thr Leu Ile Met Ala Leu Phe Phe Leu Ala Ala Phe Ile<br>           180                    185                  190 | 576 |
| ttc att ctg tat ttt tgc aag agt ttg ggt atg att gcc gtg gga cag<br>Phe Ile Leu Tyr Phe Cys Lys Ser Leu Gly Met Ile Ala Val Gly Gln<br>195                    200                    205 | 624 |
| gca ttg tgt ggt atg cca tgg ggt tgt ttc caa tgt ttg acc gtt tct<br>Ala Leu Cys Gly Met Pro Trp Gly Cys Phe Gln Cys Leu Thr Val Ser<br>210                    215                    220 | 672 |
| tat gct tct gaa att tgt cct ttg gcc cta aga tac tat ttg acg act<br>Tyr Ala Ser Glu Ile Cys Pro Leu Ala Leu Arg Tyr Tyr Leu Thr Thr<br>225                    230                    235                  240 | 720 |
| tat tct aat tta tgt tgg gcg ttc ggt caa ctt ttc gct gct ggt att<br>Tyr Ser Asn Leu Cys Trp Ala Phe Gly Gln Leu Phe Ala Ala Gly Ile<br>                  245                    250                  255 | 768 |
| atg aaa aat tcc cag aac aaa tat gcc aac tca gaa cta gga tat aag<br>Met Lys Asn Ser Gln Asn Lys Tyr Ala Asn Ser Glu Leu Gly Tyr Lys<br>           260                    265                  270 | 816 |
| cta cct ttt gct ttg cag tgg atc tgg ccc ctt cct ttg gcg gta ggt<br>Leu Pro Phe Ala Leu Gln Trp Ile Trp Pro Leu Pro Leu Ala Val Gly<br>           275                    280                  285 | 864 |
| att ttt ttt gca cca gag tct cca tgg tgg ctg gtt aaa aaa gga agg<br>Ile Phe Phe Ala Pro Glu Ser Pro Trp Trp Leu Val Lys Lys Gly Arg<br>290                    295                    300 | 912 |
| att gat caa gcg agg aga tca ctt gaa aga aca tta agt ggt aaa gga<br>Ile Asp Gln Ala Arg Arg Ser Leu Glu Arg Thr Leu Ser Gly Lys Gly<br>305                    310                    315                  320 | 960 |
| ccc gag aaa gaa tta cta gtg agt atg gaa ctc gat aaa atc aaa act<br>Pro Glu Lys Glu Leu Leu Val Ser Met Glu Leu Asp Lys Ile Lys Thr<br>                  325                    330                  335 | 1008 |
| act ata gaa aag gag cag aaa atg tct gat gaa gga act tac tgg gat<br>Thr Ile Glu Lys Glu Gln Lys Met Ser Asp Glu Gly Thr Tyr Trp Asp<br>           340                    345                  350 | 1056 |
| tgt gtg aaa gat ggt att aac agg aga aga acg aga ata gct tgt tta<br>Cys Val Lys Asp Gly Ile Asn Arg Arg Arg Thr Arg Ile Ala Cys Leu<br>355                    360                    365 | 1104 |
| tgt tgg atc ggt caa tgc tcc tgt ggt gca tca tta att ggt tat tca<br>Cys Trp Ile Gly Gln Cys Ser Cys Gly Ala Ser Leu Ile Gly Tyr Ser | 1152 |

```
                    370                 375                 380
act tac ttt tat gaa aaa gct ggt gtt agc act gat acg gct ttt act        1200
Thr Tyr Phe Tyr Glu Lys Ala Gly Val Ser Thr Asp Thr Ala Phe Thr
385                 390                 395                 400 ttc agt att atc caa tat tgt ctt ggt att gct gca acg ttt ata tcc        1248
Phe Ser Ile Ile Gln Tyr Cys Leu Gly Ile Ala Ala Thr Phe Ile Ser
            405                 410                 415 tgg tgg gct tca aaa tat tgt ggc aga ttt gac ctt tat gct ttt ggg        1296
Trp Trp Ala Ser Lys Tyr Cys Gly Arg Phe Asp Leu Tyr Ala Phe Gly
        420                 425                 430 ctg gct ttt cag gct att atg ttc ttc att atc ggt ggt tta gga tgt        1344
Leu Ala Phe Gln Ala Ile Met Phe Phe Ile Ile Gly Gly Leu Gly Cys
    435                 440                 445 tca gac act cat ggc gct aaa atg ggt agt ggt gct ctt cta atg gtt        1392
Ser Asp Thr His Gly Ala Lys Met Gly Ser Gly Ala Leu Leu Met Val
450                 455                 460 gtc gcg ttc ttt tac aac ctc ggt att gca cct gtt gtt ttt tgc tta        1440
Val Ala Phe Phe Tyr Asn Leu Gly Ile Ala Pro Val Val Phe Cys Leu
465                 470                 475                 480 gtg tct gaa ata ccg tct tca agg cta aga acc aaa aca att att ttg        1488
Val Ser Glu Ile Pro Ser Ser Arg Leu Arg Thr Lys Thr Ile Ile Leu
            485                 490                 495 gct cgt aat gct tac aat gtg atc caa gtt gta gtt aca gtt ttg atc        1536
Ala Arg Asn Ala Tyr Asn Val Ile Gln Val Val Val Thr Val Leu Ile
        500                 505                 510 atg tac caa ttg aac tca gag aaa tgg aat tgg ggt gct aaa tca ggc        1584
Met Tyr Gln Leu Asn Ser Glu Lys Trp Asn Trp Gly Ala Lys Ser Gly
    515                 520                 525 ttt ttc tgg gga gga ttt tgt ctg gcc act tta gct tgg gct gtt gtc        1632
Phe Phe Trp Gly Gly Phe Cys Leu Ala Thr Leu Ala Trp Ala Val Val
530                 535                 540 gat tta cca gaa acc gct ggc agg act ttt att gag ata aat gaa ttg        1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac        1728
Phe Arg Leu Gly Val Pro Ala Arg Lys Phe Lys Ser Thr Lys Val Asp
            565                 570                 575 cct ttt gca gct gcc aaa gca gca gct gca gaa att aat gtt aaa gat        1776
Pro Phe Ala Ala Ala Lys Ala Ala Ala Glu Ile Asn Val Lys Asp
        580                 585                 590 ccg aag gaa gat ttg gaa act tct gtg gta gat gaa ggg cga aac acc        1824
Pro Lys Glu Asp Leu Glu Thr Ser Val Val Asp Glu Gly Arg Asn Thr
    595                 600                 605 tca tct gtt gtg aac aaa                                                1842
Ser Ser Val Val Asn Lys
    610

<210> SEQ ID NO 44
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Asp Leu Ser
```

-continued

```
               35                  40                  45
His Pro Glu Tyr Gly Pro Gly Ser Leu Ile Pro Asn Asp Asn Glu
    50                  55                  60
Glu Val Pro Asp Leu Leu Asp Glu Ala Met Gln Asp Ala Lys Glu Ala
65                  70                  75                  80
Asp Glu Ser Glu Arg Gly Met Pro Leu Met Thr Ala Leu Lys Thr Tyr
                85                  90                  95
Pro Lys Ala Ala Ala Trp Ser Leu Leu Val Ser Thr Thr Leu Ile Gln
                100                 105                 110
Glu Gly Tyr Asp Thr Ala Ile Leu Gly Ala Phe Tyr Ala Leu Pro Val
                115                 120                 125
Phe Gln Lys Lys Tyr Gly Ser Leu Asn Ser Asn Thr Gly Asp Tyr Glu
        130                 135                 140
Ile Ser Val Ser Trp Gln Ile Gly Leu Cys Leu Cys Tyr Met Ala Gly
145                 150                 155                 160
Glu Ile Val Gly Leu Gln Met Thr Gly Pro Ser Val Asp Tyr Met Gly
                165                 170                 175
Asn Arg Tyr Thr Leu Ile Met Ala Leu Phe Phe Leu Ala Ala Phe Ile
                180                 185                 190
Phe Ile Leu Tyr Phe Cys Lys Ser Leu Gly Met Ile Ala Val Gly Gln
            195                 200                 205
Ala Leu Cys Gly Met Pro Trp Gly Cys Phe Gln Cys Leu Thr Val Ser
        210                 215                 220
Tyr Ala Ser Glu Ile Cys Pro Leu Ala Leu Arg Tyr Tyr Leu Thr Thr
225                 230                 235                 240
Tyr Ser Asn Leu Cys Trp Ala Phe Gly Gln Leu Phe Ala Ala Gly Ile
                245                 250                 255
Met Lys Asn Ser Gln Asn Lys Tyr Ala Asn Ser Glu Leu Gly Tyr Lys
                260                 265                 270
Leu Pro Phe Ala Leu Gln Trp Ile Trp Pro Leu Pro Leu Ala Val Gly
            275                 280                 285
Ile Phe Phe Ala Pro Glu Ser Pro Trp Trp Leu Val Lys Lys Gly Arg
    290                 295                 300
Ile Asp Gln Ala Arg Arg Ser Leu Glu Arg Thr Leu Ser Gly Lys Gly
305                 310                 315                 320
Pro Glu Lys Glu Leu Leu Val Ser Met Glu Leu Asp Lys Ile Lys Thr
                325                 330                 335
Thr Ile Glu Lys Glu Gln Lys Met Ser Asp Glu Gly Tyr Trp Asp
                340                 345                 350
Cys Val Lys Asp Gly Ile Asn Arg Arg Arg Thr Arg Ile Ala Cys Leu
    355                 360                 365
Cys Trp Ile Gly Gln Cys Ser Cys Gly Ala Ser Leu Ile Gly Tyr Ser
    370                 375                 380
Thr Tyr Phe Tyr Glu Lys Ala Gly Val Ser Thr Asp Thr Ala Phe Thr
385                 390                 395                 400
Phe Ser Ile Ile Gln Tyr Cys Leu Gly Ile Ala Ala Thr Phe Ile Ser
                405                 410                 415
Trp Trp Ala Ser Lys Tyr Cys Gly Arg Phe Asp Leu Tyr Ala Phe Gly
                420                 425                 430
Leu Ala Phe Gln Ala Ile Met Phe Ile Ile Gly Leu Gly Cys
            435                 440                 445
Ser Asp Thr His Gly Ala Lys Met Gly Ser Gly Ala Leu Leu Met Val
    450                 455                 460
```

```
Val Ala Phe Phe Tyr Asn Leu Gly Ile Ala Pro Val Val Phe Cys Leu
465                 470                 475                 480

Val Ser Glu Ile Pro Ser Ser Arg Leu Arg Thr Lys Thr Ile Ile Leu
            485                 490                 495

Ala Arg Asn Ala Tyr Asn Val Ile Gln Val Val Thr Val Leu Ile
                500                 505                 510

Met Tyr Gln Leu Asn Ser Glu Lys Trp Asn Trp Gly Ala Lys Ser Gly
            515                 520                 525

Phe Phe Trp Gly Gly Phe Cys Leu Ala Thr Leu Ala Trp Ala Val Val
    530                 535                 540

Asp Leu Pro Glu Thr Ala Gly Arg Thr Phe Ile Glu Ile Asn Glu Leu
545                 550                 555                 560

Phe Arg Leu Gly Val Pro Ala Arg Lys Phe Lys Ser Thr Lys Val Asp
                565                 570                 575

Pro Phe Ala Ala Ala Lys Ala Ala Ala Glu Ile Asn Val Lys Asp
                580                 585                 590

Pro Lys Glu Asp Leu Glu Thr Ser Val Val Asp Glu Gly Arg Asn Thr
            595                 600                 605

Ser Ser Val Val Asn Lys
    610

<210> SEQ ID NO 45
<211> LENGTH: 1842
<212> TYPE: DNA
<213> ORGANISM: Artificial Sequence
<220> FEATURE:
<223> OTHER INFORMATION: Description of Artificial Sequence: Synthetic
      MAL31[E51K] polynucleotide
<220> FEATURE:
<221> NAME/KEY: CDS
<222> LOCATION: (1)..(1842)
<223> OTHER INFORMATION: Mal31p[Lys51]

<400> SEQUENCE: 45 atg aag gga tta tcc tca tta ata aac aga aaa aaa gac agg aac gac     48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac    96
Ser His Leu Asp Glu Ile Glu Asn Gly Val Asn Ala Thr Glu Phe Asn
                20                  25                  30 tcg ata gag atg gag gag caa ggt aag aaa agt gat ttt gat ctt tcc   144
Ser Ile Glu Met Glu Glu Gln Gly Lys Lys Ser Asp Phe Asp Leu Ser
            35                  40                  45 cat ctt aag tac ggt cca ggt tca cta ata cca aac gat aat aat gaa   192
His Leu Lys Tyr Gly Pro Gly Ser Leu Ile Pro Asn Asp Asn Asn Glu
        50                  55                  60 gaa gtc ccc gac ctt ctc gat gaa gct atg cag gac gcc aaa gag gca   240
Glu Val Pro Asp Leu Leu Asp Glu Ala Met Gln Asp Ala Lys Glu Ala
65                  70                  75                  80 gat gaa agt gag agg gga atg cca ctc atg aca gct ttg aag aca tat   288
Asp Glu Ser Glu Arg Gly Met Pro Leu Met Thr Ala Leu Lys Thr Tyr
                85                  90                  95 cca aaa gct gct gct tgg tca cta tta gtt tcc aca aca ttg att caa   336
Pro Lys Ala Ala Ala Trp Ser Leu Leu Val Ser Thr Thr Leu Ile Gln
            100                 105                 110 gag ggt tat gac aca gcc att cta gga gct ttc tat gcc ctg cct gtt   384
Glu Gly Tyr Asp Thr Ala Ile Leu Gly Ala Phe Tyr Ala Leu Pro Val
        115                 120                 125 ttt caa aaa aaa tat ggt tct ttg aat agc aat aca gga gat tat gaa   432
Phe Gln Lys Lys Tyr Gly Ser Leu Asn Ser Asn Thr Gly Asp Tyr Glu
    130                 135                 140
```

```
att tca gtt tcc tgg caa atc ggt cta tgt cta tgc tac atg gca ggt       480
Ile Ser Val Ser Trp Gln Ile Gly Leu Cys Leu Cys Tyr Met Ala Gly
145                 150                 155                 160 gag att gtc ggt ttg caa atg act ggg cct tct gta gat tac atg ggc       528
Glu Ile Val Gly Leu Gln Met Thr Gly Pro Ser Val Asp Tyr Met Gly
                165                 170                 175 aac cgt tac act ctg atc atg gcg ttg ttc ttt tta gcg gct ttc att       576
Asn Arg Tyr Thr Leu Ile Met Ala Leu Phe Phe Leu Ala Ala Phe Ile
            180                 185                 190 ttc att ctg tat ttt tgc aag agt ttg ggt atg att gcc gtg gga cag       624
Phe Ile Leu Tyr Phe Cys Lys Ser Leu Gly Met Ile Ala Val Gly Gln
        195                 200                 205 gca ttg tgt ggt atg cca tgg ggt tgt ttc caa tgt ttg acc gtt tct       672
Ala Leu Cys Gly Met Pro Trp Gly Cys Phe Gln Cys Leu Thr Val Ser
    210                 215                 220 tat gct tct gaa att tgt cct ttg gcc cta aga tac tat ttg acg act       720
Tyr Ala Ser Glu Ile Cys Pro Leu Ala Leu Arg Tyr Tyr Leu Thr Thr
225                 230                 235                 240 tat tct aat tta tgt tgg gcg ttc ggt caa ctt ttc gct gct ggt att       768
Tyr Ser Asn Leu Cys Trp Ala Phe Gly Gln Leu Phe Ala Ala Gly Ile
                245                 250                 255 atg aaa aat tcc cag aac aaa tat gcc aac tca gaa cta gga tat aag       816
Met Lys Asn Ser Gln Asn Lys Tyr Ala Asn Ser Glu Leu Gly Tyr Lys
            260                 265                 270 cta cct ttt gct ttg cag tgg atc tgg ccc ctt cct ttg gcg gta ggt       864
Leu Pro Phe Ala Leu Gln Trp Ile Trp Pro Leu Pro Leu Ala Val Gly
        275                 280                 285 att ttt ttt gca cca gag tct cca tgg tgg ctg gtt aaa aaa gga agg       912
Ile Phe Phe Ala Pro Glu Ser Pro Trp Trp Leu Val Lys Lys Gly Arg
    290                 295                 300 att gat caa gcg agg aga tca ctt gaa aga aca tta agt ggt aaa gga       960
Ile Asp Gln Ala Arg Arg Ser Leu Glu Arg Thr Leu Ser Gly Lys Gly
305                 310                 315                 320 ccc gag aaa gaa tta cta gtg agt atg gaa ctc gat aaa atc aaa act      1008
Pro Glu Lys Glu Leu Leu Val Ser Met Glu Leu Asp Lys Ile Lys Thr
                325                 330                 335 act ata gaa aag gag cag aaa atg tct gat gaa gga act tac tgg gat      1056
Thr Ile Glu Lys Glu Gln Lys Met Ser Asp Glu Gly Thr Tyr Trp Asp
            340                 345                 350 tgt gtg aaa gat ggt att aac agg aga aga acg aga ata gct tgt tta      1104
Cys Val Lys Asp Gly Ile Asn Arg Arg Arg Thr Arg Ile Ala Cys Leu
        355                 360                 365 tgt tgg atc ggt caa tgc tcc tgt ggt gca tca tta att ggt tat tca      1152
Cys Trp Ile Gly Gln Cys Ser Cys Gly Ala Ser Leu Ile Gly Tyr Ser
    370                 375                 380 act tac ttt tat gaa aaa gct ggt gtt agc act gat acg gct ttt act      1200
Thr Tyr Phe Tyr Glu Lys Ala Gly Val Ser Thr Asp Thr Ala Phe Thr
385                 390                 395                 400 ttc agt att atc caa tat tgt ctt ggt att gct gca acg ttt ata tcc      1248
Phe Ser Ile Ile Gln Tyr Cys Leu Gly Ile Ala Ala Thr Phe Ile Ser
                405                 410                 415 tgg tgg gct tca aaa tat tgt ggc aga ttt gac ctt tat gct ttt ggg      1296
Trp Trp Ala Ser Lys Tyr Cys Gly Arg Phe Asp Leu Tyr Ala Phe Gly
            420                 425                 430 ctg gct ttt cag gct att atg ttc ttc att atc ggt ggt tta gga tgt      1344
Leu Ala Phe Gln Ala Ile Met Phe Phe Ile Ile Gly Gly Leu Gly Cys
        435                 440                 445 tca gac act cat ggc gct aaa atg ggt agt ggt gct ctt cta atg gtt      1392
Ser Asp Thr His Gly Ala Lys Met Gly Ser Gly Ala Leu Leu Met Val
    450                 455                 460
```

```
gtc gcg ttc ttt tac aac ctc ggt att gca cct gtt gtt ttt tgc tta    1440
Val Ala Phe Phe Tyr Asn Leu Gly Ile Ala Pro Val Val Phe Cys Leu
465                 470                 475                 480 gtg tct gaa ata ccg tct tca agg cta aga acc aaa aca att att ttg    1488
Val Ser Glu Ile Pro Ser Ser Arg Leu Arg Thr Lys Thr Ile Ile Leu
                485                 490                 495 gct cgt aat gct tac aat gtg atc caa gtt gta gtt aca gtt ttg atc    1536
Ala Arg Asn Ala Tyr Asn Val Ile Gln Val Val Val Thr Val Leu Ile
            500                 505                 510 atg tac caa ttg aac tca gag aaa tgg aat tgg ggt gct aaa tca ggc    1584
Met Tyr Gln Leu Asn Ser Glu Lys Trp Asn Trp Gly Ala Lys Ser Gly
        515                 520                 525 ttt ttc tgg gga gga ttt tgt ctg gcc act tta gct tgg gct gtt gtc    1632
Phe Phe Trp Gly Gly Phe Cys Leu Ala Thr Leu Ala Trp Ala Val Val
    530                 535                 540 gat tta cca gaa acc gct ggc agg act ttt att gag ata aat gaa ttg    1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac    1728
Phe Arg Leu Gly Val Pro Ala Arg Lys Phe Lys Ser Thr Lys Val Asp
                565                 570                 575 cct ttt gca gct gcc aaa gca gca gct gca gaa att aat gtt aaa gat    1776
Pro Phe Ala Ala Ala Lys Ala Ala Ala Glu Ile Asn Val Lys Asp
            580                 585                 590 ccg aag gaa gat ttg gaa act tct gtg gta gat gaa ggg cga aac acc    1824
Pro Lys Glu Asp Leu Glu Thr Ser Val Val Asp Glu Gly Arg Asn Thr
        595                 600                 605 tca tct gtt gtg aac aaa                                            1842
Ser Ser Val Val Asn Lys
    610

<210> SEQ ID NO 46
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Lys Gly Leu Ser Ser Leu Ile Asn Arg Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Asp Leu Ser
        35                  40                  45

His Leu Lys Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ala Phe Tyr Ala Leu Pro Val
        115                 120                 125

Phe Gln Lys Lys Tyr Gly Ser Leu Asn Ser Asn Thr Gly Asp Tyr Glu
    130                 135                 140

Ile Ser Val Ser Trp Gln Ile Gly Leu Cys Leu Cys Tyr Met Ala Gly
```

-continued

```
            145                 150                 155                 160
        Glu Ile Val Gly Leu Gln Met Thr Gly Pro Ser Val Asp Tyr Met Gly
                        165                 170                 175

Asn Arg Tyr Thr Leu Ile Met Ala Leu Phe Phe Leu Ala Ala Phe Ile
                        180                 185                 190

Phe Ile Leu Tyr Phe Cys Lys Ser Leu Gly Met Ile Ala Val Gly Gln
                        195                 200                 205

Ala Leu Cys Gly Met Pro Trp Gly Cys Phe Gln Cys Leu Thr Val Ser
                        210                 215                 220

Tyr Ala Ser Glu Ile Cys Pro Leu Ala Leu Arg Tyr Tyr Leu Thr Thr
        225                 230                 235                 240

Tyr Ser Asn Leu Cys Trp Ala Phe Gly Gln Leu Phe Ala Ala Gly Ile
                        245                 250                 255

Met Lys Asn Ser Gln Asn Lys Tyr Ala Asn Ser Glu Leu Gly Tyr Lys
                        260                 265                 270

Leu Pro Phe Ala Leu Gln Trp Ile Trp Pro Leu Pro Leu Ala Val Gly
                        275                 280                 285

Ile Phe Phe Ala Pro Glu Ser Pro Trp Trp Leu Val Lys Lys Gly Arg
        290                 295                 300

Ile Asp Gln Ala Arg Arg Ser Leu Glu Arg Thr Leu Ser Gly Lys Gly
        305                 310                 315                 320

Pro Glu Lys Glu Leu Leu Val Ser Met Glu Leu Asp Lys Ile Lys Thr
                        325                 330                 335

Thr Ile Glu Lys Glu Gln Lys Met Ser Asp Glu Gly Thr Tyr Trp Asp
                        340                 345                 350

Cys Val Lys Asp Gly Ile Asn Arg Arg Arg Thr Arg Ile Ala Cys Leu
                        355                 360                 365

Cys Trp Ile Gly Gln Cys Ser Cys Gly Ala Ser Leu Ile Gly Tyr Ser
                        370                 375                 380

Thr Tyr Phe Tyr Glu Lys Ala Gly Val Ser Thr Asp Thr Ala Phe Thr
        385                 390                 395                 400

Phe Ser Ile Ile Gln Tyr Cys Leu Gly Ile Ala Ala Thr Phe Ile Ser
                        405                 410                 415

Trp Trp Ala Ser Lys Tyr Cys Gly Arg Phe Asp Leu Tyr Ala Phe Gly
                        420                 425                 430

Leu Ala Phe Gln Ala Ile Met Phe Phe Ile Ile Gly Gly Leu Gly Cys
                        435                 440                 445

Ser Asp Thr His Gly Ala Lys Met Gly Ser Gly Ala Leu Leu Met Val
        450                 455                 460

Val Ala Phe Phe Tyr Asn Leu Gly Ile Ala Pro Val Val Phe Cys Leu
        465                 470                 475                 480

Val Ser Glu Ile Pro Ser Ser Arg Leu Arg Thr Lys Thr Ile Ile Leu
                        485                 490                 495

Ala Arg Asn Ala Tyr Asn Val Ile Gln Val Val Thr Val Leu Ile
                        500                 505                 510

Met Tyr Gln Leu Asn Ser Glu Lys Trp Asn Trp Gly Ala Lys Ser Gly
                        515                 520                 525

Phe Phe Trp Gly Gly Phe Cys Leu Ala Thr Leu Ala Trp Ala Val Val
                        530                 535                 540

Asp Leu Pro Glu Thr Ala Gly Arg Thr Phe Ile Glu Ile Asn Glu Leu
        545                 550                 555                 560

Phe Arg Leu Gly Val Pro Ala Arg Lys Phe Lys Ser Thr Lys Val Asp
                        565                 570                 575
```

-continued

```
Pro Phe Ala Ala Ala Lys Ala Ala Ala Glu Ile Asn Val Lys Asp
            580                 585                 590

Pro Lys Glu Asp Leu Glu Thr Ser Val Val Asp Glu Gly Arg Asn Thr
    595                 600                 605

Ser Ser Val Val Asn Lys
    610

<210> SEQ ID NO 47
<211> LENGTH: 1842
<212> TYPE: DNA
<213> ORGANISM: Artificial Sequence
<220> FEATURE:
<223> OTHER INFORMATION: Description of Artificial Sequence: Synthetic
      MAL31[L50F,E51K] polynucleotide
<220> FEATURE:
<221> NAME/KEY: CDS
<222> LOCATION: (1)..(1842)
<223> OTHER INFORMATION: Mal31p[Phe50,Lys51]

<400> SEQUENCE: 47 atg aag gga tta tcc tca tta ata aac aga aaa aaa gac agg aac gac     48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac     96
Ser His Leu Asp Glu Ile Glu Asn Gly Val Asn Ala Thr Glu Phe Asn
            20                  25                  30 tcg ata gag atg gag gag caa ggt aag aaa agt gat ttt gat ctt tcc    144
Ser Ile Glu Met Glu Glu Gln Gly Lys Lys Ser Asp Phe Asp Leu Ser
        35                  40                  45 cat ttt aag tac ggt cca ggt tca cta ata cca aac gat aat aat gaa    192
His Phe Lys Tyr Gly Pro Gly Ser Leu Ile Pro Asn Asp Asn Asn Glu
    50                  55                  60 gaa gtc ccc gac ctt ctc gat gaa gct atg cag gac gcc aaa gag gca    240
Glu Val Pro Asp Leu Leu Asp Glu Ala Met Gln Asp Ala Lys Glu Ala
65                  70                  75                  80 gat gaa agt gag agg gga atg cca ctc atg aca gct ttg aag aca tat    288
Asp Glu Ser Glu Arg Gly Met Pro Leu Met Thr Ala Leu Lys Thr Tyr
                85                  90                  95 cca aaa gct gct gct tgg tca cta tta gtt tcc aca aca ttg att caa    336
Pro Lys Ala Ala Ala Trp Ser Leu Leu Val Ser Thr Thr Leu Ile Gln
            100                 105                 110 gag ggt tat gac aca gcc att cta gga gct ttc tat gcc ctg cct gtt    384
Glu Gly Tyr Asp Thr Ala Ile Leu Gly Ala Phe Tyr Ala Leu Pro Val
        115                 120                 125 ttt caa aaa aaa tat ggt tct ttg aat agc aat aca gga gat tat gaa    432
Phe Gln Lys Lys Tyr Gly Ser Leu Asn Ser Asn Thr Gly Asp Tyr Glu
    130                 135                 140 att tca gtt tcc tgg caa atc ggt cta tgt cta tgc tac atg gca ggt    480
Ile Ser Val Ser Trp Gln Ile Gly Leu Cys Leu Cys Tyr Met Ala Gly
145                 150                 155                 160 gag att gtc ggt ttg caa atg act ggg cct tct gta gat tac atg ggc    528
Glu Ile Val Gly Leu Gln Met Thr Gly Pro Ser Val Asp Tyr Met Gly
                165                 170                 175 aac cgt tac act ctg atc atg gcg ttg ttt tta gcg gct ttc att        576
Asn Arg Tyr Thr Leu Ile Met Ala Leu Phe Phe Leu Ala Ala Phe Ile
            180                 185                 190 ttc att ctg tat ttt tgc aag agt ttg ggt atg att gcc gtg gga cag    624
Phe Ile Leu Tyr Phe Cys Lys Ser Leu Gly Met Ile Ala Val Gly Gln
        195                 200                 205 gca ttg tgt ggt atg cca tgg ggt tgt ttc caa tgt ttg acc gtt tct    672
Ala Leu Cys Gly Met Pro Trp Gly Cys Phe Gln Cys Leu Thr Val Ser
    210                 215                 220
```

```
                                                          -continued
tat gct tct gaa att tgt cct ttg gcc cta aga tac tat ttg acg act      720
Tyr Ala Ser Glu Ile Cys Pro Leu Ala Leu Arg Tyr Tyr Leu Thr Thr
225             230                 235                 240 tat tct aat tta tgt tgg gcg ttc ggt caa ctt ttc gct gct ggt att      768
Tyr Ser Asn Leu Cys Trp Ala Phe Gly Gln Leu Phe Ala Ala Gly Ile
                245                 250                 255 atg aaa aat tcc cag aac aaa tat gcc aac tca gaa cta gga tat aag      816
Met Lys Asn Ser Gln Asn Lys Tyr Ala Asn Ser Glu Leu Gly Tyr Lys
            260                 265                 270 cta cct ttt gct ttg cag tgg atc tgg ccc ctt cct ttg gcg gta ggt      864
Leu Pro Phe Ala Leu Gln Trp Ile Trp Pro Leu Pro Leu Ala Val Gly
        275                 280                 285 att ttt ttt gca cca gag tct cca tgg tgg ctg gtt aaa aaa gga agg      912
Ile Phe Phe Ala Pro Glu Ser Pro Trp Trp Leu Val Lys Lys Gly Arg
    290                 295                 300 att gat caa gcg agg aga tca ctt gaa aga aca tta agt ggt aaa gga      960
Ile Asp Gln Ala Arg Arg Ser Leu Glu Arg Thr Leu Ser Gly Lys Gly
305             310                 315                 320 ccc gag aaa gaa tta cta gtg agt atg gaa ctc gat aaa atc aaa act     1008
Pro Glu Lys Glu Leu Leu Val Ser Met Glu Leu Asp Lys Ile Lys Thr
                325                 330                 335 act ata gaa aag gag cag aaa atg tct gat gaa gga act tac tgg gat     1056
Thr Ile Glu Lys Glu Gln Lys Met Ser Asp Glu Gly Thr Tyr Trp Asp
            340                 345                 350 tgt gtg aaa gat ggt att aac agg aga aga acg aga ata gct tgt tta     1104
Cys Val Lys Asp Gly Ile Asn Arg Arg Arg Thr Arg Ile Ala Cys Leu
        355                 360                 365 tgt tgg atc ggt caa tgc tcc tgt ggt gca tca tta att ggt tat tca     1152
Cys Trp Ile Gly Gln Cys Ser Cys Gly Ala Ser Leu Ile Gly Tyr Ser
    370                 375                 380 act tac ttt tat gaa aaa gct ggt gtt agc act gat acg gct ttt act     1200
Thr Tyr Phe Tyr Glu Lys Ala Gly Val Ser Thr Asp Thr Ala Phe Thr
385             390                 395                 400 ttc agt att atc caa tat tgt ctt ggt att gct gca acg ttt ata tcc     1248
Phe Ser Ile Ile Gln Tyr Cys Leu Gly Ile Ala Ala Thr Phe Ile Ser
                405                 410                 415 tgg tgg gct tca aaa tat tgt ggc aga ttt gac ctt tat gct ttt ggg     1296
Trp Trp Ala Ser Lys Tyr Cys Gly Arg Phe Asp Leu Tyr Ala Phe Gly
            420                 425                 430 ctg gct ttt cag gct att atg ttc ttc att atc ggt ggt tta gga tgt     1344
Leu Ala Phe Gln Ala Ile Met Phe Phe Ile Ile Gly Gly Leu Gly Cys
        435                 440                 445 tca gac act cat ggc gct aaa atg ggt agt ggt gct ctt cta atg gtt     1392
Ser Asp Thr His Gly Ala Lys Met Gly Ser Gly Ala Leu Leu Met Val
    450                 455                 460 gtc gcg ttc ttt tac aac ctc ggt att gca cct gtt gtt ttt tgc tta     1440
Val Ala Phe Phe Tyr Asn Leu Gly Ile Ala Pro Val Val Phe Cys Leu
465             470                 475                 480 gtg tct gaa ata ccg tct tca agg cta aga acc aaa aca att att ttg     1488
Val Ser Glu Ile Pro Ser Ser Arg Leu Arg Thr Lys Thr Ile Ile Leu
                485                 490                 495 gct cgt aat gct tac aat gtg atc caa gtt gta gtt aca gtt ttg atc     1536
Ala Arg Asn Ala Tyr Asn Val Ile Gln Val Val Val Thr Val Leu Ile
            500                 505                 510 atg tac caa ttg aac tca gag aaa tgg aat tgg ggt gct aaa tca ggc     1584
Met Tyr Gln Leu Asn Ser Glu Lys Trp Asn Trp Gly Ala Lys Ser Gly
        515                 520                 525 ttt ttc tgg gga gga ttt tgt ctg gcc act tta gct tgg gct gtt gtc     1632
Phe Phe Trp Gly Gly Phe Cys Leu Ala Thr Leu Ala Trp Ala Val Val
    530                 535                 540
```

```
gat tta cca gaa acc gct ggc agg act ttt att gag ata aat gaa ttg    1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac    1728
Phe Arg Leu Gly Val Pro Ala Arg Lys Phe Lys Ser Thr Lys Val Asp
                565                 570                 575 cct ttt gca gct gcc aaa gca gca gct gca gaa att aat gtt aaa gat    1776
Pro Phe Ala Ala Ala Lys Ala Ala Ala Ala Glu Ile Asn Val Lys Asp
            580                 585                 590 ccg aag gaa gat ttg gaa act tct gtg gta gat gaa ggg cga aac acc    1824
Pro Lys Glu Asp Leu Glu Thr Ser Val Val Asp Glu Gly Arg Asn Thr
        595                 600                 605 tca tct gtt gtg aac aaa                                            1842
Ser Ser Val Val Asn Lys
    610

<210> SEQ ID NO 48
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Asp Leu Ser
        35                  40                  45

His Phe Lys Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ala Phe Tyr Ala Leu Pro Val
        115                 120                 125

Phe Gln Lys Lys Tyr Gly Ser Leu Asn Ser Asn Thr Gly Asp Tyr Glu
    130                 135                 140

Ile Ser Val Ser Trp Gln Ile Gly Leu Cys Leu Cys Tyr Met Ala Gly
145                 150                 155                 160

Glu Ile Val Gly Leu Gln Met Thr Gly Pro Ser Val Asp Tyr Met Gly
                165                 170                 175

Asn Arg Tyr Thr Leu Ile Met Ala Leu Phe Phe Leu Ala Ala Phe Ile
            180                 185                 190

Phe Ile Leu Tyr Phe Cys Lys Ser Leu Gly Met Ile Ala Val Gly Gln
        195                 200                 205

Ala Leu Cys Gly Met Pro Trp Gly Cys Phe Gln Cys Leu Thr Val Ser
    210                 215                 220

Tyr Ala Ser Glu Ile Cys Pro Leu Ala Leu Arg Tyr Tyr Leu Thr Thr
225                 230                 235                 240

Tyr Ser Asn Leu Cys Trp Ala Phe Gly Gln Leu Phe Ala Ala Gly Ile
                245                 250                 255

Met Lys Asn Ser Gln Asn Lys Tyr Ala Asn Ser Glu Leu Gly Tyr Lys
```

```
                    260                 265                 270
Leu Pro Phe Ala Leu Gln Trp Ile Trp Pro Leu Pro Leu Ala Val Gly
            275                 280                 285
Ile Phe Phe Ala Pro Glu Ser Pro Trp Trp Leu Val Lys Lys Gly Arg
        290                 295                 300
Ile Asp Gln Ala Arg Arg Ser Leu Glu Arg Thr Leu Ser Gly Lys Gly
305                 310                 315                 320
Pro Glu Lys Glu Leu Leu Val Ser Met Glu Leu Asp Lys Ile Lys Thr
                325                 330                 335
Thr Ile Glu Lys Glu Gln Lys Met Ser Asp Glu Gly Thr Tyr Trp Asp
            340                 345                 350
Cys Val Lys Asp Gly Ile Asn Arg Arg Thr Arg Ile Ala Cys Leu
        355                 360                 365
Cys Trp Ile Gly Gln Cys Ser Cys Gly Ala Ser Leu Ile Gly Tyr Ser
        370                 375                 380
Thr Tyr Phe Tyr Glu Lys Ala Gly Val Ser Thr Asp Thr Ala Phe Thr
385                 390                 395                 400
Phe Ser Ile Ile Gln Tyr Cys Leu Gly Ile Ala Ala Thr Phe Ile Ser
                405                 410                 415
Trp Trp Ala Ser Lys Tyr Cys Gly Arg Phe Asp Leu Tyr Ala Phe Gly
            420                 425                 430
Leu Ala Phe Gln Ala Ile Met Phe Phe Ile Ile Gly Gly Leu Gly Cys
        435                 440                 445
Ser Asp Thr His Gly Ala Lys Met Gly Ser Gly Ala Leu Leu Met Val
        450                 455                 460
Val Ala Phe Phe Tyr Asn Leu Gly Ile Ala Pro Val Val Phe Cys Leu
465                 470                 475                 480
Val Ser Glu Ile Pro Ser Ser Arg Leu Arg Thr Lys Thr Ile Ile Leu
                485                 490                 495
Ala Arg Asn Ala Tyr Asn Val Ile Gln Val Val Val Thr Val Leu Ile
            500                 505                 510
Met Tyr Gln Leu Asn Ser Glu Lys Trp Asn Trp Gly Ala Lys Ser Gly
        515                 520                 525
Phe Phe Trp Gly Gly Phe Cys Leu Ala Thr Leu Ala Trp Ala Val Val
        530                 535                 540
Asp Leu Pro Glu Thr Ala Gly Arg Thr Phe Ile Glu Ile Asn Glu Leu
545                 550                 555                 560
Phe Arg Leu Gly Val Pro Ala Arg Lys Phe Lys Ser Thr Lys Val Asp
                565                 570                 575
Pro Phe Ala Ala Ala Lys Ala Ala Ala Glu Ile Asn Val Lys Asp
            580                 585                 590
Pro Lys Glu Asp Leu Glu Thr Ser Val Val Asp Glu Gly Arg Asn Thr
        595                 600                 605
Ser Ser Val Val Asn Lys
    610

<210> SEQ ID NO 49
<211> LENGTH: 1842
<212> TYPE: DNA
<213> ORGANISM: Artificial Sequence
<220> FEATURE:
<223> OTHER INFORMATION: Description of Artificial Sequence: Synthetic
      MAL31[H49R] polynucleotide f
<220> FEATURE:
<221> NAME/KEY: CDS
<222> LOCATION: (1)..(1842)
<223> OTHER INFORMATION: Mal31p[Arg49]
```

<400> SEQUENCE: 49

```
atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
            20                  25                  30 tcg ata gag atg gag gag caa ggt aag aaa agt gat ttt gat ctt tcc     144
Ser Ile Glu Met Glu Glu Gln Gly Lys Lys Ser Asp Phe Asp Leu Ser
        35                  40                  45 cgt ctt gag tac ggt cca ggt tca cta ata cca aac gat aat aat gaa     192
Arg Leu Glu Tyr Gly Pro Gly Ser Leu Ile Pro Asn Asp Asn Asn Glu
50                  55                  60 gaa gtc ccc gac ctt ctc gat gaa gct atg cag gac gcc aaa gag gca     240
Glu Val Pro Asp Leu Leu Asp Glu Ala Met Gln Asp Ala Lys Glu Ala
65                  70                  75                  80 gat gaa agt gag agg gga atg cca ctc atg aca gct ttg aag aca tat     288
Asp Glu Ser Glu Arg Gly Met Pro Leu Met Thr Ala Leu Lys Thr Tyr
                85                  90                  95 cca aaa gct gct gct tgg tca cta tta gtt tcc aca aca ttg att caa     336
Pro Lys Ala Ala Ala Trp Ser Leu Leu Val Ser Thr Thr Leu Ile Gln
            100                 105                 110 gag ggt tat gac aca gcc att cta gga gct ttc tat gcc ctg cct gtt     384
Glu Gly Tyr Asp Thr Ala Ile Leu Gly Ala Phe Tyr Ala Leu Pro Val
        115                 120                 125 ttt caa aaa aaa tat ggt tct ttg aat agc aat aca gga gat tat gaa     432
Phe Gln Lys Lys Tyr Gly Ser Leu Asn Ser Asn Thr Gly Asp Tyr Glu
    130                 135                 140 att tca gtt tcc tgg caa atc ggt cta tgt cta tgc tac atg gca ggt     480
Ile Ser Val Ser Trp Gln Ile Gly Leu Cys Leu Cys Tyr Met Ala Gly
145                 150                 155                 160 gag att gtc ggt ttg caa atg act ggg cct tct gta gat tac atg ggc     528
Glu Ile Val Gly Leu Gln Met Thr Gly Pro Ser Val Asp Tyr Met Gly
                165                 170                 175 aac cgt tac act ctg atc atg gcg ttg ttc ttt tta gcg gct ttc att     576
Asn Arg Tyr Thr Leu Ile Met Ala Leu Phe Phe Leu Ala Ala Phe Ile
            180                 185                 190 ttc att ctg tat ttt tgc aag agt ttg ggt atg att gcc gtg gga cag     624
Phe Ile Leu Tyr Phe Cys Lys Ser Leu Gly Met Ile Ala Val Gly Gln
        195                 200                 205 gca ttg tgt ggt atg cca tgg ggt tgt ttc caa tgt ttg acc gtt tct     672
Ala Leu Cys Gly Met Pro Trp Gly Cys Phe Gln Cys Leu Thr Val Ser
    210                 215                 220 tat gct tct gaa att tgt cct ttg gcc cta aga tac tat ttg acg act     720
Tyr Ala Ser Glu Ile Cys Pro Leu Ala Leu Arg Tyr Tyr Leu Thr Thr
225                 230                 235                 240 tat tct aat tta tgt tgg gcg ttc ggt caa ctt ttc gct gct ggt att     768
Tyr Ser Asn Leu Cys Trp Ala Phe Gly Gln Leu Phe Ala Ala Gly Ile
                245                 250                 255 atg aaa aat tcc cag aac aaa tat gcc aac tca gaa cta gga tat aag     816
Met Lys Asn Ser Gln Asn Lys Tyr Ala Asn Ser Glu Leu Gly Tyr Lys
            260                 265                 270 cta cct ttt gct ttg cag tgg atc tgg ccc ctt cct ttg gcg gta ggt     864
Leu Pro Phe Ala Leu Gln Trp Ile Trp Pro Leu Pro Leu Ala Val Gly
        275                 280                 285 att ttt ttt gca cca gag tct cca tgg tgg ctg gtt aaa aaa gga agg     912
Ile Phe Phe Ala Pro Glu Ser Pro Trp Trp Leu Val Lys Lys Gly Arg
    290                 295                 300 att gat caa gcg agg aga tca ctt gaa aga aca tta agt ggt aaa gga     960
Ile Asp Gln Ala Arg Arg Ser Leu Glu Arg Thr Leu Ser Gly Lys Gly
```

| | | | | | | | | | | | | | |
|---|---|---|---|---|---|---|---|---|---|---|---|---|---|
| Ile | Asp | Gln | Ala | Arg | Arg | Ser | Leu | Glu | Arg | Thr | Leu | Ser | Gly | Lys | Gly |
| 305 | | | | | 310 | | | | | 315 | | | | | 320 |

```
ccc gag aaa gaa tta cta gtg agt atg gaa ctc gat aaa atc aaa act      1008
Pro Glu Lys Glu Leu Leu Val Ser Met Glu Leu Asp Lys Ile Lys Thr
            325                 330                 335 act ata gaa aag gag cag aaa atg tct gat gaa gga act tac tgg gat      1056
Thr Ile Glu Lys Glu Gln Lys Met Ser Asp Glu Gly Thr Tyr Trp Asp
        340                 345                 350 tgt gtg aaa gat ggt att aac agg aga aga acg aga ata gct tgt tta      1104
Cys Val Lys Asp Gly Ile Asn Arg Arg Arg Thr Arg Ile Ala Cys Leu
            355                 360                 365 tgt tgg atc ggt caa tgc tcc tgt ggt gca tca tta att ggt tat tca      1152
Cys Trp Ile Gly Gln Cys Ser Cys Gly Ala Ser Leu Ile Gly Tyr Ser
370                 375                 380 act tac ttt tat gaa aaa gct ggt gtt agc act gat acg gct ttt act      1200
Thr Tyr Phe Tyr Glu Lys Ala Gly Val Ser Thr Asp Thr Ala Phe Thr
385                 390                 395                 400 ttc agt att atc caa tat tgt ctt ggt att gct gca acg ttt ata tcc      1248
Phe Ser Ile Ile Gln Tyr Cys Leu Gly Ile Ala Ala Thr Phe Ile Ser
                405                 410                 415 tgg tgg gct tca aaa tat tgt ggc aga ttt gac ctt tat gct ttt ggg      1296
Trp Trp Ala Ser Lys Tyr Cys Gly Arg Phe Asp Leu Tyr Ala Phe Gly
            420                 425                 430 ctg gct ttt cag gct att atg ttc ttc att atc ggt ggt tta gga tgt      1344
Leu Ala Phe Gln Ala Ile Met Phe Phe Ile Ile Gly Gly Leu Gly Cys
        435                 440                 445 tca gac act cat ggc gct aaa atg ggt agt ggt gct ctt cta atg gtt      1392
Ser Asp Thr His Gly Ala Lys Met Gly Ser Gly Ala Leu Leu Met Val
450                 455                 460 gtc gcg ttc ttt tac aac ctc ggt att gca cct gtt gtt ttt tgc tta      1440
Val Ala Phe Phe Tyr Asn Leu Gly Ile Ala Pro Val Val Phe Cys Leu
465                 470                 475                 480 gtg tct gaa ata ccg tct tca agg cta aga acc aaa aca att att ttg      1488
Val Ser Glu Ile Pro Ser Ser Arg Leu Arg Thr Lys Thr Ile Ile Leu
                485                 490                 495 gct cgt aat gct tac aat gtg atc caa gtt gta gtt aca gtt ttg atc      1536
Ala Arg Asn Ala Tyr Asn Val Ile Gln Val Val Val Thr Val Leu Ile
            500                 505                 510 atg tac caa ttg aac tca gag aaa tgg aat tgg ggt gct aaa tca ggc      1584
Met Tyr Gln Leu Asn Ser Glu Lys Trp Asn Trp Gly Ala Lys Ser Gly
        515                 520                 525 ttt ttc tgg gga gga ttt tgt ctg gcc act tta gct tgg gct gtt gtc      1632
Phe Phe Trp Gly Gly Phe Cys Leu Ala Thr Leu Ala Trp Ala Val Val
530                 535                 540 gat tta cca gaa acc gct ggc agg act ttt att gag ata aat gaa ttg      1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac      1728
Phe Arg Leu Gly Val Pro Ala Arg Lys Phe Lys Ser Thr Lys Val Asp
                565                 570                 575 cct ttt gca gct gcc aaa gca gca gct gca gaa att aat gtt aaa gat      1776
Pro Phe Ala Ala Ala Lys Ala Ala Ala Glu Ile Asn Val Lys Asp
            580                 585                 590 ccg aag gaa gat ttg gaa act tct gtg gta gat gaa ggg cga aac acc      1824
Pro Lys Glu Asp Leu Glu Thr Ser Val Val Asp Glu Gly Arg Asn Thr
        595                 600                 605 tca tct gtt gtg aac aaa                                              1842
Ser Ser Val Val Asn Lys
            610
```

<210> SEQ ID NO 50
<211> LENGTH: 614
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Asp Leu Ser
        35                  40                  45

Arg Leu Glu Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ala Phe Tyr Ala Leu Pro Val
        115                 120                 125

Phe Gln Lys Lys Tyr Gly Ser Leu Asn Ser Asn Thr Gly Asp Tyr Glu
    130                 135                 140

Ile Ser Val Ser Trp Gln Ile Gly Leu Cys Leu Cys Tyr Met Ala Gly
145                 150                 155                 160

Glu Ile Val Gly Leu Gln Met Thr Gly Pro Ser Val Asp Tyr Met Gly
                165                 170                 175

Asn Arg Tyr Thr Leu Ile Met Ala Leu Phe Phe Leu Ala Ala Phe Ile
            180                 185                 190

Phe Ile Leu Tyr Phe Cys Lys Ser Leu Gly Met Ile Ala Val Gly Gln
        195                 200                 205

Ala Leu Cys Gly Met Pro Trp Gly Cys Phe Gln Cys Leu Thr Val Ser
    210                 215                 220

Tyr Ala Ser Glu Ile Cys Pro Leu Ala Leu Arg Tyr Tyr Leu Thr Thr
225                 230                 235                 240

Tyr Ser Asn Leu Cys Trp Ala Phe Gly Gln Leu Phe Ala Ala Gly Ile
                245                 250                 255

Met Lys Asn Ser Gln Asn Lys Tyr Ala Asn Ser Glu Leu Gly Tyr Lys
            260                 265                 270

Leu Pro Phe Ala Leu Gln Trp Ile Trp Pro Leu Pro Leu Ala Val Gly
        275                 280                 285

Ile Phe Phe Ala Pro Glu Ser Pro Trp Trp Leu Val Lys Lys Gly Arg
    290                 295                 300

Ile Asp Gln Ala Arg Arg Ser Leu Glu Arg Thr Leu Ser Gly Lys Gly
305                 310                 315                 320

Pro Glu Lys Glu Leu Leu Val Ser Met Glu Leu Asp Lys Ile Lys Thr
                325                 330                 335

Thr Ile Glu Lys Glu Gln Lys Met Ser Asp Glu Gly Thr Tyr Trp Asp
            340                 345                 350

Cys Val Lys Asp Gly Ile Asn Arg Arg Arg Thr Arg Ile Ala Cys Leu
        355                 360                 365

Cys Trp Ile Gly Gln Cys Ser Cys Gly Ala Ser Leu Ile Gly Tyr Ser
```

```
                   370             375             380
Thr Tyr Phe Tyr Glu Lys Ala Gly Val Ser Thr Asp Thr Ala Phe Thr
385                 390                 395                 400

Phe Ser Ile Ile Gln Tyr Cys Leu Gly Ile Ala Ala Thr Phe Ile Ser
                405                 410                 415

Trp Trp Ala Ser Lys Tyr Cys Gly Arg Phe Asp Leu Tyr Ala Phe Gly
            420                 425                 430

Leu Ala Phe Gln Ala Ile Met Phe Phe Ile Ile Gly Gly Leu Gly Cys
        435                 440                 445

Ser Asp Thr His Gly Ala Lys Met Gly Ser Gly Ala Leu Leu Met Val
    450                 455                 460

Val Ala Phe Phe Tyr Asn Leu Gly Ile Ala Pro Val Val Phe Cys Leu
465                 470                 475                 480

Val Ser Glu Ile Pro Ser Ser Arg Leu Arg Thr Lys Thr Ile Ile Leu
                485                 490                 495

Ala Arg Asn Ala Tyr Asn Val Ile Gln Val Val Val Thr Val Leu Ile
            500                 505                 510

Met Tyr Gln Leu Asn Ser Glu Lys Trp Asn Trp Gly Ala Lys Ser Gly
        515                 520                 525

Phe Phe Trp Gly Gly Phe Cys Leu Ala Thr Leu Ala Trp Ala Val Val
    530                 535                 540

Asp Leu Pro Glu Thr Ala Gly Arg Thr Phe Ile Glu Ile Asn Glu Leu
545                 550                 555                 560

Phe Arg Leu Gly Val Pro Ala Arg Lys Phe Lys Ser Thr Lys Val Asp
                565                 570                 575

Pro Phe Ala Ala Ala Lys Ala Ala Ala Glu Ile Asn Val Lys Asp
            580                 585                 590

Pro Lys Glu Asp Leu Glu Thr Ser Val Val Asp Glu Gly Arg Asn Thr
        595                 600                 605

Ser Ser Val Val Asn Lys
    610

<210> SEQ ID NO 51
<211> LENGTH: 1845
<212> TYPE: DNA
<213> ORGANISM: Saccharomyces cerevisiae

<400> SEQUENCE: 51
atgaagggat tatcctcatt aataaacaga aaaaaagaca ggaacgactc acacttagat      60
gagatcgaga atggcgtgaa cgctaccgaa ttcaactcga tagagatgga ggagcaaggt     120
aagaaaagtg attttggtct ttcccatcat gagtacggtc caggttcact aataccaaac     180
gataataatg aagaagtccc cgaccttctc gatgaagcta tgcaggacgc caaagaggca     240
gatgaaagtg agaggggaat gccactcatg acagctttga agacatatcc aaaagctgct     300
gcttggtcac tattagtttc cacaacattg attcaagagg ttatgacaca agccattcta     360
ggagctttct atgccctgcc tgttttcaa aaaaaatatg gttctttgaa tagcaataca     420
ggagattatg aaatttcagt ttcttggcaa atcggtctat gtctatgcta catggcaggt     480
gaaattgtgg ggctacagct aacgggggcc tccgtggatc ttgttggaaa tcgttacaca     540
ttgatcatgg cgttgttctt tttagcggct ttcattttca ttctgtattt ttgcaagagt     600
ttgggtatga ttgccgtggg acaggcattg tgtggtatgc catggggttg tttccaatgt     660
ttgaccgttt cttatgcttc tgaaatttgt cctttggccc taagatacta tttgacgact     720
tattctaatt tatgttggac gttcggtcaa cttttcgctg ctggtattat gaaaaattcc     780
```

-continued

```
cagaacaaat atgccaactc agaactagga tataagctac cttttgcttt gcagtggatc    840
tggccccttc ctttggcggt aggtattttt tttgcaccag agtctccatg gtggctggtt    900
aaaaaaggaa ggattgatca agcgaggaga tcacttgaaa gaacattaag tggtaaagga    960
cccgagaaag aattactagt gactatggaa ctcgataaaa tcaaaactac tatagaaaag   1020
gagcagaaaa tgtctgatga aggaacttac tgggattgtg tgaaagatgg tattaacagg   1080
agaagaacga gaatagcttg tttatgttgg atcggtcaat gctcctgtgg tgcatcatta   1140
attggttatt caacttactt ttatgaaaaa gctggtgtta gcactgatac ggcttttact   1200
ttcagtatta tccaatattg tcttggtatt gctgcaacgt tgtatcctg gtgggcttca    1260 aaatattgtg gcagatttga cctttatgct tttgggctgg cttttcaggc tattatgttc   1320
ttcattatcg gtggtttagg atgttcagac actcatggcg ctaaaatggg tagtggtgct   1380
cttctaatgg ttgtcgcgtt cttttacaac ctcggtattg cacctgttgt tttttgctta   1440
gtgtctgaaa tgccgtcttc aaggctaaga accaaaacaa ttattttggc tcgtaatgct   1500
tacaatgtga tccaagttgt agttacagtt ttgattatgt accaattgaa ctcagagaaa   1560
tggaattggg gtgctaaatc aggcttttc tggggaggat tttgtctggc cactttagct    1620
tgggctgttg tcgatttacc agaaaccgct ggcaggactt ttattgagat aaatgaattg   1680
tttagacttg gtgttccagc aagaaagttc aagtcgacta agtcgaccc ttttgcagct    1740 gccaaagcag cagctgcaga aattaatgtt aaagatccga aggaagattt ggaaacttct   1800
gtggtagatg aagggcgaaa cacctcatct gttgtgaaca atga                    1845
```

<210> SEQ ID NO 52
<211> LENGTH: 14
<212> TYPE: PRT
<213> ORGANISM: Saccharomyces cerevisiae

<400> SEQUENCE: 52

Gln Gly Lys Lys Ser Asp Phe Gly Leu Ser His His Glu Tyr
1               5                   10

<210> SEQ ID NO 53
<211> LENGTH: 14
<212> TYPE: PRT
<213> ORGANISM: Saccharomyces cerevisiae

<400> SEQUENCE: 53

Gln Gly Lys Lys Ser Asp Phe Gly Leu Ser His Leu Glu Tyr
1               5                   10

<210> SEQ ID NO 54
<211> LENGTH: 14
<212> TYPE: PRT
<213> ORGANISM: Saccharomyces cerevisiae

<400> SEQUENCE: 54

Gln Gly Lys Lys Ser Asp Phe Gly Leu Ser His His Glu Tyr
1               5                   10

<210> SEQ ID NO 55
<211> LENGTH: 14
<212> TYPE: PRT
<213> ORGANISM: Saccharomyces cerevisiae

<400> SEQUENCE: 55

Gly Lys Lys Asp Ser Ala Phe Glu Leu Asp His Leu Lys Phe
1               5                   10

```
<210> SEQ ID NO 56
<211> LENGTH: 14
<212> TYPE: PRT
<213> ORGANISM: Saccharomyces cerevisiae

<400> SEQUENCE: 56

Gly Lys Lys Asp Ser Ala Phe Glu Leu Asp His Leu Gly Phe
1               5                   10

<210> SEQ ID NO 57
<211> LENGTH: 14
<212> TYPE: PRT
<213> ORGANISM: Saccharomyces cerevisiae

<400> SEQUENCE: 57

Gln Gly Lys Lys Ser Asp Phe Gly Leu Ser His His Glu Tyr
1               5                   10

<210> SEQ ID NO 58
<211> LENGTH: 14
<212> TYPE: PRT
<213> ORGANISM: Saccharomyces cerevisiae

<400> SEQUENCE: 58

Gln Gly Lys Lys Ser Asp Phe Gly Leu Ser His His Glu Tyr
1               5                   10

<210> SEQ ID NO 59
<211> LENGTH: 14
<212> TYPE: PRT
<213> ORGANISM: Saccharomyces cerevisiae

<400> SEQUENCE: 59

Gln Gly Lys Lys Ser Asp Phe Asp Leu Ser His Leu Val Tyr
1               5                   10

<210> SEQ ID NO 60
<211> LENGTH: 14
<212> TYPE: PRT
<213> ORGANISM: Saccharomyces cerevisiae

<400> SEQUENCE: 60

Gln Gly Lys Lys Ser Asp Phe Asp Leu Pro His Leu Glu Tyr
1               5                   10

<210> SEQ ID NO 61
<211> LENGTH: 14
<212> TYPE: PRT
<213> ORGANISM: Saccharomyces cerevisiae

<400> SEQUENCE: 61

Gln Gly Lys Lys Ser Asp Phe Asp Leu Ser Pro Leu Glu Tyr
1               5                   10

<210> SEQ ID NO 62
<211> LENGTH: 14
<212> TYPE: PRT
<213> ORGANISM: Saccharomyces cerevisiae

<400> SEQUENCE: 62

Gln Gly Lys Lys Ser Asp Phe Asp Leu Ser His Pro Glu Tyr
1               5                   10

<210> SEQ ID NO 63
```

```
<211> LENGTH: 14
<212> TYPE: PRT
<213> ORGANISM: Saccharomyces cerevisiae

<400> SEQUENCE: 63

Gln Gly Lys Lys Ser Asp Phe Asp Leu Ser His Leu Lys Tyr
1               5                   10

<210> SEQ ID NO 64
<211> LENGTH: 14
<212> TYPE: PRT
<213> ORGANISM: Saccharomyces cerevisiae

<400> SEQUENCE: 64

Gln Gly Lys Lys Ser Asp Phe Asp Leu Ser His Phe Lys Tyr
1               5                   10

<210> SEQ ID NO 65
<211> LENGTH: 14
<212> TYPE: PRT
<213> ORGANISM: Saccharomyces cerevisiae

<400> SEQUENCE: 65

Gln Gly Lys Lys Ser Asp Phe Asp Leu Ser Arg Leu Glu Tyr
1               5                   10

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gtctttccca tcatgagtac ggtccc                                          26
```

GLUCOSE-INDUCED INACTIVATION/DEGRADATION-RESISTANT TRANSPORTER GENE AND USE THEREOF

TECHNICAL FIELD

The present invention relates to a glucose-induced inactivation/degradation transporter gene and use thereof, and more particularly, to a brewing yeast having excellent assimilation of oligosaccharides (maltose, maltotriose, etc.), an alcoholic beverage prepared using the yeast, a method of producing the alcoholic beverage, and so on.

BACKGROUND ART

In the production of malt fermented beverages such as beer, happoshu (low-malt beer), whisky, etc., the major three sugars contained in a wort prepared by mashing a malt, etc. are glucose, maltose and maltotriose. The ratio of these malt-derived sugars can be somewhat varied depending on the mashing process and may be approximately 1:5:1, since the ratio does not change significantly when enzyme preparations, glycosylated starch, etc. are not added. Among them, glucose is a monosaccharide and preferentially assimilated as a sugar most favored by yeast.

Yeast has numerous genes suppressed in the presence of glucose during the transcription process. This suppressing control mechanism is called glucose repression. Several transporters required for uptake of maltose or maltotriose into yeast all undergo this repression. It is known that some of these gene products which undergo such glucose repression are inactivated in the presence of glucose even after translation. α-Glucoside transporters are also within this type and known to be rapidly degraded in the presence of glucose. The first step of assimilation of maltose or maltotriose is its uptake into yeast cells by these transporters and when transporters are degraded, assimilation of these sugars is discontinued. This is the reason why the expression of transporter is called a rate-determining step for assimilation.

Non-Patent Literature 1: Brondijk, T. H., van der Rest, M. E., Pluim, D., de Vries, Y. de., Stingl, K., Poolman, B., and Konings, W. N. (1998) J. Biol. Chem., 273 (25), 15352-15357
Non-Patent Literature 2: Medintz, I., Wang, X., Hradek, T., and Michels, C. A. (2000) Biochemistry, 39 (15), 4518-4526
Non-Patent Literature 3: Gadura, N., and Michels, C. A. (2006) Curr. Genet., 50 (2), 101-114

DISCLOSURE OF INVENTION

Under such situations, it has been desired to provide a yeast bearing an oligosaccharide transporter less susceptible to glucose-induced inactivation or degradation and having an improved assimilation of oligosaccharides such as maltose, etc.

The present inventors have made extensive efforts to solve the foregoing problems. As a result, the inventors have developed a novel method of screening a transporter, which is less susceptible to glucose-induced inactivation or degradation (hereinafter referred to as "glucose-induced inactivation/degradation-resistant transporter") or a yeast bearing the transporter, and based on the screening method, found the glucose-induced inactivation/degradation-resistant transporter or a yeast bearing the same. The present invention has thus been accomplished.

That is, the present invention relates to a gene encoding the glucose-induced inactivation/degradation-resistant transporter, a transporter protein encoded by the gene, a transformed yeast in which expression of the gene is regulated, a method of producing an alcoholic beverage which comprises using the yeast in which expression of the gene is regulated, etc. More specifically, the present invention provides the polynucleotides given below, vectors comprising the polynucleotides, transformed yeasts in which the vectors are introduced, and a method of producing alcoholic beverages using these transformed yeasts, etc.

(1) A polynucleotide encoding a transporter protein comprising a mutated sequence with a mutation in the amino acid sequence of SEQ ID NO: 4, 6, 8 or 10, and having a resistance to glucose-induced inactivation/degradation, wherein:

the mutation of deletion, substitution, insertion and/or addition of 1 to 5 amino acids is introduced into the sequence of amino acids 39 to 52 (QGKKSDFDLSHLEY) of SEQ ID NO: 4 or 6, into the sequence of amino acids 39 to 52 (QGKKSDFDLSHHEY) of SEQ ID NO: 8, or into the sequence of amino acids 44 to 57 (GKKDSAFELDHLEF) of SEQ ID NO: 10.

(2) The polynucleotide according to (1), encoding a transporter comprising a mutated sequence with a further mutation of deletion, substitution, insertion and/or addition of 1 to 15 amino acids introduced into a sequence fragment other than the sequence of amino acids 39 to 52 or 44 to 57.

(3) The polynucleotide according to (1) or (2), wherein a mutation of deletion, substitution, insertion and/or addition of 1 to 5 amino acids is introduced into the sequence of amino acids 46 to 51 (DLSHLE) of SEQ ID NO: 4 or 6, into the sequence of amino acids 46 to 51 (DLSHHE) of SEQ ID NO: 8, or into the sequence of amino acids 51 to 56 (ELDHLE) of SEQ ID NO: 10.

(4) A polynucleotide comprising a polynucleotide consisting of the nucleotide sequence of SEQ ID NO: 25, 27, 29, 31, 33, 35, 37, 39, 41, 43, 45, 47 or 49.

(5) A polynucleotide comprising a polynucleotide consisting of the nucleotide sequence of SEQ ID NO: 29, 33, 35, 39, 41, 43 or 47.

(6) A polynucleotide comprising a polynucleotide encoding a protein consisting of the amino acid sequence of SEQ ID NO: 26, 28, 30, 32, 34, 36, 38, 40, 42, 44, 46, 48 or 50.

(7) A polynucleotide comprising a polynucleotide encoding a protein consisting of the amino acid sequence of SEQ ID NO: 30, 34, 36, 40, 42, 44 or 48.

(8) The polynucleotide according to any one of (1) to (7), which is a DNA.

(9) A protein encoded by the polynucleotide according to any one of (1) to (8).

(10) A vector comprising the polynucleotide according to any one of (1) to (8).

(11) A transformed yeast introduced with the vector according to (10).

(12) The yeast for brewing according to (11), wherein oligosaccharide assimilation capability is improved by introducing the vector according to (10).

(13) The yeast for brewing according to (12), wherein oligosaccharide assimilation capability is improved by increasing the expression level of the protein according to (9).

(14) A method of producing a beverage which comprises using the yeast according to any one of (11) to (13).

(15) The method of producing a beverage according to (14), wherein the beverage to be brewed is a malt beverage.

(16) The method of producing a beverage according to (14), wherein the beverage to be brewed is wine.

(17) A beverage produced by the method according to any one of (14) to (16).

(18) A method of obtaining a yeast bearing a transporter having a resistance to glucose-induced inactivation/degradation, which comprises:

(1) a step of culturing a plurality of test yeasts in an oligosaccharide medium containing 2-deoxyglucose and selecting a yeast bearing the transporter protein less susceptible to glucose-induced inactivation or degradation using the growth level of each yeast as an indicator;

(2) a step of identifying the amino acid residues or amino acid sequence contributing to less susceptibility to glucose-induced inactivation or degradation by comparing the amino acid sequence of a transporter protein contained in the yeast selected in the step (1) with the amino acid sequence of a transporter protein which level of glucose-induced inactivation or degradation is known;

(3) a step of designing a polynucleotide encoding a transporter protein having a resistance to glucose-induced inactivation/degradation based on the amino acid sequence information obtained in the step (2); and, (4) introducing the polynucleotide designed in the step (3) into a yeast, culturing the yeast in an oligosaccharide medium and measuring the resistance to glucose-induced inactivation/degradation of the transporter protein contained in the yeast, the oligosaccharide assimilation capability, growth rate and/or fermentation rate in a wort of the yeast.

(18a) The method according to (18), wherein a plurality of test yeasts in the step (1) above are naturally occurring yeasts or yeasts mutated from naturally occurring yeasts.

(18b) The method according to (18), wherein the yeast into which the polynucleotide designed in the step (3) is introduced in the step (4) includes mutant Mal31p protein wherein a site-directed mutation is introduced into the amino acid sequence of Mal31p protein, mutant Mal16p protein wherein a site-directed mutation is introduced into the amino acid sequence of Mal61p protein, mutant Mtt1p protein wherein a site-directed mutation is introduced into the amino acid sequence of Mtt1p protein or mutant Agt1p protein wherein a site-directed mutation is introduced into the amino acid sequence of Agt1p protein.

The use of the yeast in accordance with the present invention provides the advantage that the fermentation rate of moromi mash containing oligosaccharides such as maltose, maltotriose, etc. can be increased. The transporter gene in accordance with the present invention can be introduced into any of brewing yeasts or laboratory yeasts. It is effective especially in the case where oligosaccharides (maltose, maltotriose, turanose, trehalose, etc.) which can be taken up by the transporter gene in accordance with the present invention are contained in a crude fermentation liquor abundant in monosaccharides such as glucose, fructose, etc.

BRIEF DESCRIPTION OF DRAWINGS

FIG. 1 shows the differences in growth between laboratory yeasts in the presence of 2-deoxyglucose.

FIG. 2 shows the nucleotide sequence of MAL21 gene (SEQ ID NO: 51).

FIG. 3 shows the amino acid sequence of Mal21p gene (SEQ ID NO: 2).

FIG. 4 shows the degradation rates of Mal21p, Mal31p and Mal61p in the presence of glucose.

FIG. 5 shows the degradation rate of mutant Mal31p in the presence of glucose.

FIG. 6 shows the alignment of Mal21/Mal31/Mal61/Mtt1/Agt1. Figure discloses residues 1-392 of SEQ ID NOS: 2, 4, and 6, residues 1-393 of SEQ ID NO: 8, and residues 1-398 of SEQ ID NO: 10, respectively, in order of appearance.

FIG. 7 shows the alignment of Mal21/Mal31/Mal61/Mtt1/Agt1 (continued from FIG. 6), Figure discloses residues 393-614 of SEQ ID NOS: 2, 4, and 6, residues 394-615 of SEQ ID NO: 8, and residues 399-616 of SEQ ID NO: 10, respectively, in order of appearance.

FIG. 8 shows the degradation rate of mutant Agt1p in the presence of glucose.

FIG. 9 shows the differences in growth among strains bearing mutant MAL61 gene in the presence of 2-deoxyglucose (identification of amino acid residues which greatly affect the degradation rate).

FIG. 10 shows the degradation rate of mutant Mal61p in the presence of glucose (identification of amino acid residues which greatly affect the degradation rate).

FIG. 11 shows the differences in growth among strains bearing native MTT1 and mutant MTT1 gene in the presence of 2-deoxyglucose.

FIG. 12 shows the growth of MAL21 gene-highly expressed laboratory strains in a maltose medium.

FIG. 13 shows the maltose fermentation rates of MAL21 gene-highly expressed bottom-fermenting beer yeast strains in happoshu (low-malt beer) or in happoshu (glucose-rich) wort.

FIG. 14 shows the maltose fermentation rates in the wort of top-fermenting beer yeasts in which the transporter less susceptible to glucose-induced degradation is highly expressed.

FIG. 15 shows the construction of plasmid pJHXSB.
FIG. 16 shows the construction of plasmid pJHIXSB.
FIG. 17 shows the construction of plasmid pYCGPY.
FIG. 18 shows the construction of plasmid pUP3GLP.
FIG. 19 shows the construction of plasmid pYCp49H.

BEST MODES FOR CARRYING OUT THE INVENTION

Based on the idea that if glucose-induced inactivation or degradation of a post-translational transporter can be regulated, maltose and maltotriose can be more efficiently assimilated into a yeast in the presence of glucose, the present inventors have made extensive efforts and as a result, found Mal21p from the natural world, which is an α-glucoside transporter less susceptible to degradation, and confirmed that the degradation rate of Mal21p is extremely slow when compared to other transporters.

Furthermore, the inventors have introduced a mutation into the transporter gene using UV and succeeded in screening of the transporter having the resistance to glucose-induced inactivation or degradation in a unique way. More specifically, the inventors have imparted mutation to Mal31p and Agt1p, which are α-glucoside transporters susceptible to glucose-induced inactivation or degradation thereby to obtain several transporters less susceptible to the degradation. The inventors have also identified the amino acid residues contributing to less susceptibility to the degradation from the amino acid sequences of these mutant transporters and the amino acid sequence of Mal21p. As a result, the inventors have succeeded in modifying Mtt1p, which is a novel α-glucoside transporter possessed by bottom-fermenting beer yeasts, into a transporter less susceptible to glucose-induced inactivation or degradation, by replacing amino acids based on the information. The inventors have also succeeded in increasing the growth rate actually in a maltose medium, by highly expressing the transporter less susceptible to glucose-induced inactivation or degradation, which has discovered or newly obtained. In addition, the assimilation rate of maltose could be increased in beer brewing. The present invention has thus been accomplished as a result of such an idea and research achievements.

The genes obtained in the present invention and their nucleotide sequences, the transporter proteins encoded by these genes or their amino acid sequences are given below.

[SEQ ID NO: 1] Nucleotide sequence of MAL21
[SEQ ID NO: 2] Amino acid sequence of Mal21p α-glucoside transporter
[SEQ ID NO: 3] Nucleotide sequence of MAL31
[SEQ ID NO: 4] Amino acid sequence of Mal31p α-glucoside transporter
[SEQ ID NO: 5] Nucleotide sequence of MAL61
[SEQ ID NO: 6] Amino acid sequence of Mal61α-glucoside transporter
[SEQ ID NO: 7] Nucleotide sequence of MTT1
[SEQ ID NO: 8] Amino acid sequence of Mtt1p α-glucoside transporter
[SEQ ID NO: 9] Nucleotide sequence of AGT1
[SEQ ID NO: 10] Amino acid sequence of Agt1p α-glucoside transporter
[SEQ ID NO: 25] Nucleotide sequence of MAL61[D46G]
[SEQ ID NO: 26] Amino acid sequence of Mal61p[Gly46]
[SEQ ID NO: 27] Nucleotide sequence of MAL61[L50H]
[SEQ ID NO: 28] Amino acid sequence of Mal61p[His50]
[SEQ ID NO: 29] Nucleotide sequence of MAL61[D46G, L50H]
[SEQ ID NO: 30] Amino acid sequence of Mal61p[Gly46, His50]
[SEQ ID NO: 31] Nucleotide sequence of AGT1[E56K]
[SEQ ID NO: 32] Amino acid sequence of Agt1p [Lys56]
[SEQ ID NO: 33] Nucleotide sequence of AGT1[E56G]
[SEQ ID NO: 34] Amino acid sequence of Agt1p [Gly56]
[SEQ ID NO: 35] Nucleotide sequence of MTT1[D46G]
[SEQ ID NO: 36] Amino acid sequence of Mtt1p[Gly46]
[SEQ ID NO: 37] Nucleotide sequence of MAL31[E51V]
[SEQ ID NO: 38] Amino acid sequence of Mal31p[Val51]
[SEQ ID NO: 39] Nucleotide sequence of MAL31[S48P]
[SEQ ID NO: 40] Amino acid sequence of Mal31p[Pro48]
[SEQ ID NO: 41] Nucleotide sequence of MAL31[H49P]
[SEQ ID NO: 42] Amino acid sequence of Mal31p[Pro49]
[SEQ ID NO: 43] Nucleotide sequence of MAL31[L50P]
[SEQ ID NO: 44] Amino acid sequence of Mal31p[Pro50]
[SEQ ID NO: 45] Nucleotide sequence of MAL31[E51K]
[SEQ ID NO: 46] Amino acid sequence of Mal31p[Lys51]
[SEQ ID NO: 47] Nucleotide sequence of MAL31[L50F, E51K]
[SEQ ID NO: 48] Amino acid sequence of Mal31p[Phe50, Lys51]
[SEQ ID NO: 49] Nucleotide sequence of MAL31[H49R]
[SEQ ID NO: 50] Amino acid sequence of Mal31p[Arg49]

As used herein, the term "α-glucoside transporter" refers to a protein associated with α-glucoside transmembrane transport and such α-glucoside transporters include a maltose transporter, a maltotriose transporter, etc.

1. Polynucleotide of the Invention

First, the present invention provides the polynucleotide encoding a transporter protein comprising a mutated sequence with a mutation in the amino acid sequence of SEQ ID NO: 4, 6, 8 or 10, and having the resistance to glucose-induced inactivation/degradation, wherein the mutation of deletion, substitution, insertion and/or addition of 1 to 5 amino acids (preferably, 1 to 4, 1 to 3, 1 to 2, or 1) is introduced into the sequence of amino acids 39 to 52 (QGKKSDFDLSHLEY) of SEQ ID NO: 4 or 6, into the sequence of amino acids 39 to 52 (QGKKSDFDLSHHEY) of SEQ ID NO: 8, or into the sequence of amino acids 44 to 57 (GKKD-SAFELDHLEF) of SEQ ID NO: 10 (specifically a DNA, hereinafter sometimes briefly referred to as "DNA"). The present invention also includes the transporter proteins described above comprising a mutated sequence wherein the mutation of deletion, substitution, insertion and/or addition of 1 to 15 amino acids (preferably, 1 to 14, 1 to 13, 1 to 12, 1 to 11, 1 to 10, 1 to 9, 1 to 8, 1 to 7, 1 to 6, 1 to 5, 1 to 4, 1 to 3, 1 to 2, or 1) is further introduced into sequence fragments other than the sequence of amino acids 39 to 52 or 44 to 57 in the amino acid sequences described above.

The protein preferred in the present invention also includes the transporter proteins described above, in which the mutation of deletion, substitution, insertion and/or addition of 1 to 5 amino acids (preferably, 1 to 4, 1 to 3, 1 to 2, or 1) is introduced into the sequence of amino acids 46 to 51 (DLSHLE) of SEQ ID NO: 4 or 6, into the sequence of amino acids 46 to 51 (DLSHHE) of SEQ ID NO: 8, or into the sequence of amino acids 51 to 56 (ELDHLE) of SEQ ID NO: 10. The transporter protein preferred in the present invention includes a protein consisting of the amino acid sequence shown by SEQ ID NO: 26, 28, 30, 32, 34, 36, 38, 40, 42, 44, 46, 48 or 50, more preferably a protein consisting of the amino acid sequence shown by SEQ ID NO: 30, 34, 36, 40, 42, 44 or 48.

The transporter protein of the present invention includes a transporter protein consisting of the amino acid sequence of SEQ ID NO: 26, 28, 30, 32, 34, 36, 38, 40, 42, 44, 46, 48 or 50, in which, for example, 1 to 15, 1 to 10, 1 to 9, 1 to 8, 1 to 7, 1 to 6 (1 to several), 1 to 5, 1 to 4, 1 to 3, 1 to 2, or 1 amino acid is deleted, substituted, inserted and/or added in the amino acid sequence, and having the resistance to glucose-induced inactivation/degradation. In general, a smaller number of the deletion, substitution, insertion and/or addition in the amino acid residues described above is more preferable.

Such proteins include transporter proteins having the amino acid sequence having an identity of at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8% and at least about 99.9%, with the amino acid sequence of SEQ ID NO: 26, 28, 30, 32, 34, 36, 38, 40, 42, 44, 46, 48 or 50, and having the resistance to glucose-induced inactivation/degradation. In general, the numerical value of the identity described above is more preferable as the number is larger.

<Evaluation of the Resistance to Glucose-Induced Inactivation/Degradation>

According to the present invention, the resistance to glucose-induced inactivation/degradation can be evaluated, for example, by the following procedures. First, it is confirmed that a strain expressing each transporter protein is able to grow in a 0 to 2 mM 2-deoxyglucose-containing maltose, etc. minimum medium (6.7 g/L of yeast nitrogen base w/o amino acids, 20 g/L of maltose, etc.; also containing the required nutrients if the transformant is auxotrophic) or in a 0 to 8.0 mM 2-deoxyglucose-containing maltose-supplemented synthetic complete medium (SCM) (6.7 g/L of yeast nitrogen base w/o amino acids, 20 g/L of maltose, 20 mg/ml of adenine sulfate, 20 mg/ml of uracil, 20 mg/ml of L-tryptophan, 20 mg/ml of L-histidine hydrochloride, 20 mg/ml of L-arginine hydrochloride, 20 mg/ml of L-methionine, 30 mg/ml of L-tyrosine, 30 mg/ml of L-leucine, 30 mg/ml of L-isoleucine, 30 mg/ml of L-lysine hydrochloride, 50 mg/ml of L-phenylalanine, 100 mg/ml of L-glutamic acid, 100 mg/ml of L-aspartic acid, 150 mg/ml of L-valine, 200 mg/ml of L-threonine and 400 mg/ml of L-serine), to select the strain in which the transporter retains the maltose uptake activity in yeasts even where the signal of glucose-induced inactivation/degradation generates. Next, this strain is inoculated into YPD (10 g/L of yeast extract, 20 g/L of polypeptone and 20 g/L of glucose) followed by shaking the culture at 30° C. overnight. The culture broth is inoculated into a YPM medium (10 g/L of yeast extract, 20 g/L of polypeptone and 5 g/L of maltose) to reach OD660=1.0 followed by shaking the culture at 30° C. for 2.5 hours. The cells are then collected. 60 OD660 units of cells are weighed and suspended in 30 ml of a medium for degradation rate measurement (1.7 g/L of yeast nitrogen base w/o amino acids and ammonia, 20 g/L of glucose and 25 µg/L of cycloheximide) preincubated at 30° C., followed by incubation at 30° C. The cell suspension is monitored by means of 5 ml sampling for an appropriate time period (0, 10, 20, 30 and 40 minutes or 0, 30, 60, 90 and 120 minutes). After the suspension is centrifuged immediately thereafter, the supernatant is discarded and the cells are frozen using an ethanol-dry ice. The transporter protein is detected from the frozen cells in a conventional manner and the intensity of the protein band is measured to determine the half life from its diminution rate. The transporter protein prefered in the present invention has the half life of 2 times or more, 3 times or more, 4 times or more, 5 times or more, 6 times or more or 8 times or more, than that of, e.g., Mal31p.

The present invention further encompasses polynucleotides comprising a polynucleotide which hybridizes, under stringent conditions, to the polynucleotide of the present invention including the polynucleotide encoding the transporter protein comprising a mutated sequence with a mutation in the amino acid sequence of SEQ ID NO: 4, 6, 8 or 10, and having the resistance to glucose-induced inactivation/degradation, wherein the mutation of deletion, substitution, insertion and/or addition of 1 to 5 amino acids (preferably, 1 to 4, 1 to 3, 1 to 2 or 1) is introduced into the sequence of amino acids 39 to 52 (QGKKSDFDLSHLEY) of SEQ ID NO: 4 or 6, into the sequence of amino acids 39 to 52 (QGKKSDFDLSHHEY) of SEQ ID NO: 8, or into the sequence of amino acids 44 to 57 (GKKDSAFELDHLEF) of SEQ ID NO: 10, or the like, and which encodes a transporter protein having the resistance to glucose-induced inactivation/degradation.

Preferred examples of the polynucleotide in the present invention are those polynucleotides as defined above, specifically the polynucleotide comprising the polynucleotide comprising the nucleotide sequence of SEQ ID NO: 25, 27, 29, 31, 33, 35, 37, 39, 41, 43, 45, 47 or 49, and more preferably the polynucleotide comprising the polynucleotide comprising the nucleotide sequence of SEQ ID NO: 29, 33, 35, 39, 41, 43 or 47. In EXAMPLES later described, it has been demonstrated that the sequence of amino acids 46 to 51 in SEQ ID NO: 4, 6 or 8 is associated with the resistance to glucose-induced inactivation/degradation of Mal21p, mutant Mal31p, mutant Mal61p and mutant Mtt1p, and the sequence of amino acids 51 to 56 in SEQ ID NO: 10 is associated with the resistance of Agt1. It is therefore desired to consider this sequence information when the mutation is introduced.

As used herein, the term "polynucleotide (DNA) which hybridizes under stringent conditions" refers to a DNA consisting of a nucleotide sequence complementary to the nucleotide sequence of SEQ ID NO: 25, 27, 29, 31, 33, 35, 37, 39, 41, 43, 45, 47 or 49, or a DNA obtained by the colony hybridization technique, the plaque hybridization technique, the Southern hybridization technique or the like, using as a probe all or a part of a DNA encoding the amino acid sequence of SEQ ID NO: 26, 28, 30, 32, 34, 36, 38, 40, 42, 44, 46, 48 or 50. For the hybridization, there may be used methods described in, for example, Molecular Cloning, 3rd Ed., Current Protocols in Molecular Biology, John Wiley & Sons 1987-1997, etc.

As used herein, the term "stringent conditions" may be any of low stringent conditions, medium stringent conditions and high stringent conditions. The term "low stringent conditions" refers to conditions of, e.g., 5×SSC, 5×Denhardt's solution, 0.5% SDS, 50% formamide and 32° C. The term "medium stringent conditions" refers to conditions of, e.g., 5×SSC, 5×Denhardt's solution, 0.5% SDS, 50% formamide and 42° C. The term "high stringent conditions" refers to conditions of, e.g., 5×SSC, 5×Denhardt's solution, 0.5% SDS, 50% formamide and 50° C. It can be expected under these conditions that DNAs having a higher homology can be efficiently obtained as the temperature becomes higher. However, there are several factors that might affect the stringency of hybridization to be considered and such factors include temperature, probe concentration, probe length, ionic strength, time, salt concentration, etc. Those skilled in the art can suitably choose these factors to achieve the same stringencies.

In the case of using commercially available kits for the hybridization, for example, Alkphos Direct Labeling Reagents (manufactured by Amersham Pharmacia) can be used. In this case, the hybridized DNA can be detected by incubating with a labeled probe overnight and washing the membrane with a primary wash buffer containing 0.1% (w/v) SDS at 55° C., according to the protocol attached to the kit.

Other DNAs that can be hybridized include DNAs having an identity of at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, or at least about 99.9%, with the DNA encoding the amino acid sequence of SEQ ID NO: 26, 28, 30, 32, 34, 36, 38, 40, 42, 44, 46, 48 or 50, as calculated by a homology search software such as FASTA, BLAST, etc. using default parameters.

The identity of amino acid sequences or nucleotide sequences can be determined using the algorithm BLAST by Karlin and Altschul (Proc. Natl. Acad. Sci. USA, 87: 2264-2268, 1990; Proc. Natl. Acad. Sci. USA, 90: 5873, 1993). Based on the algorithm BLAST, programs called BLASTN or BLASTX have been developed (Altschul S. F. et al., J. Mol. Biol. 215: 403, 1990). When a nucleotide sequence is analyzed using BLASTN, the parameters are set to, for example, score=100 and word length=12. When an amino acid sequence is analyzed using BLASTX, the parameters are set to, for example, score=50 and word length=3. When BLAST and Gapped BLAST programs are used, default parameters for each of the programs are employed.

2. Protein of the Invention

The present invention further provides the protein encoded by any one of the polynucleotides described above. Preferred examples of the proteins in the present invention are transporter proteins comprising the amino acid sequence of SEQ ID NO: 4, 6, 8 or 10, in which 1 to 15 amino acids (preferably, 1 to 14, 1 to 13, 1 to 12, 1 to 11, 1 to 10, 1 to 9, 1 to 8, 1 to 7, 1 to 6, 1 to 5, 1 to 4, 1 to 3, 1 to 2, or 1) are deleted, substituted, inserted and/or added in the amino acid sequence, and having the resistance to glucose-induced inactivation/degradation.

Such proteins include transporter proteins comprising the amino acid sequence of SEQ ID NO: 4, 6, 8 or 10, in which the aforesaid number of amino acid residues are deleted, substituted, inserted and/or added in the amino acid sequence, and having the resistance to glucose-induced inactivation/degradation.

Such transporter proteins preferably include proteins consisting of the amino acid sequence of SEQ ID NO: 26, 28, 30, 32, 34, 36, 38, 40, 42, 44, 46, 48 or 50, and more preferably, proteins consisting of the amino acid sequence of SEQ ID NO: 30, 34, 36, 40, 42, 44 or 48. Such proteins include transporter proteins having the amino acid sequence which has the homology described above to the amino acid sequence of SEQ ID NO: 26, 28, 30, 32, 34, 36, 38, 40, 42, 44, 46, 48 or 50, and having the resistance to glucose-induced inactivation/degradation. These proteins can be obtained by site-directed mutagenesis described in Molecular Cloning, 3rd Ed., Current Protocols in Molecular Biology, Nuc. Acids. Res., 10, 6487 (1982), Proc. Natl. Acad. Sci. USA, 79, 6409 (1982), Gene, 34, 315 (1985), Nuc. Acids. Res., 13, 4431 (1985), Proc. Natl. Acad. Sci. USA, 82, 488 (1985), etc.

The deletion, substitution, insertion and/or addition of 1 to 15 amino acid residues (preferably, 1 to 14, 1 to 13, 1 to 12, 1 to 11, 1 to 10, 1 to 9, 1 to 8, 1 to 7, 1 to 6, 1 to 5, 1 to 4, 1 to 3, 1 to 2, or 1) in the amino acid sequence of the protein of the present invention is intended to mean that 1 to 15 amino acid residues (preferably, 1 to 14, 1 to 13, 1 to 12, 1 to 11, 1 to 10, 1 to 9, 1 to 8, 1 to 7, 1 to 6, 1 to 5, 1 to 4, 1 to 3, 1 to 2, or 1) are deleted, substituted, inserted and/or added at optional positions of the 1 to 15 amino acid sequence in the same sequence, in which two or more deletions, substitutions, insertions and/or additions may also take place simultaneously.

Examples of the amino acid residues which are mutually substitutable are given below. The amino acid residues in the same group are mutually substitutable. Group A: leucine, isoleucine, norleucine, valine, norvaline, alanine, 2-aminobutanoic acid, methionine, o-methylserine, t-butylglycine, t-butylalanine and cyclohexylalanine; Group B: aspartic acid, glutamic acid, isoaspartic acid, isoglutamic acid, 2-aminoadipic acid and 2-aminosuberic acid; Group C: asparagine and glutamine; Group D: lysine, arginine, ornithine, 2,4-diaminobutanoic acid and 2,3-diaminopropionic acid; Group E: proline, 3-hydroxyproline and 4-hydroxyproline; Group F: serine, threonine and homoserine; and Group G: phenylalanine and tyrosine.

The protein of the present invention can also be produced by chemical synthesis methods such as the Fmoc method (fluorenylmethyloxycarbonyl method), the tBoc method (t-butyloxycarbonyl method) or the like. In addition, peptide synthesizers available from, for example, Advanced ChemTech, Perkin-Elmer, Pharmacia, Protein Technology Instrument, Synthecell-Vega, PerSeptive, Shimadzu Corp. can also be used for chemical synthesis.

3. Vector of the Invention and Yeast Transformed with the Vector

Next, the present invention provides a vector comprising the polynucleotide described above. The vector of the present invention comprises any of the polynucleotides (DNAs) described above. Generally, the vector of the present invention is constructed to contain an expression cassette comprising as components (x) a promoter that is transcribable in a yeast cell; (y) a polynucleotide (DNA) in any of those described above that is linked to the promoter in either sense or antisense direction and (z) a signal that functions in a yeast in terms of transcription termination and polyadenylation of RNA molecule. In expressing the aforesaid protein of the present invention at a high level, it is preferred to introduce these polynucleotides in a sense direction to the promoter in order to promote the expression of the polynucleotide (DNA) described herein.

As the vector used to introduce the genes to yeasts, any of multicopy (YEp type), single-copy (YCp type) and chromosomal integration (YIp type) plasmids can be utilized. For example, YEp24 (J. R. Broach et al., Experimental Manipulation of Gene Expression, Academic Press, New York, 83, 1983) is known as the YEp type vector; YCp50 (M. D. Rose et al., gene, 60, 237, 1987) is known as the YCp type vector; and YIp5 (K. Struhl, et al., Proc. Natl. Acad. Sci. USP, 76, 1035, 1979) is known as the YIp type vector, all of which are readily available. It is also possible to use plasmids such as chromosomal integration type pUP3GLP (Omura, F. et al., FEMS Microbiol. Lett., 194, 207, 2001) (FIG. 18) or pJHIXSB (FIG. 16), single-copy replicating type pYCGPY (Kodama, Y. et al., Appl. Environ. Microbiol., 67, 3455, 2001) (FIG. 17) or pJHXSB (FIG. 15), etc.

Promoters/terminators for regulating gene expression in yeasts may be used in any optional combination as far as they function in brewing yeasts and are independent from concentrations of the components such as sugar or amino acids in a moromi mash. For example, a promoter for glyceraldehyde-3-phosphate dehydrogenase gene (TDH3), a promoter for phosphoglycerate kinase gene (PGK1), etc. can be used. These genes are already cloned and described in, e.g., M. F. Tuite, et al., EMBO J., 1, 603 (1982), and easily available by known methods. The promoters used in the expression vector can be effectively replaced to those having a suitable transcription activity depending on the sugar components or sugar concentrations of moromi mash or the combination of a plurality of transporters, etc.

As selection markers for transformation, auxotrophic markers cannot be used for brewer's yeasts; therefore, a geneticin resistance gene (G418r), a copper resistance gene (CUP1) (Marin et al., Proc. Natl. Acad. Sci. USA, 81, 337 1984), a cerulenin resistance gene (fas2m, PDR4) (Junji Inokoshi, et al., Biochemistry, 64, 660, 1992; and Hussain et al., Gene, 101, 149, 1991; respectively) can be used as such markers. The vector constructed as described above is introduced into a host yeast. Examples of the host yeast include any yeast which can be used for brewing, for example, brewing yeasts for beer, wine, sake, etc. Specifically, yeasts belonging to the genus *Saccharomyces* can be used. According to the present invention, a lager beer yeast, for example, *Saccharomyces pastorianus* W34/70, etc., *Saccharomyces carlsbergensis* NCYC453, NCYC456, etc., *Saccharomyces cerevisiae* NBRC1951, NBRC1952, NBRC1953, NBRC1954, etc., may be used. In addition, whisky yeasts such as *Saccharomyces cerevisiae* NCYC90, etc., wine yeasts such as wine yeast Nos. 1, 3, 4, etc. from the Brewing Society of Japan, and sake yeasts such as sake yeast Nos. 7, 9, etc. from the Brewing Society of Japan can also be used but there is no limitation thereto. In the present invention, preferably used are brewing yeasts, e.g., *Saccharomyces pastorianus*.

Chromosomal DNAs used to prepare each transporter gene described herein are not limited to strains such as *Saccharomyces cerevisiae* ATCC 20598, ATCC 96955, etc., but may be prepared from any yeast so long as it is a yeast bearing such genes and belonging to *Saccharomyces cerevisiae*.

For yeast transformation, there may be used publicly known methods generally used. The transformation can be performed by, for example, the electroporation method (Meth. Enzym., 194, 182 (1990)), the spheroplast method (Proc. Natl. Acad. Sci. USA, 75, 1929 (1978)), the lithium acetate method (J. Bacteriology, 153, 163 (1983)), and methods described in Proc. Natl. Acad. Sci. USA, 75, 1929 (1978), Methods in Yeast Genetics, 2000 Edition: A Cold Spring Harbor Laboratory Course Manual, and the like, but is not limited thereto.

The transformants can be selected on a uracil-free agar medium by incorporating a gene complementing a host auxotrophy such as URA3 into an expression plasmid. Alternatively, by incorporating a drug resistance gene, for example, cycloheximide drug resistance gene YAP1 or geneticin resistance gene G418R into the expression plasmid, the transformants can be selected on an agar medium containing cycloheximide (e.g., 0.3 µg/ml) or geneticin (e.g., 300 µg/ml).

More specifically, a host yeast is cultured to an OD600 value of 1 to 6 in a standard yeast nutrition medium (e.g., YEPD medium: Genetic Engineering, Vol. 1, Plenum Press, New York, 117 (1979), etc.). This culture yeast is collected by centrifugation, washed and pre-treated with an alkali metal ion, preferably a lithium ion, at a concentration of approximately 1 to 2 M. After the cells are allowed to stand at about 30° C. for about 60 minutes, it is allowed to stand with a DNA to be introduced (about 1 to 20 µg) at about 30° C. for about further 60 minutes. Polyethylene glycol, preferably polyethylene glycol of about 4,000 daltons, is added to reach the final concentration of about 20% to 50%. After allowing to stand at about 30° C. for about 30 minutes, the cells are heated at about 42° C. for about 5 minutes. Preferably, this cell suspension is washed with a standard yeast nutrition medium, inoculated into a predetermined amount of fresh standard yeast nutrition medium and allowed to stand at about 30° C. for about 60 minutes. Thereafter, it is spreaded onto a standard agar medium supplemented with an antibiotic or the like used as a selection marker to obtain a transformant.

Other general cloning techniques can be found in, for example, Molecular Cloning, 3rd Ed., Methods in Yeast Genetics, A laboratory manual (Cold Spring Harbor Laboratory Press, Cold Spring Harbor, N.Y.), etc.

4. Method of Producing Alcoholic Beverages of the Invention and Alcoholic Beverages Produced by the Method The vector of the present invention described above is introduced into a yeast suitable for brewing a target alcoholic beverage. Using this yeast, the fermentation rate of moromi mash containing oligosaccharides such as maltose, maltotriose, etc. can be increased. The target alcoholic beverages include, for example, but not limited to, beer, wine, whisky, sake and the like. In producing these alcoholic beverages, known techniques can be used except that the brewing yeast obtained in the present invention is used in place of its parent strain. Accordingly, raw materials, manufacturing facilities, manufacturing control, etc. may be exactly the same as those in conventional manner and there is no increase in the cost of producing alcoholic beverages whose fermentation period is shortened. Thus, according to the present invention, alcoholic beverages can be produced using existing facilities without increasing costs.

5. Method of Obtaining the Yeast of the Invention

The method of obtaining the yeast bearing the transporter of the present invention having the resistance to glucose-induced inactivation/degradation comprises the following steps (1) to (4).

[Step (1)]

In Step (1), several test yeasts are first cultured in a maltose medium supplemented with 2-deoxyglucose and using its growth level as an indicator, a yeast bearing a transporter protein less susceptible to inactivation by glucose is selected.

The test yeasts used may be naturally occurring yeasts or those mutated from naturally occurring yeasts. Examples of the test yeast include any yeast which can be used for brewing, such as brewing yeasts for beer, wine, sake, etc. Specifically, yeasts belonging to the genus *Saccharomyces* can be used. According to the present invention, there can be used beer yeasts, for example, *Saccharomyces pastorianus* W34/70, etc., *Saccharomyces carlsbergensis* NCYC453, NCYC456, etc., *Saccharomyces cerevisiae* NBRC1951, NBRC1952, NBRC1953, NBRC1954, etc. In addition, whisky yeasts such as *Saccharomyces cerevisiae* NCYC90, etc., wine yeasts such as wine yeast Nos. 1, 3, 4, etc. from the Brewing Society of Japan, and sake yeasts such as sake yeast Nos. 7, 9, etc. from the Brewing Society of Japan can also be used but there is no limitation thereto. In the present invention, preferably used are brewing yeasts, e.g., *Saccharomyces pastorianus*. The yeasts used in EXAMPLES described later can also be used preferably as the test yeasts.

According to the present invention, yeasts in which site-directed mutagenesis is introduced can be preferably used as the test yeasts.

Site-directed mutagenesis can be performed by any technique well known to those skilled in the art. To introduce site-directed mutation, the following techniques which are non-limiting examples can be used: (1) Oligonucleotide-directed Dual Amber (ODA) method/Takara Biomedicals; (2) LA PCR in vitro mutagenesis/Takara Biomedicals; and (3) ExSite™ PCR-Based Site-Directed Mutagenesis Kit/STRATAGENE. Each technique is briefly explained below.

(1) Oligonucleotide-Directed Dual Amber (ODA) Method/Takara Biomedicals

A target gene is inserted into a plasmid bearing an amber mutation on the kanamycin resistance gene (Km) (e.g., pKF 18k-2/19k-2, etc.). The resulting DNA is converted into a single-stranded DNA by thermal denaturation, followed by simultaneous hybridization with a synthetic oligonucleotide for repairing the amber mutation on Km and with a synthetic oligonucleotide for mutagenesis by which a desired mutation is introduced into the target gene. This DNA is replicated while retaining the introduced mutation to finally select only DNA in which the amber mutation on Km has been completely repaired. Thus, in selected DNA, the desired mutation is introduced into the target gene with high probability.

(2) LA PCR In Vitro Mutagenesis/Takara Biomedicals

A DNA fragment to be mutated is inserted into a multicloning site of any plasmid. PCR (I) is performed using a primer for introducing a desired mutation into a target gene and a primer near the multicloning site. On the other hand, PCR (II) is performed to cover the full length of the inserted DNA fragment by using a primer for eliminating a single site (A) from the multicloning site in the direction opposite to mutagenesis in the targeted gene. The products from PCR (I) and (II) are mixed together and the mixture is subjected to further PCR to amplify the full length of the inserted DNA fragment bearing the introduced mutation. Among the DNA fragments thus obtained, those bearing the desired mutation lose the cloning site (A). Accordingly, when the PCR products are digested with a restriction enzyme (A) and then subcloned using the site (A), theoretically the desired mutation is introduced into all of the products thus recloned.

(3) ExSite™ PCR-Based Site-Directed Mutagenesis Kit/STRATAGENE

A DNA fragment to be mutated is inserted into an appropriate plasmid. The resulting DNA is grown in dam+*Escherichia coli* (which has a DNA methylase activity) and A in the GATC sequence is thus methylated. Using this plasmid as a template, synthetic oligonucleotides for introducing a desired mutation are synthesized in both sense and antisense orientations. These oligonucleotides are used as primers for PCR. After PCR, the resulting DNA fragments are digested with a restriction enzyme DpnI which digests only methylated DNA, to leave only a DNA fragment bearing the desired mutation. This fragment is ligated with T4 DNA ligase into the form of cyclic DNA to collect a plasmid having the desired mutation introduced into a target gene.

In the present invention, for the purposes of identifying residues involved in the glucose-induced degradation resistance of MAL21 transporter or imparting the glucose-induced degradation resistance to MTT1 transporter, the amino acid residue 46 or 50 located at the cytoplasmic region near the N-terminal end of the MAL61 or MTT1 transporter is replaced by glycine or histidine, respectively. In particular, the GAT codon encoding aspartic acid is replaced by the GGT codon encoding glycine, and the CTT codon encoding leucine is replaced by the CAT codon encoding histidine. The mutagenesis treatment can be confirmed by analyzing the nucleotide sequence of the mutated DNA using any technique well known to those skilled in the art.

Any yeast that undergoes the mutation treatment can also be used as the test yeast. Any mutation treatment may be used and includes, for example, physical methods such as ultraviolet irradiation, radiation irradiation, etc., chemical methods including treatments with chemicals such as EMS (ethylmethane sulphonate), N-methyl-N-nitrosoguanidine, etc. (see, e.g., Biochemistry Experiments, edited by Yasuji Oshima, vol. 39, Yeast Molecular Genetic Experiments, pp. 67-75, Japan Scientific Societies Press, etc.).

The test yeasts which are preferably used are test yeasts containing mutant MAL31 or mutant AGT1 protein in which site-directed mutation is introduced into the amino acid sequence of MAL31 or AGT1 protein.

The culture in an oligosaccharide medium (e.g., a maltose medium) can be performed using publicly known methods. Using the yeast growth level in such culture as an indicator, yeasts containing the transporter protein less susceptible to glucose-induced inactivation or degradation are selected.

The introduced transporter gene in transformants (α-glucoside transporter gene-free strain is used as a host) being expressed and functioning can be examined by the ability or inability of growth in, for example, a minimum medium in which 0.5% maltose or maltotriose is used as the only carbon source and 3 mg/L of antimycin is supplemented (6.7 g/L of yeast nitrogen base w/o amino acids, 5 g/L of maltose or maltotriose and 3 mg/L of antimycin). Even a strain where α-glucoside transporter fails to function slightly grows in a minimum medium where maltose or maltotriose is used as the only carbon source. However, when a respiration inhibitor antimycin is added, the strain cannot grow in a minimum medium where maltose or maltotriose is used as the only carbon source. Thus, the function of α-glucoside transporter can be clearly confirmed. For example, one platinum loop of sample strain is taken from a YPD plate (10 g/L or yeast extract, 20 g/L of polypeptone and 20 g/L of glucose) and suspended in 1 ml of sterile water to OD660=0.2. After the cells are collected and resuspended in 1 ml of sterile water, the suspension is further diluted to 10-fold and 100-fold, respectively. Serial dilutions of these cell suspensions are spotted by 3 μl each onto a test medium, followed by culturing at 30° C. for 2 or 3 days. The expression vector is introduced into the strain grown, indicating that the introduced α-glucoside transporter is expressed and functions. Next, the suspension is likewise spotted onto a 0 to 2.0 mM 2-deoxyglucose-containing maltose minimum medium (6.7 g/L of yeast nitrogen base w/o amino acids, 20 g/L of maltose, 0 to 2.0 mM 2-deoxyglucose), or onto a 0 to 8.0 mM 2-deoxyglucose-containing maltose-supplemented synthetic complete medium (SCM) (6.7 g/L of yeast nitrogen base w/o amino acids, 20 g/L of maltose, 20 mg/ml of adenine sulfate, 20 mg/ml of uracil, 20 mg/ml of L-tryptophan, 20 mg/ml of L-histidine hydrochloride, 20 mg/ml of L-arginine hydrochloride, 20 mg/ml of L-methionine, 30 mg/ml of L-tyrosine, 30 mg/ml of L-leucine, 30 mg/ml of L-isoleucine, 30 mg/ml of L-lysine hydrochloride, 50 mg/ml of L-phenylalanine, 100 mg/ml of L-glutamic acid, 100 mg/ml of L-aspartic acid, 150 mg/ml of L-valine, 200 mg/ml of L-threonine and 400 mg/ml of L-serine); then the strain which can grow even in the presence of 2-deoxyglucose is selected. It can be concluded that the strain which grows in the presence of 2-deoxyglucose exhibits the activity through expression of the transporter having the resistance to glucose-induced inactivation/degradation.

[Step (2)]

Next, the amino acid residue or amino acid sequence which contributes to the less susceptibility to glucose-induced inactivation or degradation is identified by comparing the amino acid sequence of the transporter protein contained in the yeast selected in the step (1) to the amino acid sequence of a transporter protein whose level of glucose-induced inactivation is known.

This step involves isolating a gene encoding the transporter protein from the yeast selected in a conventional manner, sequencing a DNA sequence of the gene using conventional methods and translating from the DNA sequence into its amino acid sequence. The amino acid sequence thus identified is compared to the amino acid sequence of a transporter protein whose level of glucose-induced degradation is known. The transporter protein whose level of glucose-induced degradation is known includes, for example, Mal31p, Mal61p, Mtt1p and Agt1p, which are α-glucoside transporters, and their mutant proteins, etc. (see, e.g., YBR298C (MAL31) and YGR289C (AGT1) from the Saccharomyces Genome Database, as well as X17391 (MAL61) and DQ010171 (MTT1) from the GenBank for each nucleotide sequence). Analysis of amino acid sequences was performed on the characteristic of resistance to glucose-induced inactivation/degradation for its presence or absence, based on the technique as given in EXAMPLES described later. As a result, it has been confirmed that the sequence of amino acids 46 to 51 in SEQ ID NO: 2, 4, 6 or 8 is associated with the resistance to glucose-induced inactivation/degradation in Mal21p, Mal31p, Mal61p and Mtt1p, and the sequence of amino acids 51 to 56 in SEQ ID NO: 10 is associated with the resistance in Agt1. Location of the respective amino acids is shown in FIGS. 6 and 7.

[Step (3)]

This step involves designing a polynucleotide encoding the transporter having the resistance to glucose-induced inactivation/degradation based on the amino acid sequence information obtained in the step (2). As described above, for example, it has been confirmed that the sequence of amino acids 46 to 51 in SEQ ID NO: 2, 4, 6 or 8 is associated with the resistance to glucose-induced inactivation/degradation in Mal21p, Mal31p, Mal61p and Mtt1p, and the sequence of amino acids 51 to 56 in SEQ ID NO: 10 is associated with the resistance in Agt1. Accordingly, when a mutation is introduced, a polynucleotide is designed to encode, e.g., a sequence in which amino acids in this fragment are replaced by other amino acids, based on this sequence information. Furthermore, since the replaceable amino acids can be specified to some extent as described above, a polynucleotide sequence encoding an amino acid sequence in which such replaceable amino acids are substituted with one another can be designed. Examples of the amino acid sequence used as a basis are sequences including naturally occurring Mal21p (SEQ ID NO: 2); mutant Mal31p (SEQ ID NO: 38, 40, 42, 44, 46 or 48), mutant Mal61p (SEQ ID NO: 26 or 28), mutant Mtt1p (SEQ ID NO: 34) and mutant Agt1p (SEQ ID NO: 32, 34), which are obtained in EXAMPLES described later, and the like.

[Step (4)]

This step involves constructing an expression vector bearing the polynucleotide designed in the step (3), introducing the vector into a yeast in a conventional manner and culturing the yeast in an oligosaccharide medium (e.g., a maltose medium). Preferably, the yeast into which the polynucleotide designed in this step (3) has been introduced includes mutant Mal31p protein wherein a site-directed mutation is introduced into the amino acid sequence of Mal31p protein, mutant Mal61p protein wherein a site-directed mutation is introduced into the amino acid sequence of Mal61p protein, mutant Mtt1p protein wherein a site-directed mutation is introduced into the amino acid sequence of Mtt1p protein and mutant Agt1p protein wherein a site-directed mutation is introduced into the amino acid sequence of Agt1p protein. The aptitude of yeast can be evaluated by measuring the resistance to glucose-induced inactivation/degradation of the transporter contained in the yeast, oligosaccharide assimilability, growth rate, fermentation rate in wort, etc. of the yeast during its culture. The resistance to glucose-induced inactivation/degradation, oligosaccharide assimilability, growth rate, fermentation rate in wort, etc. can be evaluated by the methods used in EXAMPLES described later.

EXAMPLES

Hereinafter, the present invention will be described in more detail with reference to EXAMPLES but is not deemed to be limited thereto.

[Testing Methods]

Test items and testing methods used in EXAMPLES are shown below. The testing methods in EXAMPLES were performed in accordance with the methods below, unless otherwise indicated.

<Acquisition of the MAL61, MAL31, MAL21 and AGT1 Genes>

The MAL61, MAL31 and AGT1 genes of *Saccharomyces cerevisiae* are already cloned and their nucleotide sequences are reported. MAL31 (SEQ ID NO: 3), MAL61 (SEQ ID NO: 5) and AGT1 (SEQ ID NO: 9) used in the present invention were obtained from the *Saccharomyces* Genome Database Accession No. YBR298C, the GenBank Accession No. X17391 and the *Saccharomyces* Genome Database Accession No. YGR289C, respectively. The MAL61, MAL31 and AGT1 genes were amplified by PCR using as a template the chromosomal DNA bearing each gene, which was prepared from yeast *Saccharomyces cerevisiae*, and then isolated to obtain the MAL61, MAL31 and AGT1 genes.

Also, MAL21 was known to be encoded by chromosome III, but its DNA sequence was unknown. However, as MAL31 encoded by chromosome II and MAL61 encoded by chromosome VIII had the identity of 99% or more, it was expected that MAL21 would also have a considerably high identity.

Actually in this EXAMPLE, all of the MAL21, MAL31 and MAL61 genes could be obtained using chromosomal DNA of the yeast strain bearing each α-glucoside transporter only as a template and using the same primers (5'AGAGCTCAGCATATAAAGAGACA 3' (SEQ ID NO: 11) and 5'TGGATCCGTATCTACCTACTGG 3' (SEQ ID NO: 12)). AGT1 was obtained using the primers (5'TGAGCTCACATAGAAGAACATCAAA 3' (SEQ ID NO: 13) and 5'ATGGATCCATATGAAAAATATCATT 3' (SEQ ID NO: 14)). Specifically, MAL31 and AGT1 were obtained by PCR from *Saccharomyces cerevisiae* S288C (ATCC204508 (Rose, M. D., Winston, F. and Hieter, P. (1990): Methods in Yeast Genetics: A Laboratory Course Manual, Cold Spring Harbor Laboratory Press, Cold Spring Harbor, N.Y.)), MAL61 from *Saccharomyces cerevisiae* ATCC96955, and MAL21 from *Saccharomyces cerevisiae* ATCC20598.

The DNA fragment thus obtained was inserted into vector pCR (registered trademark) 2.1-TOPO using TOPO TA cloning kit of Invitrogen Inc. and then subjected to DNA sequencing to verify the inserted gene sequence. It was confirmed that the sequences of MAL31, MAL61 and AGT1 are the same as the sequences registered in the data bank (Accession Nos. YBR298C, X17391 and YGR289C, respectively). With respect to MAL21, 10 clones or more were sequenced independently to verify the sequence (SEQ ID NO: 1).

The primers used contain a XbaI or SacI site upstream of the initiation codon and a BamHI site downstream of the termination codon and are designed to integrate into the expression vector. Amplification of the target gene by PCR using chromosomal DNA and subsequent isolation can be performed by methods well known to those skilled in the art, including preparation of PCR primers.

<Obtaining MTT1 Gene>

The genomic DNA of bottom-fermenting beer yeast Weihenstephan 34/70 was prepared and the DNA library was constructed using plasmid YCp49H (FIG. 19) as a vector. This library was transformed into *Saccharomyces cerevisiae* HH150 (CB11Δagt1::G418R) and the transformant was spread onto a minimum medium supplemented with 300 μg/ml of hygromycin and 0.5% maltotriose. As the CB11 strain is an ade1 strain, the adenine precursor 5-aminoimidazole riboside is accumulated and further polymerized to turn the colonies red. When AGT1-disrupted HH150 (CB11Δagt1::G418R) was spread onto a medium containing maltotriose as the only one carbon source, its growth became extremely slow and the colonies were white. When antimycin is added to the medium, it is possible to stop the growth completely in a medium containing maltotriose as the only one carbon source. Since antimycin is highly toxic, it was attempted to acquire a maltotriose transporter, without using antimycin, by selecting the red colonies. After culturing at 30° C. for 3 days, the red colonies grown were streaked onto the same medium, thus confirming that the colonies grew in the medium. A plasmid was prepared from 21 red colonies well grown. The plasmid was transformed into *Escherichia coli* DH5α. The plasmid was mass-produced in *Escherichia coli*. The plasmid was transformed again into HH150 and spread onto the same medium. The plasmid was extracted from 18 red colonies well grown.

DNA sequencing of the inserted fragment was carried out to find the same sequence suspected of being a transporter having a 90% identity with MAL61 in 17 colonies. This gene had exactly the same sequence as MTT1 (GenBank Accession No. DQ010171) reported in J. Dietvorst, et al., Yeast, 2005, 22:775-788. Therefore, the gene is called MTT1 (its nucleotide sequence and amino acid sequence are shown by SEQ ID NO: 7 and SEQ ID NO: 8, respectively). Using primers (5'TCTAGAATTACATCCAAGACTATTAATTAACTATG 3' (SEQ ID NO: 15) and 5'TGGATCCGTATCTACCTACTGG 3' (SEQ ID NO: 16)), the MTT1 gene into which a XbaI site was introduced upstream of the initiation codon and a BamHI site was introduced downstream of the termination codon by PCR was incorporated into the expression vector.

<Expression Plasmid/Plasmid for Library Construction>

In the present invention, the four expression vectors (1) to (4) were used and (5) was used as a plasmid for library construction.

(1) pJHXSB (FIG. 15)
(2) pJHIXSB (FIG. 16)
(3) pYCGPY (FIG. 17)
(4) pUP3GLP (FIG. 18)
(5) YCp49H (FIG. 19)
<Yeast Strains>
In the present invention, the strains (1) to (6) were used for the acquisition of transporter genes and comparison among the strains, the strains (7) to (10) were used to confirm the growth rate and fermentation rate in strains bearing transporters highly expressed, and the strain (11) to acquire mutant genes.
(1) S. cerevisiae S288C (ATCC204508) (MATalpha SUC2 mal mel gal2 CUP1)
(2) S. cerevisiae ATCC96955 (MATa MAL61 MAL62 MAL63 mal64 mal11 MAL12 mal13 ura3-52 leu2-3 leu2-112 trp1 his)
(3) S. cerevisiae ATCC20598 (MATa suc MAL2 MEL1 his4 leu2)
(4) S. cerevisiae CB11 (Berkley Stock Center) (MATa ade1 MAL61 MAL62 MAL63 AGT1 MAL12 MAL31 MAL32)
(5) bottom-fermenting beer yeast Weihenstephan 34/70
(6) S. cerevisiae HH150=(CB11 Δagt1:G418R) (MATa ade1 MAL61 MAL62 MAL63 Δagt1::G418R MAL12 MAL31 MAL32)
(7) S. cerevisiae HH1001 (MATa SUC2 mal mel gal2 CUP1 TPI1::TPI1pr-MAL32-G418R ura3)
(8) S. cerevisiae Δ152MS (MATa mal61::TRP1 MAL62 MAL63 mal64 mal11 MAL12 mal13 leu2-3 leu2-112 his URA3::TDH3p::MAL62)
(9) top-fermenting beer yeast AH135
(10) bottom-fermenting beer yeast Weihenstephan 194
(11) S. cerevisiae HH1002 (MATa SUC2 mal mel gal2 CUP1 TPI1::TPI1pr-MAL32-G418R ura3 dog1 dog2)
<Introduction of Site-Directed Mutagenesis>
In EXAMPLES, after the transporter gene obtained was inserted into expression vector pJHIXSB, a mutation was introduced by using ExSite™ PCR-Based Site-Directed Mutagenesis Kit/STRATAGENE with the primers (TABLE 1). For details on the technique for introducing the mutation, the procedures were performed following the manual from STRATAGENE.

the same level as that of glucose. It is thus highly probable that a strain grown on this plate would have an α-glucoside transporter less susceptible to glucose-induced inactivation. To determine the resistance to 2-DOG, the following 2 media were used: [1] 0 to 2.0 mM 2-deoxyglucose-containing maltose synthetic complete medium (SCM) (6.7 g/L of yeast nitrogen base w/o amino acids, 20 g/L of maltose, 20 mg/ml of adenine sulfate, 20 mg/ml of uracil, 20 mg/ml of L-tryptophan, 20 mg/ml of L-histidine hydrochloride, 20 mg/ml of L-arginine hydrochloride, 20 mg/ml of L-methionine, 30 mg/ml of L-tyrosine, 30 mg/ml of L-leucine, 30 mg/ml of L-isoleucine, 30 mg/ml of L-lysine hydrochloride, 50 mg/ml of L-phenylalanine, 100 mg/ml of L-glutamic acid, 100 mg/ml of L-aspartic acid, 150 mg/ml of L-valine, 200 mg/ml of L-threonine and 400 mg/ml of L-serine), or [2] 0 to 2.0 mM 2-deoxyglucose-containing maltose minimum medium (6.7 g/L of yeast nitrogen base w/o amino acids and 20 g/L of maltose). The resistance was determined by spotting the serial dilution of cell suspension of each transporter-expressed strain by 3 μl each onto any plate and culturing at 30° C. for 2 to 3 days.
<Measurement of Level of Transporter Protein Accumulated in Cells>
The level of transporter protein accumulated in cells can be assayed by, e.g., Western blotting. For example, a test strain is harvested from 10 ml of culture broth in the logarithmic growth phase and disrupted in a lysis buffer (8 M urea, 5% (w/v) SDS, 40 mM Tris-HCl (pH6.8), 0.1 mM EDTA, 1% β-mercaptoethanol) by stirring with glass beads to give the cell extract. A sample of 60 μg total protein was developed by SDS-gel electrophoresis and transferred onto a nitrocellulose membrane followed by Western blotting using rabbit polyclonal anti-Mal61p antibody.
The rabbit polyclonal anti-Mal61p antibody was obtained as follows. The procedures involves inserting a DNA encoding the N-terminal region (Met1-Leu181) of Mal61p at the downstream of GST tag in the pET Expression vector (Novagen), transforming the resulting plasmid into Escherichia coli BL21 (DE3), applying a cell lysate of the transformant to a GST bind resin column and eluting the protein bound to the column. Full details are given in manual attached to Novagen's pET Expression System, GST-Bind™ Affinity Resins (Novagen). The fused protein thus prepared was

TABLE 1

Sequences of primers used for site-directed mutagenesis

| Mutant Gene | Primer Sequence | SEQ ID NO: |
|---|---|---|
| MAL61[D46G] | 5'-GTCTTTCCCATCTTGAGTACGGTCC-3' | 17 |
| | 5'-CAAAATCACTTTTCTTACCTTGCTCCT-3' | 18 |
| MAL61[L50H] | 5'-ATGAGTACGGTCCAGGTTCACTAA-3' | 19 |
| | 5'-GATGGGAAAGATCAAAATCACTTTTC-3' | 20 |
| MAL61[D46G, L50H] | 5'-GTCTTTCCCATCATGAGTACGGTCCA-3' | 21 |
| | 5'-CAAAATCACTTTTCTTACCTTGCTCCT-3' | 22 |
| MTT1[D46G] | 5'-GTCTTTCCCATCATGAGTACGGTCC-3' | 23 |
| | 5'-CAAAATCACTTTTCTTACCTTGCTCCT-3' | 24 |

<Evaluation of Transporter Protein on 2-Deoxyglucose Resistance>
2-Deoxyglucose (2-DOG) is a sugar analog that is metabolized to 2-DOG-6-phosphate but not any further and thus cannot be a carbon source. However, it is known that 2-DOG induces glucose repression or glucose-induced inactivation to applied to SDS-PAGE to confirm the purity. Then, rabbit was immunized using the fused protein as an immunogen to obtain the polyclonal antibody. Effectiveness of the antibody was confirmed by culturing the α-glucoside transporter gene (MAL61, MAL31 or MAL21)-expressed yeast strain and its host strain free of the gene in a YPM medium (10 g/L of yeast extract, 20 g/L of polypeptone and 5.0 g/L of maltose) and performing Western blotting for the cell lysate using this antibody by the method described above. Positive bands consistent with the molecular weights of α-glucoside transporters (MAL61, MAL31 and MAL21) of 68 kDa were detected only in the lysate of the yeast strain in which the α-glucoside transporter gene was expressed.

The level of Agt1p accumulated in the cells was determined by constructing a gene encoding the fused protein bearing two tandem hematoagglutinin (HA) tags at the C-terminal end of Agt1p, obtaining a strain expressing the gene and using the strain according to the methods described above. Mouse monoclonal anti-hematoagglutinin antibody (Covance, Research, Products, Inc.) was used as the antibody.

<Measurement of Degradation Rate of Transporter Protein>

The strain expressing each transporter protein was inoculated into YPD followed by shaking culture at 30° C. overnight. The culture was inoculated into a YPM medium to OD660=1.0, shaking the culture at 30° C. for 2.5 hours and then collected. The 60 OD660 units of cells were measured and suspended in 30 ml of a medium for degradation rate measurement (1.7 g/L of yeast nitrogen base w/o amino acids and ammonia, 20 g/L of glucose and 25 mg/L of cycloheximide) preincubated at 30° C., followed by incubation at 30° C. The cell suspension was sampled by 5 ml at an appropriate time (0, 10, 20, 30 and 40 minutes or 0, 30, 60, 90 and 120 minutes) immediately followed by centrifugation. The supernatant was discarded and the cells were frozen using an ethanol-dry ice. The transporter protein was detected from the frozen cells by the method described above and the intensity of the protein band was measured to determine the half life from its diminution rate.

<Mutant Mal61p/Mutant Agt1p/Mutant Mtt1p/Mutant Mal31p>

The mutant Mal61p/mutant Agt1p/mutant Mtt1p/mutant Mal31p in this invention refer to the 13 transporter proteins shown in TABLES 2, 3, 4 and 5, respectively.

TABLE 2

Sequence of amino acids 39 to 52 of mutant and native α-glucoside transporter (Mal61p)

| Transporter | Amino acid sequence 39 ... 52 | SEQ ID NO: | Half life (min.) |
|---|---|---|---|
| Mal161p | QGKKSDFDLSHLEY | Residues 39-52 of SEQ ID NOS 4 and 6 | 25 |
| Mal21p | QGKKSDFGLSHHEY | 52 | 118 |
| Mal61p[Gly46] | QGKKSDFGLSHLEY | 53 | 45 |
| Mal61p[His50] | QGKKSDFDLSHHEY | Residues 39-52 of SEQ ID NO: 8 | 37 |
| Mal61p[Gly46, His50] | QGKKSDFGLSHHEY | 54 | 134 |

TABLE 3

Sequence of amino acids 44 to 57 of mutant and native α-glucoside transporter (Agt1p)

| Transporter | Amino acid sequence 44 ... 57 | SEQ ID NO: | Half life (min.) |
|---|---|---|---|
| Agt1p | GKKDSAFELDHLEF | Residues 44-57 of SEQ ID NO: 10 | 14 (Agt1-HAp) |
| Agt1p[Lys56] | GKKDSAFELDHLKF | 55 | — |
| Agt1p[Gly56] | GKKDSAFELDHLGF | 56 | 148 (Agt1-HAp[Gly56]) |

TABLE 4

Sequence of amino acids 39 to 52 of mutant and native α-glucoside transporter (Mtt1p)

| Transporter | Amino acid sequence 39 ... 52 | SEQ ID NO: |
|---|---|---|
| Mtt1p | QGKKSDFDLSHHEY | Residues 39-52 of SEQ ID NO: 8 |
| Mtt1p[Gly46] | QGKKSDFGLSHHEY | 57 |

TABLE 5

Sequence of amino acids 39 to 52 of mutant
and native α-glucoside transporter (Mal31p)

| Transporter | Amino acid sequence 39　　　　　52 | SEQ ID NO: | Half life (min.) |
|---|---|---|---|
| Mal31p | QGKKSDFDLSHLEY | Residues 39-52 of SEQ ID NOS 4 and 6 | 21 |
| Mal21p | QGKKSDFGLSHHEY | 58 | 118 |
| Mal31p[Val51] | QGKKSDFDLSHLVY | 59 | 134 |
| Mal31p[Pro48] | QGKKSDFDLPHLEY | 60 | >360 |
| Mal31p[Pro49] | QGKKSDFDLSPLEY | 61 | >360 |
| Mal31p[Pro50] | QGKKSDFDLSHPEY | 62 | >360 |
| Mal31p[Lys51] | QGKKSDFDLSHLKY | 63 | 187 |
| Mal31p[Phe50, Lys51] | QGKKSDFDLSHFKY | 64 | >360 |
| Mal31p[Arg49] | QGKKSDFDLSRLEY | 65 | — |

In the tables, only the regions containing amino acid residues different from the respective native transporters are shown. The amino acid residues replaced by the mutation treatment with UV or the mutation by site-directed mutagenesis are represented in bold letters. The mutant transporter protein of the invention has the characteristic of high stability in a yeast even in the presence of glucose. In the tables the sequences of native transporters are also shown. Among the native transporters, only Mal21p has the characteristic of high stability in a yeast even in the presence of glucose. The amino acids of Mal21p which are different from those of Mal31p or Mal61p are shown in bold.

Throughout the specification, the protein of the mutant transporter is represented as follows. For example, Mal61p [Gly46, His50] (SEQ ID NO: 30) represents mutant Mal61p in which the 46th aspartic acid is replaced by glycine and the 50th leucine is replaced by histidine. The gene for this mutant transporter is represented by MAL61[D46G, L50H] (SEQ ID NO: 29).

<Evaluation of Maltose Assimilability>

Assimilation of maltose by a yeast constitutively expressing the mutant transporter can be evaluated by aerobically culturing or fermenting the yeast under conditions suitable for the yeast and measuring the amount of maltose in a medium. Sugars can be measured by methods well known to those skilled in the art, for example, liquid chromatography using an IR detector. In the yeast in the present invention described later, the ability of maltose uptake was improved.

Example 1

Screening of α-Glucoside Transporter Having the Resistance to Glucose-Induced Inactivation/Degradation To 2% maltose-containing synthetic complete medium (SCM), 0 mM to 2 mM 2-deoxyglucose (2-DOG) was added to make a plate. 2-DOG is a sugar analog that is metabolized to 2-DOG-6-phosphate but not any further and thus cannot be a carbon source. However, it is known that 2-DOG induces glucose repression or glucose-induced inactivation to the same level as glucose. It is thus highly probable that a strain grown on this plate would have an α-glucoside transporter less susceptible to glucose-induced inactivation. With regard to a number of yeast strains, the cell suspension was spotted and incubated at 30° C. As a result, MAL21-bearing yeast strain ATCC 20598 grew even on a plate containing 1 mM 2-DOG unlike other strains, indicating that MAL21 in the strain was predictably a transporter less susceptible to glucose-induced degradation (FIG. 1). Thus, the primers (TABLE 1, supra) were designed based on the nucleotide sequence information about 5' upstream and 3' downstream of MAL61 encoding gene. MAL21 gene was amplified by PCR using the ATCC 20598 genomic DNA as a template and cloned into Invitrogen's pCR2.1-TOPO followed by DNA sequencing. The nucleotide sequence (SEQ ID NO: 1) and the amino acid sequence (SEQ ID NO: 2) are shown in FIGS. 2 and 3, respectively.

This MAL21 gene was incorporated into the SacI-BamHI site of plasmid pJHIXSB (FIG. 16). After digesting with EcoRV in the URA3 gene, this plasmid pJHIMAL21 was incorporated into yeast HH1001 as an expression unit constitutively transcribed by TPI1 promoter, which was designated as HH206 strain. HH1001 is a ura3-sibling of the mal-strain X2180-1A and constitutively expresses maltase since TPI1p:: MAL32 (which encodes maltase gene) is incorporated therein. Growth of the HH206 strain was examined by applying the strain onto a maltose minimum medium plate containing 0 mM to 2 mM 2-DOG. The HH108, HH227 and HH228 strains bearing the MAL61, MAL31 and AGT1 genes could not grow on the plate containing 1.0 mM of 2-DOG whereas the HH206 strain grew on the plate containing 2.0 mM of 2-DOG.

In addition, the glucose-induced degradation rate of Mal21p was assayed by Western blotting using anti-Mal61p antibody. It was found that the half life was approximately 2 hours, whereas the half life of Mal31p and Mal61p was about 20 minutes. It was confirmed that Mal21p has a much longer half life than the other transporters (FIG. 4).

Example 2

Screening for Mutant Mal31p and Mutant Agt1p Having the Resistance to Glucose-Induced Inactivation/Degradation The MAL31 and AGT1 genes were obtained by PCR from S. cerevisiae S288C strain in a manner similar to EXAMPLE 1. These genes were inserted at the downstream of TPI1 promoter in pJHXSB (FIG. 15) to construct plasmids pJH-MAL31 and pJHAGT1, followed by transformation into HH1002. HH1002 is a strain with disruption of DOG1 and DOG2 which encode 2-deoxyglucose phosphate phosphatase from HH1001. When 2-deoxyglucose phosphate phosphatase is highly expressed, the toxicity of 2-DOG for yeasts is lost. Accordingly, a strain with such a mutation in which these two genes are highly expressed is considered to grow on SCM medium containing 2-DOG Consequently, HH1002 strain deleted of DOG1 and DOG2 was used to obtain a mutant transporter gene. HH1002 (pJHMAL31) and HH1002 (pJHAGT1) were spread onto a SCM plate supplemented with 8.0 mM of 2-DOG in $10^9$ cells/plate.

This plate was exposed to UV rays to the lethality rate of 80%. After incubation at 30° C. for 8 days, 180 colonies grew in HH1002 (pJHMAL31) and in HH1002 (pJHAGT1) 92 colonies grew. They were again streaked onto SCM plate supplemented with 2.0 mM of 2-DOG, and 169 colonies grew in HH1002 (pJHMAL31) and in HH1002 (pJHAGT1) 6 colonies grew.

After the plasmid was extracted from several strains of these colonies and transformed into *E. coli* DH5α, the plasmid was prepared from the transformant and again transformed into HH1002 strain. By confirming growth of the transformant on a SCM plate supplemented with 2.0 mM of 2-DOG, it was verified that the mutant transporter has imparted a character of 2-DOG resistance.

Sequencing of 42 MAL31 mutant genes and 20 AGT1 mutant genes gave 7 different MAL31 mutant genes and 2 different AGT1 mutant genes. Translation of the MAL31 mutant gene sequences into amino acid sequences revealed that a mutation has occurred in all of the MAL31 mutant genes within the region encoding four amino acid residues-SHLE consisting of the 48th serine to the 51st glutamic acid (TABLE 5). Among these mutants, the glucose-induced degradation rate of six Mal31p mutants, i.e., Mal31p[Val51] (SEQ ID NO: 38), Mal31p[Pro48] (SEQ ID NO: 40), Mal31p [Pro49] (SEQ ID NO: 42), Mal31p[Pro50] (SEQ ID NO: 44), Mal31p[Lys51] (SEQ ID NO: 46) and Mal31p[Phe50,Lys51] (SEQ ID NO: 48), was determined by Western blotting. As shown in FIG. 5, it was found that all of the mutant transporters have much longer half lives than the wild-type.

Furthermore, translation of the AGT1 mutant gene sequences into amino acid sequences revealed that a mutation has occurred at the codon encoding the 56th glutamic acid in two AGT1 mutant genes (TABLE 4). With Agt1-HAp[Gly56] wherein HA-tag (SEQ ID NO: 52) was fused at the C-terminal end of a mutant Agt1p, Agt1p[Gly56] (SEQ ID NO: 34), and Agt1-HAp wherein HA-tag was likewise fused to wild-type Agt1p, the glucose-induced degradation rate was determined by Western blotting. As shown in FIG. 8, it was found that Agt1-HAp[Gly56] has much longer half lives than Agt1-HAp.

In view of the alignment of the amino acid sequences of Mal31p and Agt1p, the 56th glutamic acid in Agt1p corresponds to the 51st glutamic acid of Mal31p. It has thus been found that the resistance to glucose-induced degradation can be imparted to both transporters by introducing the amino acid substitution into the corresponding four amino acid residues (SHLE in Mal31p and DHLE in Agt1p).

Furthermore, in view that in the mutant strains, substitution to proline, lysine, valine, phenylalanine, arginine, glycine, etc. occurs and amino acids having large side or main chains, amino acid residues such as proline, glycine, etc. which tend to disrupt alpha helices are contained, it is inferred that the 2-deoxyglucose resistance, i.e., the character less susceptible to glucose-induced inactivation or degradation has been acquired by changing the secondary structure near this region.

Example 3

Identification of Amino Acid Residues in Mal21p Involved in the Resistance to Glucose-Induced Inactivation/Degradation Comparing the amino acid sequences between Mal21p and Mal61p or Mal21p and Mal31p, the amino acid residues which are commonly different therebetween are six of Gly46, His50, Leu167, Leu174, Val175 and Thr328. Based on the information obtained in EXAMPLE 2, the gene MAL61 [D46G, L50H] (SEQ ID NO: 29) encoding the transporter in which Asp46 in Mal61p was replaced by Gly46 and Leu50 in Mal61p was replaced by His50 among these different amino acid residues was prepared and introduced into plasmid pJHIXSB.

After plasmid pJHIMAL61[D46G, L50H] was digested with EcoRV in the URA3 gene, the digestion product was incorporated into yeast HH1001 as an expression unit constitutively transcribed by TPI1 promoter to produce HH207 strain. Growth of the HH207 strain on a SCM plate supplemented with 2-DOG was examined; the HH207 strain grew in a maltose minimum medium supplemented with 2 mM of 2-DOG as the HH206 strain bearing Mal21p did, expecting that the strain would have the same glucose resistance as in Mal21p.

Next, genes MAL61[D46G] (SEQ ID NO: 25) and MAL61 [L50H] (SEQ ID NO: 27) encoding the transporters having the substitution of each one residue of these two residues were produced and their expression strains HH210 and HH209 were produced as described above. Growth of these strains were examined in a maltose minimum medium supplemented with 2-DOG. These strains had a higher resistance to 2-DOG than the HH108 strain bearing Mal61p but a lower resistance than the HH206 strain. Thus, it was found that in order to impart a resistance equal to that of Mal21p to Mal61p, both substitutions from Asp46 to Gly46 and from Leu50 to His50 are required (FIG. 9).

The glucose-induced degradation rate of these three mutant transporters, i.e., Mal61p[Gly46, His50] (SEQ ID NO: 30), Mal61p[Gly46] (SEQ ID NO: 26) and Mal61p [His50] (SEQ ID NO: 28) was determined by Western blotting. As is inferred from the 2-DOG resistance, only Mal61p [Gly46, His50] showed almost the same half life as that of Mal21p (FIG. 9).

In other words, the 46th aspartic acid in Mal31p is also a residue suitable for the amino acid substitution for imparting the resistance to glucose-induced inactivation/degradation, in addition to the four amino acids from the 48th serine to the 51st glutamic acid in Mal31p, as demonstrated in EXAMPLE 2. In EXAMPLE 3, the 46th aspartic acid was substituted with glycine. Note that glycine is the amino acid having a tendency to disrupt alpha helices.

Furthermore, the 50th leucine is substituted with histidine and histidine is also the amino acid having a tendency to disrupt alpha helices. According to the secondary structure prediction by Chou-Fasman, it is predicted that the 44-54 amino acid region of Mal61p will be an alpha helix, and even though any of the substitutions from Asp46 to Gly46 and from Leu50 to Hsp50 is made, the predicted structure of this region changes from the alpha helix to a random coil.

Considering these results in EXAMPLES 2 and 3, the resistance to glucose-induced inactivation/degradation can be imparted to the α-glucoside transporter by introducing the amino acid substitution to change the secondary structure in the region comprising the sequence of amino acids 46 to 51 (DLSHLE or DLSHHE) in the amino acid sequence of SEQ ID NO: 4, 6 or 8, or into the sequence of amino acids 51 to 56 (ELDHLE) in the amino acid sequence of SEQ ID NO: 10.

Example 4

Production of Alpha-Glucoside Transporter MTT1 Having the Resistance to Glucose-Induced Inactivation/Degradation Bottom-fermenting beer yeast has MTT1, which is a kind of alpha-glucoside transporter gene not found in laboratory strains of Saccharomyces cerevisiae, and has an identity of about 90% with MAL61 as the α-glucoside transporter gene on an amino acid level (the DNA sequence and amino acid sequence are shown by SEQ ID NO: 7 and SEQ ID NO: 8, respectively). Alignments of the amino acid sequences of Mal12p/Mal31p/Mal61p/Mtt1p/Agt1p are shown in FIGS. 6 and 7. Analysis of this transporter Mtt1p revealed that Mtt1p has excellent properties such as a high activity even at low temperatures, a faster uptake rate of maltotriose than Agt1p, etc. but has a lower resistance to 2-DOG, unlike Mal21p.

Thus, the focus was drawn onto the sequence of amino acids 46 to 51 based on EXAMPLES 2 and 3. The sequence of amino acids 46 to 51 in Mtt1p are DLSHHE and when compared to Mal21p, only the 46th residue is different from Mal21p, which was aspartic acid (D in the one-letter amino acid designation) as in Mal61p.

Accordingly, mutant MTT1[D46G] gene (SEQ ID NO: 35) in which this residue was substituted with glycine was produced and introduced into plasmid pJHIXSB. After digesting plasmid pJHIMTT1[D46G] with EcoRV in the URA3 gene, the digested product was incorporated into yeast HH1001 as an expression unit constitutively transcribed by TPI1 promoter to produce HH212 strain.

The pJHIMTT1-incorporated HH211 strain could hardly grow in a maltose minimum medium supplemented with 0.5 mM of 2-DOG, whereas the HH212 strain grew, even though slightly, in a maltose minimum medium supplemented with 1 mM of 2-DOG, indicating that a more potent glucose resistance than native Mtt1p could be imparted (FIG. 11).

Example 5

Growth of MAL61-Highly Expressed Strain and MAL21-Highly Expressed Strain in Maltose Medium MAL61 and MAL21 were incorporated into plasmid pYCGPY at the SacI-BamHI site downstream of the PYK1 promoter. The respective plasmids were named pYCGPYMAL61 and pYCGPYMAL21. The plasmid pYCGPY is a YCp type plasmid bearing CEN-ARS and has a G418-resistant gene, Ap-resistant gene, etc. (FIG. 17). pYCGPYMAL61 and pYCGPYMAL21 were transformed into Δ152MS strain. The Δ152 strain is a strain into which MAL61 in ATCC 96955 is disrupted by TRP1 marker and MAL62 (maltase gene) under control of TDH3 promoter is introduced. Δ152MS (pYCGPYMAL61) and Δ152MS(pYCGPYMAL21) were inoculated into YPM (10 g/L of yeast extract, 20 g/L or polypeptone and 5.0 g/L of maltose) to OD 660=about 0.5, followed by shaking the culture at 30° C. The OD660 was monitored every 1.5 hour (FIG. 12). Δ152MS(pYCGPYMAL21) grew more rapidly in maltose than Δ152MS(pYCG-PYMAL61), and the effect of the transporter having the resistance to glucose-induced degradation was confirmed in the laboratory strain.

Example 6

Test on Happoshu (Low-Malt Beer) Wort Fermentation by Bottom-Fermenting Beer Yeast Where MAL21 Was Highly Expressed The transporter MAL21 having the resistance to glucose-induced degradation was incorporated into plasmid pUP3GLP at the XbaI (or SacI)-BamHI site. pUP3GLP is shown in FIG. 18. pUP3GLP is a YIp-type plasmid, in which the transporter gene is expressed from glyceraldehyde triphosphate dehydrogenase promoter (TDH3p). After each plasmid was digested at the EcoRV site in URA3, the digested product was transformed into bottom-fermenting beer yeast (Weihenstephan 194) and the transformant was spread onto a YGP plate (10 g/L of yeast extract, 20 g/L of polypeptone and 20 g/L of galactose) supplemented with 0.3 µg/ml of cycloheximide. It was confirmed by PCR that the objective expression cassette was inserted into the URA3 gene on the chromosome of Weihenstephan 194.

Weihenstephan 194 (URA3::TDH3p::MAL21) and parent strain Weihenstephan 194 were inoculated into two kinds of happoshu wort. The happoshu wort is a wort with less than 25% malt content in the raw materials except for water, in which glycosylated starch, hops, etc. are used. One of the worts for happoshu has an initial extract concentration of 14.0% and contains sugars in proportions of 1.2% of glucose, 6.6% of maltose and 2.2% of maltotriose. Another glucose-rich happoshu wort has an initial extract concentration of 15.6% and contains sugars in proportions of 4.7% of glucose, 5.4% of maltose and 1.7% of maltotriose. Each wort was prepared by adding glycosylated starch having different sugar proportions to the same volume of wort (final concentration, less than 25% malt content). Wet cells were pitched into each happoshu wort adjusting to 7.5 g/L, which was allowed to ferment at 15° C. The maltose content in the moromi mash during the fermentation was measured. The results are shown in FIG. 13.

In any happoshu wort, the assimilation rate of maltose in the MAL21-highly expressed strains was markedly faster than in the parent strain Weihenstephan 194. Especially in the case of glucose-rich happoshu wort, its effect was remarkable.

The high initial extract concentration means that the glucose content is high and in this case, the effect of the transporter having the resistance to glucose-induced degradation was fully observed.

Example 7

Wort Fermentation Test by Top-Fermenting Beer Yeast in which MAL21 or AGT1[E56G] was Highly Expressed Glucose-induced degradation-resistant transporter MAL21 or AGT1[E56G] was introduced into plasmid pUP3GLP at the XbaI (or SacI-BamHI site. pUP3GLP is shown in FIG. 18. pUP3GLP is a YIp-type plasmid and the transporter gene is expressed by glyceraldehyde triphosphate dehydrogenase promoter (TDH3p). After each plasmid was digested at the EcoRV site in URA3, the digested product was transformed into top-fermenting yeast AH135 and the transformant was spread onto a YPG plate (10 g/L of yeast extract, 20 g/L of polypeptone and 20 g/L of galactose) supplemented with 0.3 µg/ml of cycloheximide. It was confirmed by PCR that the objective expression cassette was inserted into URA3 gene on the chromosome of AH135. AH135 (URA3:: TDH3p::MAL21) and AH135 (URA3::TDH3p:: AGT1 [E56G]) were pitched into a 100% malt wort containing an initial extract concentration of 13% or 20% with adjusted to 5 g/L of wet cells. Fermentation was performed at 15° C. and the maltose concentration in the mash during fermentation was measured. The results are shown in FIG. 14.

The maltose assimilation rate was faster than the parent strain AH135 even using either strain. Especially in the case of the initial extract concentration of 20%, its effect was remarkable. The initial extract concentration being high indicates that the glucose concentration is high, meaning that the transporter having the resistance to glucose-induced degradation was effective. It was confirmed that the high expression of the transporter having the resistance to glucose-induced degradation was effective not only for the bottom-fermenting beer yeast but also for top-fermenting beer yeast.

(Summary)

As described above, it has been found that Mal21p naturally occurring in some yeast is less susceptible to glucose-induced degradation, unlike other α-glucoside transporters. Also, the amino acid region which greatly affects the degradation rate of α-glucoside transporters normally rapidly degraded by glucose has been identified and by replacing the amino acid residues in the region, the resistance to glucose-induced degradation transporter could be imparted to transporters. It has also been confirmed that assimilation of sugars such as maltose in mash, etc. taken up by the transporter can be accelerated by using yeasts (irrespective of laboratory strains or brewing yeasts) capable of expressing the mutant transporter. Especially when the concentration of monosaccharides such as glucose is higher, the effects are more prominent.

INDUSTRIAL APPLICABILITY

The yeast bearing the transporter in accordance with the present invention which has the resistance to glucose-induced inactivation/degradation provides improved oligosaccharide assimilability and is excellent in its ability to assimilate oligosaccharide such as maltose. Such yeast can be effectively used in brewing beer or wine.

The invention claimed is:

1. An isolated polynucleotide that encodes a protein comprising the amino acid sequence of SEQ ID NO: 34, wherein the protein has resistance to glucose-induced inactivation or degradation.

2. The isolated polynucleotide of claim 1, which is a DNA.

3. A vector comprising the isolated polynucleotide of claim 1.

4. A yeast transformed with the vector of claim 3.

5. The yeast of claim 4, which is for brewing.

6. The yeast of claim 5, wherein oligosaccharide assimilability is improved by increasing the expression level of the isolated polynucleotide.

7. An isolated polynucleotide comprising the nucleotide sequence of SEQ ID NO: 33.

8. The isolated polynucleotide of claim 7, which is a DNA.

9. A vector comprising the isolated polynucleotide of claim 7.

10. A yeast transformed with the vector of claim 9.

11. The yeast of claim 10, wherein the yeast is for brewing.

12. The yeast of claim 11, wherein oligosaccharide assimilability is improved by increasing the expression level of the isolated polynucleotide.

* * * * *